(12) United States Patent
Sivaguru et al.

(10) Patent No.: US 9,738,753 B2
(45) Date of Patent: Aug. 22, 2017

(54) PROGRAMMED DEGRADATION OF POLYMERS DERIVED FROM BIOMASS

(71) Applicants: Jayaraman Sivaguru, Fargo, ND (US); Mukund P. Sibi, Fargo, ND (US); Dean C. Webster, Fargo, ND (US); Saravana Kumar Rajendran, Trichy (IN); Ramya Raghunathan, Fargo, ND (US)

(72) Inventors: Jayaraman Sivaguru, Fargo, ND (US); Mukund P. Sibi, Fargo, ND (US); Dean C. Webster, Fargo, ND (US); Saravana Kumar Rajendran, Trichy (IN); Ramya Raghunathan, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 14/883,798

(22) Filed: Oct. 15, 2015

(65) Prior Publication Data
US 2016/0108172 A1    Apr. 21, 2016

Related U.S. Application Data

(60) Provisional application No. 62/064,197, filed on Oct. 15, 2014, provisional application No. 62/074,379, filed on Nov. 3, 2014.

(51) Int. Cl.
| | | |
|---|---|---|
| C08G 63/56 | (2006.01) | |
| C07D 307/68 | (2006.01) | |
| C08G 63/685 | (2006.01) | |

(52) U.S. Cl.
CPC ....... *C08G 63/6856* (2013.01); *C07D 307/68* (2013.01)

(58) Field of Classification Search
CPC . C07D 307/68; C07D 307/70; C08G 63/6856
See application file for complete search history.

(56) References Cited

PUBLICATIONS

Alonso et al., "Bimetallic catalysts for upgrading of biomass to fuels and chemicals," *Chem. Soc. Rev.*, 2012; 41:8075-8098.
Auvergne et al., "Biobased Thermosetting Epoxy: Present and Future," *Chem. Rev.*, 2013; 114:1082-1115.
Belgacem et al., (eds), *Monomers, Polymers and Composites from Renewable Resources*, Elsevier (2008).
Besson et al., "Conversion of Biomass into Chemicals over Metal Catalysts," *Chem. Rev.*, 2014; 114:1827-1870.
Binder et al., "Simple Chemical Transformation of Lignocellulosic Biomass into Furans for Fuels and Chemicals," *J. Am. Chem. Soc.*, 2009; 131:1979-1985.
Bochet, "Photolabile protecting groups and linkers," *J. Chem. Soc., Perkin Transactions 1*, 2002; 125-142.
Bognar et al., "Synthesis of 3,4-dideoxy-dl-hex-3-enopyranosides from 5-hydroxymethyl-2-furaldehyde," *Carbohydr. Res.*, Jul. 1987; 164: 465-469.
Buntara et al., "Caprolactam from Renewable Resources: Catalytic Conversion of 5-Hydroxymethylfurfural into Caprolactone," *Angew. Chem.*, 2011; 123:7221-7225; and *Angew. Chem., Int., Ed.* 2011; 50:7083-7087.
Casanova et al., "Biomass into chemicals: aerobic oxidation of 5-hydroxymethyl-2-furfural into 2,5-furandicarboxylic acid with gold nanoparticle catalysts," *Chem Sus Chem*, 2009; 2:1138-1144.
Chen et al., "Plastics Derived from Biological Sources: Present and Future: A Technical and Environmental Review," *Chem. Rev.*, 2011; 112(4):2082-2099. Available online Dec. 2011.
Corma et al., "Chemical Routes for the Transformation of Biomass into Chemicals," *Chem. Rev.*, 2007; 107(6):2411-2502.
Dalcanale et al., "Selective oxidation of aldehydes to carboxylic acids with sodium chlorite-hydrogen peroxide," *J. Org. Chem.*, Feb. 1986; 51(4):567-569.
Gandini et al., "The Furan Counterpart of Poly(ethylene terephthalate): An Alternative Material Based on Renewable Resources," *J. Poly. Sci. A: Polymer Chem.*, 2009; 47:295-298.
Gaplovsky et al., "Photochemical reaction mechanisms of 2-nitrobenzyl compounds: 2-Nitrobenzyl alcohols form 2-nitroso hydrates by dual proton transfer," *Photochem. Photobiol. Sci.*, Jan. 2005; 4(1):33-42.
Gomes et al., "Synthesis and characterization of poly(2,5-furan dicarboxylate)s based on a variety of diols," *J. Poly. Sci. A: Polymer Chem.*, Mar. 2011; 49:3759-3768.
Griffin et al., "Photodegradable Macromers and Hydrogels for Live Cell Encapsulation and Release," *J. Am. Chem. Soc.*, 2012; 134:13103-13107.
Halliday et al., "One-Pot, Two-Step, Practical Catalytic Synthesis of 2,5-Diformylfuran from Fructose," *Org. Lett.*, May 2003; 5(11):2003-2005.
Han et al., "Fast Photodegradable Block Copolymer Micelles for Burst Release," *Macromolecules*, 2011; 44:437-439.
Han et al., "Block Copolymer Micelles with a Dual-Stimuli-Responsive Core for Fast or Slow Degradation," *Langmuir*, 2012; 28(5):2327-2331.
Huang et al., "Effects of dimethylolpropionic acid modification on the characteristics of polyethylene terephthalate fibers," *Molecular Medicine Reports* 6: 2012; 709-715.
Huber et al., "Synthesis of Transportation Fuels from Biomass: Chemistry, Catalysts, and Engineering," *Chem. Rev.*, 2006; 106:4044-4098.

(Continued)

*Primary Examiner* — Ling Choi
*Assistant Examiner* — Gennadiy Mesh
(74) *Attorney, Agent, or Firm* — Mueting, Raasch & Gebhardt, P.A.

(57) ABSTRACT

Photodegradable polymers derived from biomass are provided, together with methods of making and methods of using the polymers. The photodegradable polymers can be derived from at least a first monomeric unit and a second monomeric unit and an optional third monomeric unit. The first monomeric unit is a dicarboxylic acid and includes a furan group and the second monomeric unit includes a nitrobenzyl group. Methods of recycling the polymers including irradiating the polymers to yield recycled monomers and oligomers are also disclosed.

12 Claims, 51 Drawing Sheets

(56) References Cited

PUBLICATIONS

Il'ichev et al., "Photochemical Reaction Mechanisms of 2-Nitrobenzyl Compounds: Methyl Ethers and Caged ATP," *J. Am. Chem. Soc.*, 2004; 126(14):4581-4595.

Jain et al., "Construction of a Photoactivated Insulin Depot," *Angew. Chem.*, 2013; 125(5):1444-1449; and *Angew. Chem., Int., Ed.*, 2013; 52(5):1404-1409.

Jiang et al., "Toward Photocontrolled Release Using Light-Dissociable Block Copolymer Micelles," *Macromolecules*, May 2006; 39(13):4633-4640.

Jiang et al., "A series of furan-aromatic polyesters synthesized via direct esterification method based on renewable resources," *J. Poly. Sci. A: Polymer Chem.*, 2012; 50(5):1026-1036.

Johnson et al., "Synthesis of Photocleavable Linear Macromonomers by ATRP and Star Macromonomers by a Tandem ATRP—Click Reaction: Precursors to Photodegradable Model Networks," *Macromolecules*, May 2007; 40:3589-3598.

Klán, et al., "Photoremovable Protecting Groups in Chemistry and Biology: Reaction Mechanisms and Efficacy," *Chem. Rev.*, 2012; 113:119-191.

Koopman et al., "Efficient whole-cell biotransformation of 5-(hydroxymethyl)furfural into FDCA, 2,5-furandicarboxylic acid," *Bioresour. Technol.*, 2010; 101:6291-6296.

Lewkowski, "Synthesis, chemistry and applications of 5-hydroxymethylfurfural and its derivatives," *ARKIVOC*, 2001; 17-54.

Lichtenthaler et al., "Carbohydrates as green raw materials for the chemical industry," *Comptes Rendus Chimie*, Feb. 2004; 7(2):65-90.

Lichtenthaler et al., *Chapter 1. Carbohydrate-based Product Lines: The Key Sugars of Biomass: Availability, Present Non-Food Uses and Potential Future Development Lines*, in Biorefineries-Industrial Processes and Products: Status Quo and Future Directions, Wiley, 2008.

Ma et al., "The copolymerization reactivity of diols with 2,5-furandicarboxylic acid for furan-based copolyester materials," *J. Mater. Chem.*, 2012; 22:3457-3461.

McNelis et al., "Synthetic and kinetic studies of substituent effects in the furan intramolecular Diels-Alder reaction," *Tetrahedron*, 1994; 50(23):6767-6782.

Moreau et al., "Recent Catalytic Advances in the Chemistry of Substituted Furans from Carbohydrates and in the Ensuing Polymers," *Topics in Catalysis*, Feb. 2004; 27(1):11-30.

National Science Foundation IIA-1355466 Grant Abstract. [retrieved on Nov. 26, 2014]. Retrieved from the Internet:<URL: http://www.nsf.gov/awardsearch/showAward?AWD_ID=1355466 &HistoricalAwards=false>; 2 pgs.

National Science Foundation ND-EPSCoR (EPS-0814442) Grant Abstract. [retrieved on Oct. 15, 2014]. Retrieved from the Internet:<URL:http://www.nsf.gov/awardsearch/
showAward?AWD_ID=0814442&HistoricalAwards=false>; 4 pgs.

NDSU, "New Plastic that Disappears When You Want It To," Newswise article ID: 626671, Released Nov. 24, 2014; [retrieved on Oct. 14, 2016]. Retrieved from the Internet:< http://www.newswise.com/articles/view/626671?print-article>; 3 pgs.

Pelliccioli et al., "Photoremovable protecting groups: reaction mechanisms and applications," *Photochem. Photobiol. Sci.*, 2002; 1(2):441-458.

Rajendran et al., "Degradation of bio-based oligomer/polymers from sustainable materials," Poster abstract POS12, *37th Meeting of the American Society for Photobiology*, San Diego, California, Jun. 14-19, 2014.

Rajendran et al., "Degradation of bio-based oligomer/polymers from sustainable materials," Poster presented Apr. 29, 2014 at the *ND EPSCoR Conference*, Grand Forks, ND, and presented Jun. 16, 2014, at the *37th Meeting of the American Society for Photobiology*, San Diego, California, Jun. 14-19, 2014.

Rajendran et al., "Programmed degradation of polymeric/ oligomeric materials derived from renewable bio-resources," *Angew. Chem.*, Jan. 2015; 54(4):1159-1163. Available online Nov. 2014.

Roman-Leshkov et al., "Production of dimethylfuran for liquid fuels from biomass-derived carbohydrates," *Nature*, Jun. 2007; 447:982-985.

Roper, "Future World Energy," [retrieved on Oct. 14, 2015]. Retrieved from the Internet: <URL:http://www.roperld.com/science/energyfuture.htm >; 13 pgs.

Rosatella et al., "5-Hydroxymethylfurfural (HMF) as a building block platform: Biological properties, synthesis and synthetic applications," *Green Chem.*, 2011; 13 :754-793.

Rundlöf et al., "Survey and qualification of internal standards for quantification by 1H NMR spectroscopy," *J. Pharm. Biomed. Anal.*, Sep. 2010; 52(5):645-651.

Sousa et al., "New copolyesters derived from terephthalic and 2,5-furandicarboxylic acids: A step forward in the development of biobased polyesters," *Polymer*, Jan. 2013; 54(2):513-519.

Sutton et al., "The hydrodeoxygenation of bioderived furans into alkanes," *Nat Chem*, 2013; 5:428-432.

Thananatthanachon et al., "Efficient Production of the Liquid Fuel 2,5-Dimethylfuran from Fructose Using Formic Acid as a Reagent," *Angew. Chem.*, Sep. 2010; 122 (37):6766-6768; and *Angew. Chem., Int., Ed.*, Sep. 2010, 49(37):6616-6618.

"Top Value Added Chemicals From Biomass Volume 1—Results of Screening for Potential Candidates From Sugars and Synthesis Gas," Aug. 2004, Pacific Northwest National Laboratory. 76 pages.

"Top Value Added Chemicals from Biomass, Volume II: Results of Screening for Potential Candidates from Biorefinery Lignin," Oct. 2007, Pacific Northwest National Laboratory. 87 pages.

Tong et al., *Applied Catalysis A: General*, Sep. 2010; 385(1-2):1-13.

van Putten et al., "Hydroxymethylfurfural, A Versatile Platform Chemical Made from Renewable Resources," *Chem. Rev.*, Feb. 2013; 113(3):1499-1597.

Webb et al., "Plastic Degradation and Its Environmental Implications with Special Reference to Poly(ethylene terephthalate)," *Polymers*, 2013; 5:1-18.

Yao et al., "Controlled Polymerization of Next-Generation Renewable Monomers and Beyond," *Macromolecules*, 2013; 46(5):1689-1712.

Yoon et al., "Phenyl-, pyrrole-, and furan-containing diametrically strapped calix[4]pyrroles. An experimental and theoretical study of hydrogen bonding effects in chloride anion recognition," *Angew Chem. Int. Ed.*, 2008; 47:5038-5042.

Zakrzewska et al., "Ionic Liquid-Mediated Formation of 5-Hydroxymethylfurfural—A Promising Biomass-Derived Building Block," *Chem. Rev.* 2011; 111:397-417.

Zhao et al., "Metal Chlorides in Ionic Liquid Solvents Convert Sugars to 5-Hydroxymethylfurfural," *Science*, Jun. 2007; 316(5831): 1597-1600.

Zhao et al., "o-Nitrobenzyl Alcohol Derivatives: Opportunities in Polymer and Materials Science," *Macromolecules*, 2012; 45(4):1723-1736.

$^1$H-NMR (400 MHz, CDCl$_3$, δ ppm): 3.27 (bs, 1H), 4.68 (s, 2H), 6.49 (d, 1H, $J$ = 3.5 Hz), 7.19 (d, 1H, $J$ = 3.5 Hz) and 9.53 (s, 1H).

$^{13}$C-NMR (100 MHz, CDCl$_3$, δ ppm): 57.6, 110.0, 123.3, 152.3, 161.0 and 177.9.

\* = solvent $^1$H NMR (500 MHz, DMSO-d$_6$, δ ppm):7.28 (s, 2H).

$^{13}$C NMR (125 MHz, DMSO-d$_6$, δ ppm): 119.0, 147.6 and 159.6.

HRMS [ESI-MS] m/z ([M-OH]):
Calculated :139.0026
Observed :139.0018
|Δm| : 5.7 ppm IR (KBr) cm$^{-1}$: 3026 (ν$_{OH}$), 1688 (ν$_{C=O}$), 1221 (ν$_{C-O}$).

* = solvent

¹H NMR (400 MHz, CDCl₃, δ ppm): 5.36 (s, 2H), 6.65 (d, 1H, $J$ = 4 Hz), 7.21 (d, 1H, $J$ = 4 Hz), 7.40-7.44 (m, 2H), 7.53-7.57 (m, 1H), 8.02-8.05 (m, 2H) and 9.63 (s, 1H).

$^{13}$C NMR (100 MHz, CDCl$_3$, δ ppm): 58.4, 112.9, 121.9, 128.6, 129.4, 130.0, 133.6, 153.0, 155.7, 166.0 and 178.0.

HRMS [ESI-MS] m/z([M+Na])
Calculated  :253.0471
Observed    :253.0486
|Δm|        : 5.9 ppm ¹H NMR (500 MHz, CDCl₃, δ ppm): 1.03 (d, 18H, J = 7.15 Hz), 1.09-1.16 (m, 3H), 4.80 (s, 2H), 6.47 (d, 1H, J = 3.6Hz), 7.18 (d, 1H, J = 3.6 Hz) and 9.54 (s, 1H).

$^{13}$C NMR (125 MHz, CDCl$_3$, δ ppm): 12.1, 18.0, 59.3, 109.2, 122.7, 152.2, 161.9 and 177.6.

HRMS [ESI-MS] m/z([M+Na])
Calculated : 305.1543
Observed : 305.1553
|Δm| : 3.3 ppm \* = solvent ¹H NMR (500 MHz, DMSO-d₆, δ ppm): 5.33 (s, 2H), 6.64 (d, 1H, J = 5 Hz), 6.91 (d, 1H, J = 5 Hz), 7.52 (t, 2H, J = 10 Hz), 7.66 (t, 1H, J = 10 Hz) and 7.96 (d, 2H, J = 10 Hz).

* = solvent

¹³C NMR (125 MHz, DMSO-d₆, δ ppm): 59.1, 113.0, 115.7, 129.6, 129.8, 129.9, 134.2, 150.5, 151.3, 161.2 and 166.0.

HRMS [ESI-MS] m/z([M+Na])
Calculated :269.0420
Observed :269.0430
|Δm| : 3.7 ppm

* = solvent $^1$H NMR (500 MHz, CDCl$_3$, δ ppm): 1.09 (d, 18H, $J$ = 5 Hz), 1.14-1.21 (m, 3H), 4.85 (s, 2H), 6.47 (d, 1H, $J$ = 5 Hz) and 7.30 (d, 1H, $J$ = 5Hz).

¹H NMR (500 MHz, DMSO-d₆, δ ppm): 4.91 (s (broad, H₂O + COO*H*), 7.80 (t, 1H, *J* = 10 Hz) and 8.18 (d, 2H, *J* = 10 Hz).

∗ = solvent $^{13}$C NMR (125 MHz, DMSO-d$_6$, δ ppm): 125.4, 131.8, 135.2, 149.4 and 164.8.

¹H NMR (500 MHz, DMSO-d₆, δ ppm): 4.53 (d, 4H, $J$ = 5 Hz), 5.50 (t, 2H, $J$ = 5 Hz) and 7.52-7.57 (m, 3H).

$^{13}$C NMR (125 MHz, DMSO-d$_6$, δ ppm): 64.6, 132.9, 136.2, 139.7 and 152.8.

¹H NMR (400 MHz, CDCl₃, δ ppm): 5.36 (s, 2H), 5.47 (s, 2H), 6.61 (d, 1H, J = 3.45 Hz), 7.19 (d, 1H, J = 5 Hz), 7.45 (t, 2H, J = 5 Hz), 7.54-7.61 (m, 3H) and 8.06 (d, 2H, J = 5 Hz).

$^{13}$C NMR (100 MHz, CDCl$_3$, δ ppm): 58.4, 62.6, 94.6, 112.6, 119.9, 128.6, 129.5, 129.6, 130.0, 130.3, 131.5, 133.5, 144.0, 154.5, 157.8 and 166.1.

* = solvent

HRMS [ESI-MS] *m/z*([M+Na])
Calculated :662.1269
Observed :662.1279
|Δm| :1.5 ppm FT-IR (KBr) cm$^{-1}$: 1745 ($v_{CO}$, 1532 ($_{asym}v_{NO2}$), 1364 ($_{sym}v_{NO2}$)

¹H NMR (500 MHz, CDCl₃, δ ppm): 1.08 (d, 36H, $J$ = 10 Hz), 1.12-1.18 (m, 6H), 4.81 (s, 4H), 5.45 (s, 4H), 6.41 (d, 2H, $J$ = 5 Hz), 7.17 (d, 2H, $J$ = 5 Hz) and 7.53-7.58 (m, 3H).

¹³C NMR (125 MHz, CDCl₃, δ ppm): 12.1, 18.1, 59.2, 62.3, 108.7, 120.2, 129.7, 130.1, 131.5, 142.7, 148.9, 158.1 and 160.4.

¹H NMR (400 MHz, CDCl₃, δ ppm): 1.09 (d, 18H, *J* = 4 Hz), 1.13-1.20 (m, 3H), 2.25, (s (broad), 1H), 4.77 (s, 2H), 4.83 (s, 2H), 5.46 (s, 2H), 6.43 (d, 1H, *J* = 4 Hz), 7.18 (d, 1H, *J* = 4 Hz), 7.56-7.60 (m, 2H) and 7.63-7.65 (m, 1H).

¹³C NMR (100 MHz, CDCl₃, δ ppm): 11.9, 17.8, 59.0, 61.5, 62.2, 108.5, 119.9, 129.3, 129.4, 129.8, 131.6, 134.2, 142.5, 148.5, 157.9 and 160.2.

HRMS [ESI-MS] m/z([M+Na])
Calculated   :486.1919
Observed    :486.1913
|Δm|        :1.2 ppm $^1$H NMR (400 MHz, CDCl$_3$, δ ppm): 1.09 (d, 18H, $J$ = 4 Hz), 1.20-1.13 (m, 3H), 4.83 (s, 2H), 5.47 (s, 2H), 5.51 (s, 2H), 6.43 (d, 1H, $J$ = 4 Hz), 7.19 (d, 1H, $J$ = 4 Hz), 7.45-7.49 (m, 2H), 7.55-7.63 (m, 4H) and 8.04-8.06 (m, 2H).

∗ = solvent $^{13}$C NMR (100 MHz, CDCl$_3$, δ ppm): 11.9, 17.9, 59.0, 62.1, 62.6, 108.5, 120.0, 128.5, 129.3, 129.5, 129.7, 129.8, 129.9, 130.0, 131.2, 133.4, 142.5, 148.9, 157.9, 160.2 and 165.8.

* = solvent

HRMS [ESI-MS] m/z([M+Na])
Calculated   :590.2181
Observed    :590.2184
|Δm|        :0.5 ppm ¹H NMR (400 MHz, DMSO-d₆, δ ppm): 5.29, (s, 0.47 H), 5.48 (s, 4H), 7.41 (s, 2H), 7.54 (s, 0.23 H), 7.64 (d, 0.39 H, J = 8 Hz) and 7.73-7.77 (m, 3H).

$^{13}$C NMR (100 MHz, DMSO-d$_6$, δ ppm): 63.2, 120.1, 129.1, 131.2, 132.5, 146.1, 148.4 and 157.0.

$^1$H NMR (500 MHz, DMSO-d$_6$, δ ppm): 3.66 (s (broad), 4H), 4.27 (s (broad), 4H), 4.59 (s (broad), 28H), 4.91 (s (broad), 2H), 5.45 (s (broad), 4H), 7.40 (s (broad), 15H) and 7.75 (s (broad), 3H).

¹³C NMR (125 MHz, DMSO-d₆, δ ppm): 64.2, 68.5, 72.4, 124.9, 134.1, 151.3 and 162.5.
Apart from the above major peaks there are several peaks, which are little above base line:
68.1, 124.5, 125.1, 136.2, 137.4, 150.8, 151.1, 151.6, 151.8, 162.0, 162.5, 162.6 and 162.8.
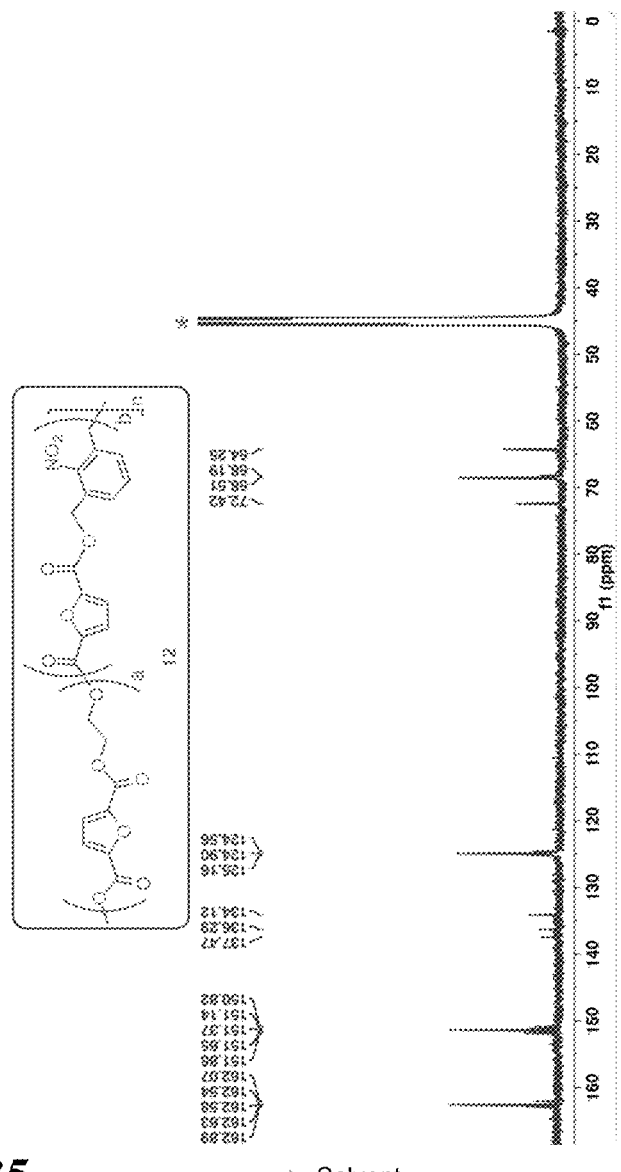
Figure 35.   *=Solvent

* = Internal standard-triphenyl methane

* = Internal standard-triphenyl methane

* = Internal standard-triphenyl methane

Figure 48a.  Figure 48b.
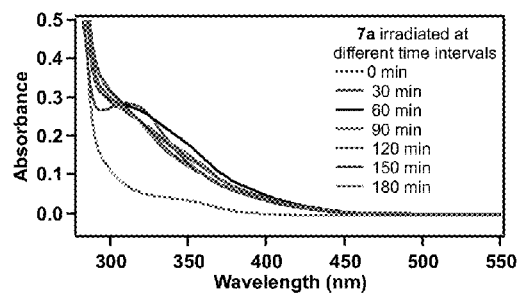
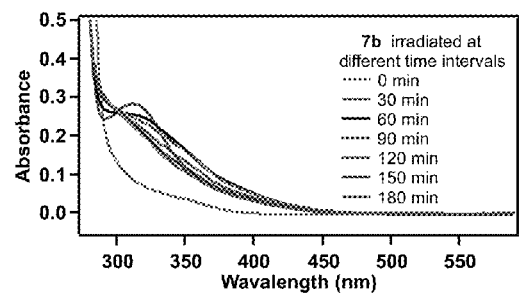
Figure 49.
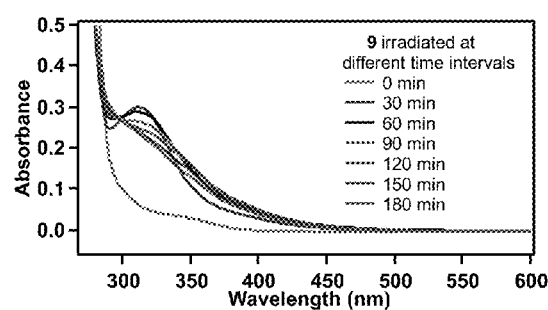

PROGRAMMED DEGRADATION OF POLYMERS DERIVED FROM BIOMASS

PRIORITY

This application claims priority to U.S. Provisional Application Ser. No. 62/064,197 filed Oct. 15, 2014, entitled "Programmed Degradation of Polymers Derived from Biomass," and U.S. Provisional Application Ser. No. 62/074,379 filed Nov. 3, 2014, entitled "Programmed Degradation of Polymers Derived from Biomass," and, the disclosures of both of which are incorporated in their entirety herein by reference thereto.

STATEMENT OF GOVERNMENT RIGHTS

This invention was made with government support under ND-EPSCoR (EPS-0814442) awarded by the National Science Foundation and under IIA-1355466 awarded by the National Science Foundation. The government has certain rights in the invention.

BACKGROUND

In the past two decades considerable efforts have been made to convert biomass especially carbohydrates into value added chemicals and as suitable alternates for constantly depleting fossil fuels. Biomass is inexpensive, abundant and more importantly renewable. There are a plethora of reports on conversion of carbohydrates, glucose or fructose into a number of industrially important intermediates such as dimethyl furan, γ-valerolactone, ethyl levulinate, caprolactam, caprolactone, 1,6-hexanediol, adipic acid, 2,5-bishydroxymethyl furan and 2,5-furandicarboxylic acid (FDCA).

The common key chemical for accessing the chemicals mentioned above is 5-hydroxymethylfurfural (HMF). FDCA, an oxidation product of HMF, was identified as an important building block for polymer synthesis. Due to their industrial importance, both HMF and FDCA are listed among the top 14 bio-based chemicals by U. S. Department of Energy (DOE). FDCA could possibly replace terephthalic acid in polyethylene terephthalate (PET), a polyester prepared in tons every year and FDCA-glycol polymer has properties similar to PET. Though synthetic polymers play vital roles in daily life, their non/poor-degradability increases concerns regarding their impact on the environment (as they are mostly disposed in landfills). In addition, building blocks for polymers are mainly derived from fossil fuels. Great demand with diminishing fossil fuels necessitates finding alternate sustainable sources for building polymeric materials.

SUMMARY

Novel photodegradable polymers derived from biomass are provided, together with methods of making and methods of using said polymers. In one aspect, the photodegradable polymer contains at least one first monomeric unit comprising a monomer obtained from biomass and at least one second monomeric unit comprising a phototrigger. Optionally, the photodegradable polymer can contain a plurality of first monomeric units, each one obtained from biomass. Optionally, the photodegradable polymer can contain a plurality of phototrigger monomeric units, which can be selected to photocleave at the same or different wavelengths. Optionally, the photodegradable polymer further includes at least one third monomeric unit, wherein the third monomeric unit is obtained from a petroleum product or is chemically or enzymatically synthesized. The optional third monomeric unit can be, for example, a hydrophilic monomer, such as an alkylene glycol. In some embodiments, the photodegradable polymer can contain a greater number of first monomeric units than second monomeric units. In some embodiments of the photodegradable polymer containing one or more optional third monomeric units, the polymer can contain greater numbers of first and/or third monomeric units compared to the number of second monomeric units.

Novel methods of making and using the photodegradable polymers, as well as methods for making and using or reusing photodegradation products of the photodegradable polymers, are also provided. In one aspect, the method for making the photodegradable polymer includes reacting a bifunctionalized first monomeric unit with a bifunctionalized second monomeric unit under conditions and for a time to yield the photodegradable polymer. Optionally, the method can further include reacting a bifunctionalized third monomeric unit with said first and second monomeric units to yield the photodegradable polymer.

In another aspect, a method is provided for recycling a photodegradable polymer. The method can include photodegrading the photodegradable polymer to yield one or more degradation products that include one or more recycled monomers or oligomers. An exemplary method for degrading the photodegradable polymer includes exposing the polymer to light having a wavelength selected so as to cause photocleavage of the polymer, under conditions and for a time sufficient to yield the recycled monomers or oligomers.

Optionally, at least one of the recycled monomers or oligomers can be used to synthesize a polymer comprising the recycled monomer or oligomer. A recycled monomer or oligomer of interest can be optionally isolated, separated or purified from other products of photodegradation of the polymer. The recycled monomer or oligomer can optionally be stored and/or transported prior to being used in further methods for polymer synthesis.

Polymers and oligomers that contain at least one recycled monomer or oligomer as described herein are also encompassed by the invention.

BRIEF DESCRIPTION OF THE FIGURES

FIG. 6 is a $^1$H NMR spectrum (400 MHz, CDCl$_3$, δ ppm) of compound 4a.

FIG. 7 is a $^{13}$C NMR spectrum (100 MHz, CDCl$_3$, δ ppm) and ESI-MS (electrospray ionization-mass spectroscopy) data of compound 4a.

FIG. 10 is a $^1$H NMR spectrum (500 MHz, DMSO-d$_6$, δ ppm) of compound 5a.

FIG. 11 is a $^{13}$C NMR spectrum (125 MHz, DMSO-d$_6$, δ ppm) and ESI-MS data of compound 5a.

FIG. 18 is a $^1$H NMR spectrum (400 MHz, CDCl$_3$, δ ppm) of compound 7a.

FIG. 19 is a $^{13}$C NMR spectrum (100 MHz, CDCl$_3$, δ ppm) of compound 7a.

FIG. 20 is ESI-MS and Fourier transform-infrared (FT-IR) in KBR data of compound 7a.

FIG. 35 is a $^{13}$C NMR spectrum (125 MHz, DMSO-d$_6$, δ ppm) of compound 12.

FIGS. 48a and 48b show ultraviolet-visible (UV-VIS) spectra of $10^{-4}$ M solution of ester 7a (FIG. 48a) and ester 7b (FIG. 48b) in THF-H$_2$O (4:1) at 0 minutes (bottom line in both), 30 min, 60 min, 90 min, 120 min, 150 min, and 180 min of irradiation.

FIG. 49 shows UV-VIS spectra of $10^{-4}$ M solution of ester 9 in THF-H$_2$O (4:1) at 0 minutes (bottom line in both), 30 min, 60 min, 90 min, 120 min, 150 min, and 180 min of irradiation.

DETAILED DESCRIPTION

Figure 1:
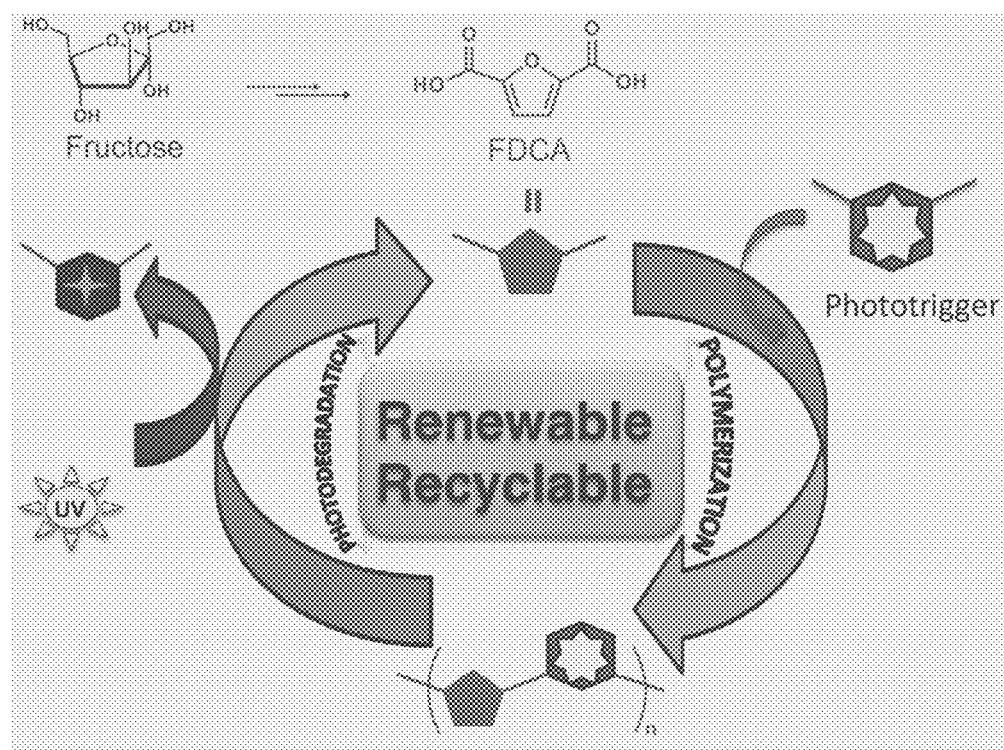
FIG. 1 is a schematic illustration of the concept to programmed photodegradation of bio-based oligomers/polymers derived from 2,5-furandicarboxylic acid (FDCA), as an example.

Disclosed herein are polymers characterized by higher degrees of degradability and sustainability, that include building blocks from renewable resources with built-in photocleavable unit(s) to obtain photodegradable polymers that can be pre-programmed for degradation with light. A specific, illustrative example of such a polymer includes a FDCA derived polymer that features a nitrobenzyl chromophore to trigger photodegradation upon shining light. FIG. 1 illustrates the concept of photodegradation of such a polymer.

The invention broadly provides novel photodegradable polymers derived from biomass, together with methods of making and methods of using said polymers. It should be understood that the term "polymer" is inclusive of compounds known as oligomers, polymers, homopolymers, heteropolymers and copolymers, without limitation. The polymers of the invention include at least one first monomeric unit derived from biomass, and at least one second monomeric unit that constitutes a phototrigger.

In one aspect, the photodegradable polymer contains at least one first monomeric unit comprising a monomer obtained from biomass and at least one second monomeric unit comprising a phototrigger.

Disclosed polymers include at least one first monomeric unit comprising a monomer obtained from biomass. It should be understood that the photocleavable polymers of the invention can contain one, two, three, four, five, six, seven, eight, nine, ten or more different first monomeric units derived from biomass. In some embodiments, one or more of the first monomers can be derived from biomass such as lignin, cellulose, or hemicellulose.

Lignins

Illustrative first monomeric units include those that are specifically obtained from lignins. Lignin is a polymer and depolymerization thereof yields a variety of substituted phenols, of which p-coumaryl alcohol, coniferyl alcohol and sinapyl alcohol are the most abundant. Important, well-known phenolic derivatives of these compounds include vanillin, eugenol, iso-vanillin, iso-eugenol, caffeic acid and syringeugenol. In addition to the phenolic hydroxyl, these lignin derived monomers advantageously contain an additional functionality such as an aldehyde, an allyl or isoallyl. Other lignin-derived monomers that can serve as starting materials include creosol and guaiacol. Some lignin monomers are shown below:

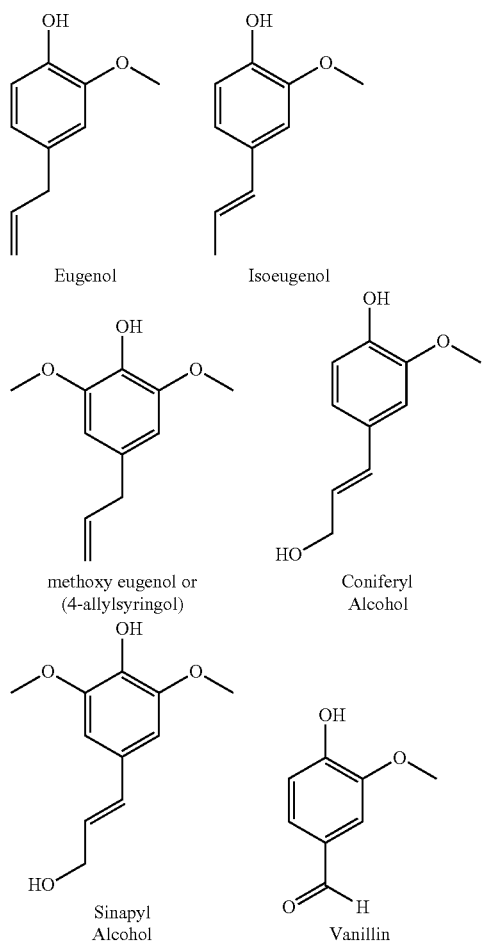

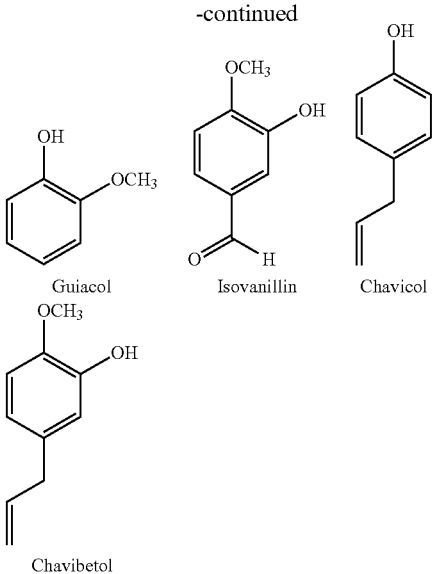

Illustrative starting materials for the synthesis of disclosed monomers can include not only phenols but also guaiacols, syringols, eugenols, catechols, their oxidized products, including vanillin, vanillic acid, syringaldehyde, and their easily-derived hydrocarbons, including benzene, toluene, xylene, styrene, biphenyls and cyclohexane. See "Top Value Added Chemicals from Biomass, Volume II: Results of Screening for Potential Candidates from Biorefinery Lignin," October 2007, Pacific Northwest National Laboratory for processes suitable for obtaining phenolic starting materials from lignin, and for additional examples of starting materials.

Illustrative bifunctional lignin derived monomers that can be utilized as first monomeric units include, without limitation, diacids, e.g., diols or dialdehydes which can contain 0, 1 or 2 methoxy groups depending on the starting material used. Examples of first monomeric units that contain 0 or 1 methoxy groups and alcohol, acid, or aldehyde functionalities include, without limitation:

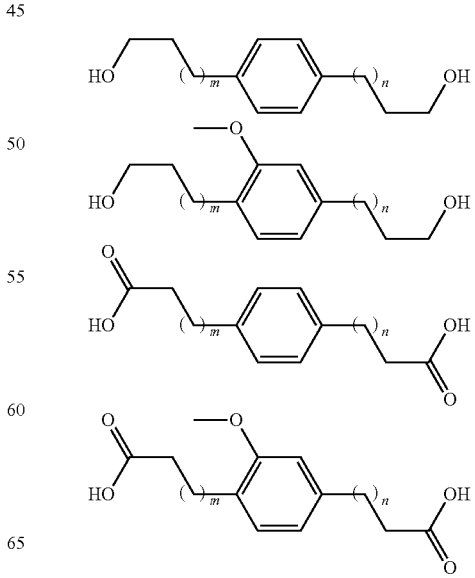

-continued

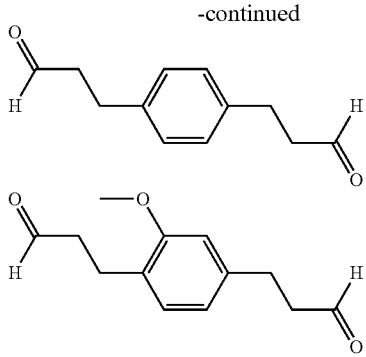

wherein m=0, 1, 2, 3, 4, 5, 6, 7, 8, 9, 10, 11, 12, 13, 14, 15, 16, 17, 18, 19, 20, or more, up to about 50; and n=0, 1, 2, 3, 4, 5, 6, 7, 8, 9, 10, 11, 12, 13, 14, 15, 16, 17, 18, 19, 20, or more, up to about 50; and where m=n or m ≠ n.

Dialdehyde monomers may be advantageously utilized herein as first monomeric units and illustrative chemistries for obtaining such monomers are described in the examples, below. Dialdehydes may be useful intermediates in that they can be readily converted to other functional groups, optionally including the addition of a hydrocarbon extension.

An example of a dialdehyde conversion to a diacid and then to a diol is as follows:

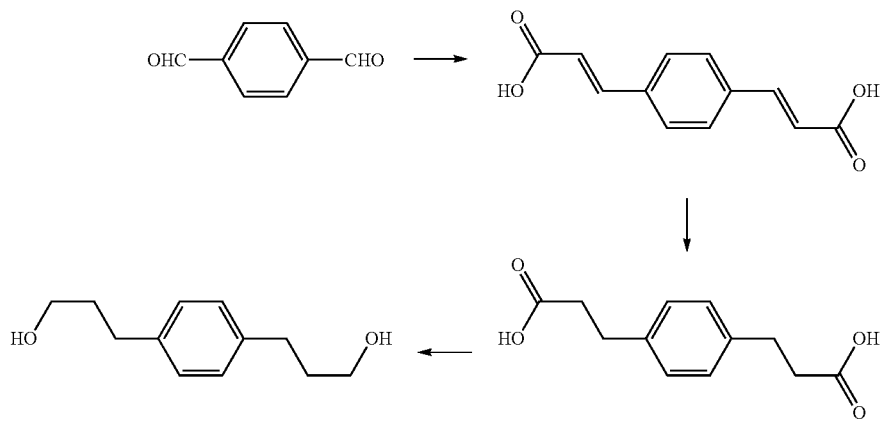

In general, aldehydes can be readily converted to another functional group of interest to form compounds, including for example disclosed compounds.

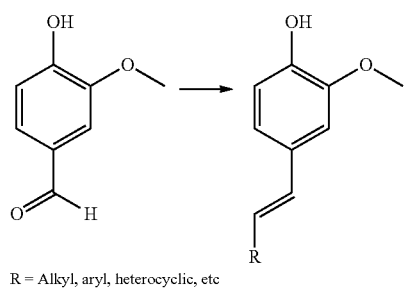

R = Alkyl, aryl, heterocyclic, etc

In some particular examples, compounds of formulae I and IV can be derived from lignins and utilized as first monomeric units in disclosed polymers.

Some embodiments include compounds of formula I:

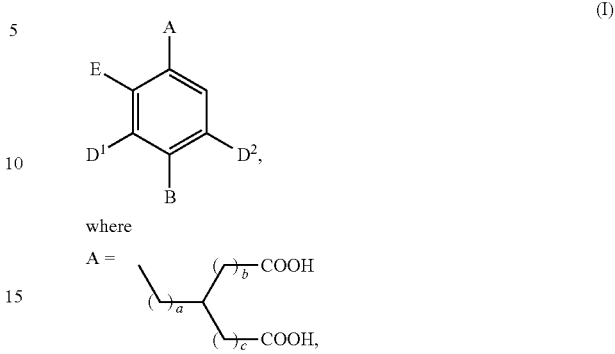

where where a is 1, 2 or 3; and b and c are independently 0, 1, 2, or 3; B is A, —OH, or —OR where R is —$CH_3$, —$CH_2CH_3$, $CH_2CH_2CH_3$, $CHCH_2$, $CHCHCH_3$, or $CH_2CHCH_2$; $D^1$ and $D^2$ are independently H, —OH, or —OR where R is —$CH_3$, —$CH_2CH_3$, $CH_2CH_2CH_3$, $CHCH_2$, $CHCHCH_3$, or $CH_2CHCH_2$; and E is H or together with $D^1$ and the phenyl ring attached thereto forms a naphthalene ring, with the proviso that if a is 1, b is 1, c is 0, $D^2$ is —$OCH_3$, B is —OH, then $D^1$ is not H and the proviso that the compound of formula I is bifunctional, e.g. a diacid.

In some illustrative embodiments, both A and B are

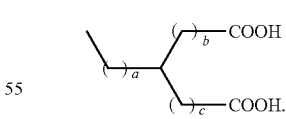

In some illustrative embodiments both A and B have the same structure. In some illustrative embodiments, $D^1$ can be H, or —OH. In some illustrative embodiments, $D^1$ can be H. In some illustrative embodiments, $D^1$ together with E and the phenyl ring attached thereto form a naphthalene ring.

In some illustrative embodiments, compounds of formula I can include, for example

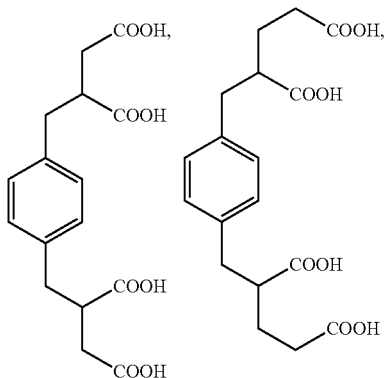

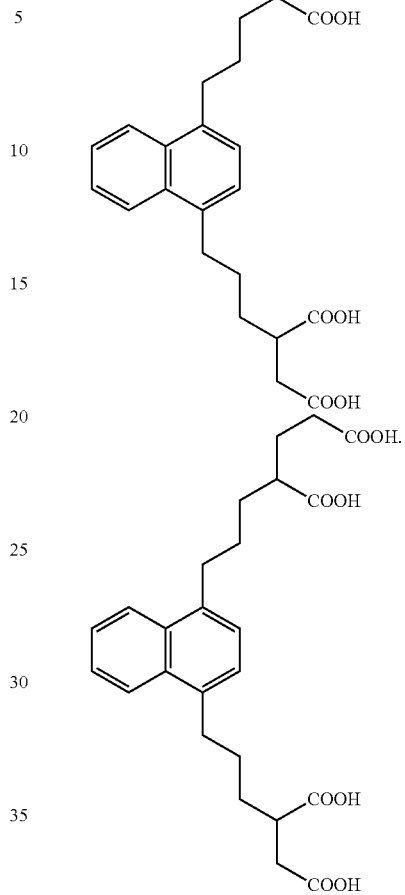

While in some other illustrative embodiments, compounds of formula I can include, for example

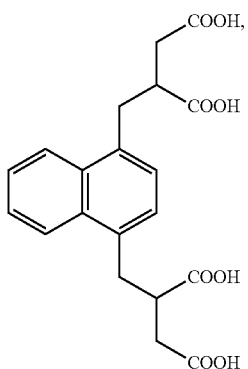

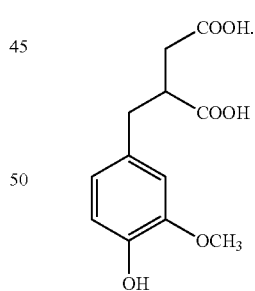

In some illustrative embodiments, a compound having the following formula can be utilized:

In some embodiments, compounds of formula I can be derived from lignins. In some embodiments, compounds of formula I can be derived from lignins that are depolymerized. In some such embodiments, depolymerized lignins include phenolic hydroxyl groups, which can be converted to leaving groups. In some embodiments depolymerized lignins can be modified by extending the carbon chain, for example using Kumada coupling. In some embodiments, compounds of formula I can be derived from eugenol, isoeugenol, guiacol, vanillin, isovanillin, chavicol, chavibetol, or combinations thereof.

In some embodiments, compounds of formula I, as first monomeric units can be polymerized at least with second monomeric units. In some embodiments polymerization of compounds of formula I can be accomplished using free radical polymerization.

Some embodiments include compounds of formula IV as first monomeric units:

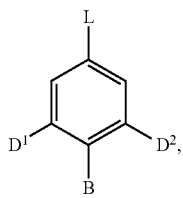

(IV)

where L is —(CH$_2$)$_h$COOH, where h is 4, 5, or 6,

B is —OH, or —OR where R is —CH$_3$, —CH$_2$CH$_3$, CH$_2$CH$_2$CH$_3$, CHCH$_2$, CHCHCH$_3$, or CH$_2$CHCH$_2$;

D$^1$ and D$^2$ are independently H, —OH, or —OR where R is —CH$_3$, —CH$_2$CH$_3$, CH$_2$CH$_2$CH$_3$, CHCH$_2$, CHCHCH$_3$, or CH$_2$CHCH$_2$, with the proviso that the compound of formula IV is bifunctional, e.g., a diacid.

In some illustrative embodiments, D$^1$ can be H, or —OH. In some illustrative embodiments, D$^1$ can be H.

In some embodiments, first monomeric units can include illustrative structures and/or compounds seen in compounds 1 to 13b below, which may be derived from lignin compounds.

(Cmpd. 1)

(Cmpd. 2)

(Cmpd. 3)

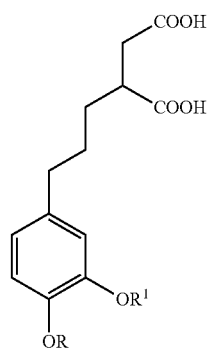

(Cmpd. 4)

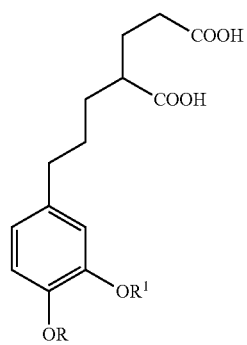

(Cmpd. 5)

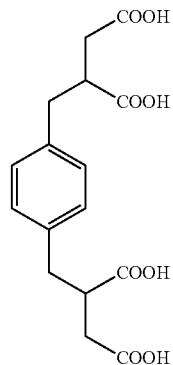

(Cmpd. 6)

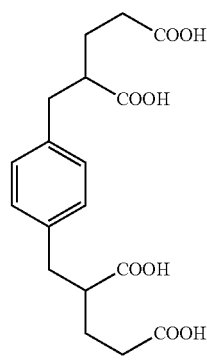

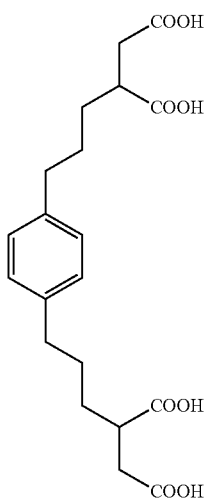
(Cmpd. 7)

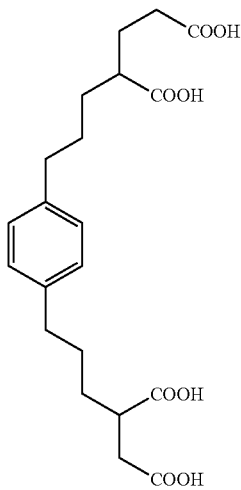
(Cmpd. 8)

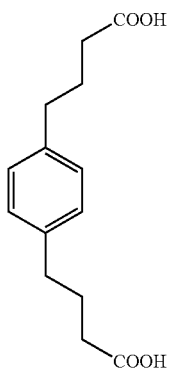
(Cmpd. 12)

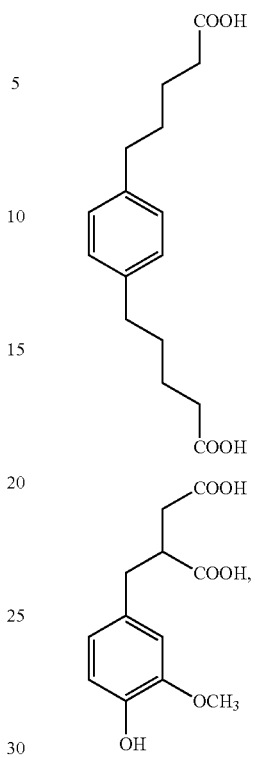
(Cmpd. 13)

(Cmpd. 13b)

where both R and R$^1$ can be —CH$_3$, —CH$_2$CH$_3$, CH$_2$CH$_2$CH$_3$, CHCH$_2$, CHCHCH$_3$, or CH$_2$CHCH$_2$ where appropriate.

In some embodiments, first monomeric units can include illustrative structures seen in compounds 15 to 16 below, which may be derived from lignin compounds.

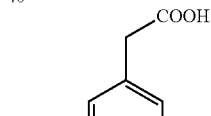
(Cmpd. 15)

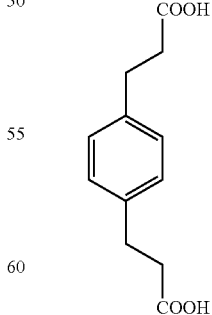
(Cmpd. 16)

Some illustrative first monomeric units can be derived from cellulose or hemicellulose for example.

With respect to biomass derived from cellulose and hemicellulose, the present disclosure provides methods for the conversion of fructose, which is readily available from cellulose by degradation and isomerization, to a wide variety of monomers for polymer synthesis with novel properties. 5-Hydroxymethylfurfural (HMF) is a primary product of fructose dehydration and can serve as the starting material for the preparation of many of the furan-based compounds described herein. HMF can be converted to other important intermediates, such as 2,5-furandicarboxylic acid (FDCA), 2,5-diformylfuran, and 2,5-furylbis(propenoic acid), which can be utilized directly or can serve as further intermediates for the synthesis of additional monomers with the potential utility to replace terephthalic acid and other petroleum-derived monomers.

Examples of first monomeric units that can be derived from HMF can include those seen below:

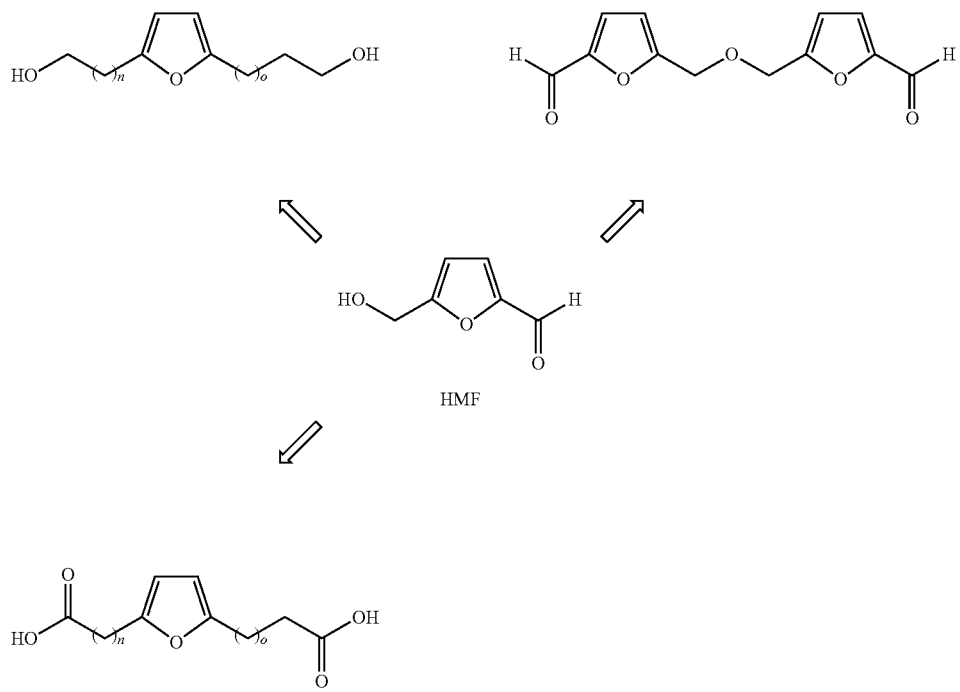

where n and o are independently selected from 0, 1, 2, 3, 4, 5, 6, 7, 8, 9, 10, up to 20, up to 30, up to 40 up to 50, or even higher.

Additionally, HMF and its 2,5-substituted derivatives can be reacted in a Diels-Alder reaction, followed by a deoxygenation/aromatization step to yield bicyclic naphthalene derivatives. A wide variety of symmetric and asymmetric naphthalene derivatives can be generated, since variation is introduced via the particular HMF derivative selected as a starting material.

Examples of naphthalene containing compounds that can be utilized as first monomeric units derived from HMF or its derivatives can include:

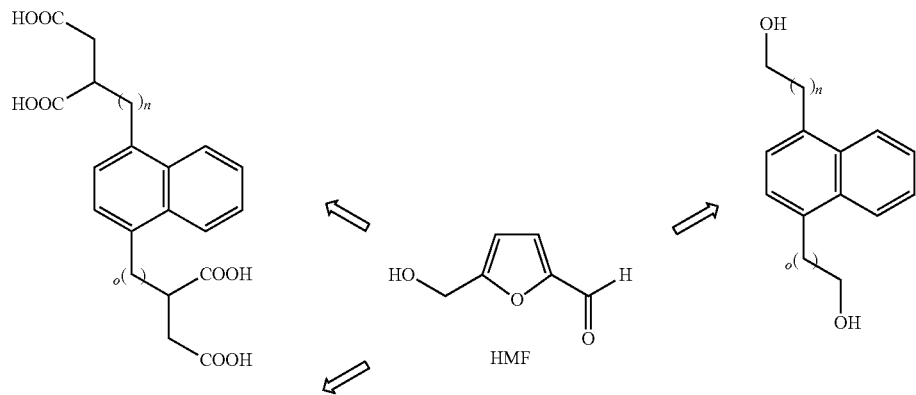

-continued

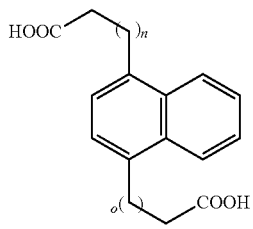

where n and o are independently selected from 0, 1, 2, 3, 4, 5, 6, 7, 8, 9, 10, up to 20, up to 30, up to 40 up to 50, or even higher.

Dimers of HMF and its 2,5-substituted derivatives, formed via condensation, can also serve as starting materials for first monomeric units.

Examples of first monomeric units that may be derived from dimers of HMF or its derivatives include:

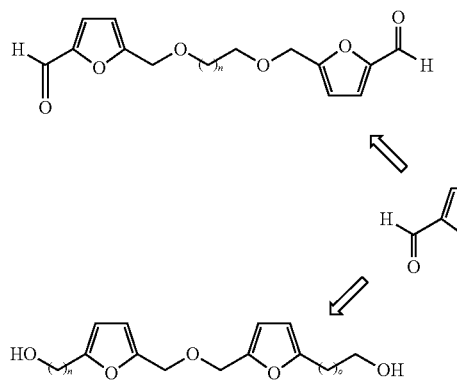

Cirsiumaldehyde where n and o are independently selected from 0, 1, 2, 3, 4, 5, 6, 7, 8, 9, 10, up to 20, up to 30, up to 40 up to 50, or even higher.

Compounds of formulae II, III, and V can be derived from cellulose, hemicellulose, or combinations thereof, through HMF, for example and be used as first monomeric units.

Some embodiments include compounds of formula II as first monomeric units:

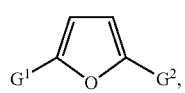

(II)

where $G^1$ and $G^2$ are independently

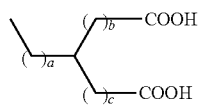

where a is 1, 2 or 3; and b and c are independently 0, 1, 2, or 3,
—$(CH_2)_d$OH where d is 1, 2, 3, 4 or 5, or
—$(CH_2)_e$COOH where e is 0, 1, 2, 3, 4 or 5.

In some illustrative embodiments, compounds of formula II include those in which both $G^1$ and $G^2$ are

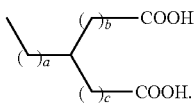

In some such illustrative embodiments, compounds of formula II include those in which at least one of b and c in both $G^1$ and $G^2$ are 0. In some such illustrative embodiments, compounds of formula II include those in which only one of b and c in both $G^1$ and $G^2$ are 0. In some such illustrative embodiments, compounds of formula II include those in which the structure of $G^1$ and $G^2$ are the same. In some embodiments, if both $G^1$ and $G^2$ are —$(CH_2)_e$COOH, and one of e is 2 then the other e is not 0 or 2.

In some illustrative embodiments, compounds of formula II can include, for example

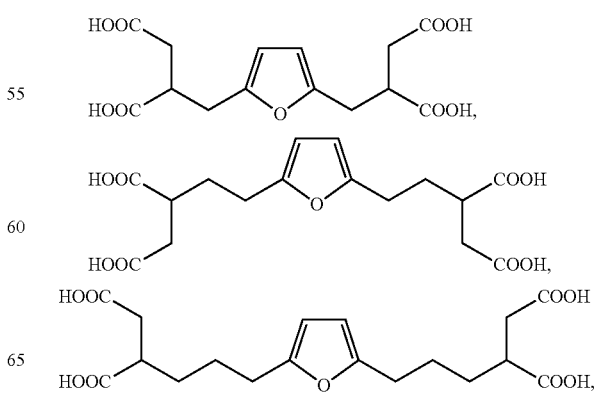

-continued

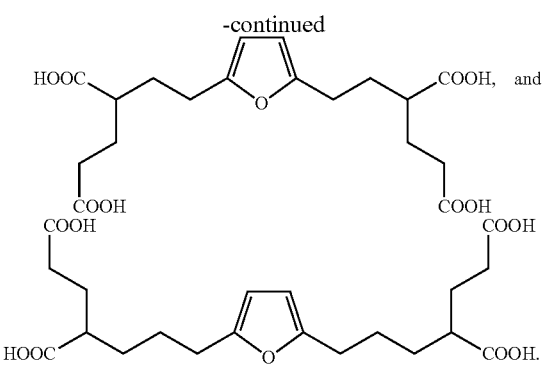

In some illustrative embodiments, compounds of formula II include those in which one of $G^1$ and $G^2$ is —$(CH_2)_d$OH. In some such illustrative embodiments, compounds of formula II include those in which the other of $G^1$ and $G^2$ is

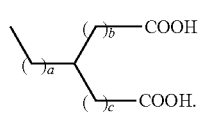

In some illustrative embodiments, compounds of formula II can include, for example

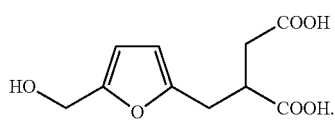 [SMILES: O=C(O)CC(Cc1ccc(CO)o1)C(=O)O]

In some illustrative embodiments, compounds of formula II include those in which both $G^1$ and $G^2$ are —$(CH_2)_e$COOH. In some illustrative embodiments, compounds of formula II can include, for example

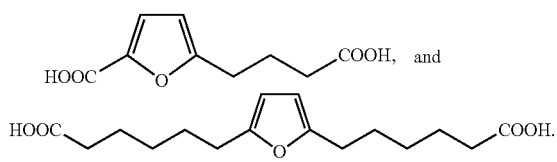

In some embodiments, compounds of formula II can be derived from cellulose, hemicellulose, or combinations thereof and used as first monomeric units. In some embodiments, compounds of formula II can be derived from fructose from cellulose, hemicellulose or a combination thereof and used as first monomeric units. In some such embodiments, the fructose can be dehydrated to form 5-hydroxymethylfurfural (HMF).

In some embodiments, compounds of formula II, as first monomeric units can be polymerized with at least second monomeric units. In some embodiments polymerization of compounds of formula II can be accomplished using free radical polymerization.

Some embodiments include compounds of formula III as first monomeric units:

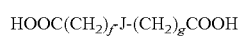

HOOC(CH$_2$)$_f$-J-(CH$_2$)$_g$COOH    (III), where J is selected from:

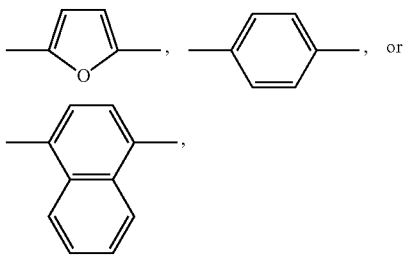

and f is 0, 1 2, 3, 4 or 5 and g is 0, 1, 2, 3, 4 or 5.

In some illustrative embodiments, compounds of formula III can include those in which J is

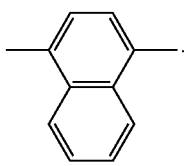

In some such illustrative embodiments, compounds of formula III can include those in which f and g are the same.

In some illustrative embodiments, compounds of formula III can include, for example

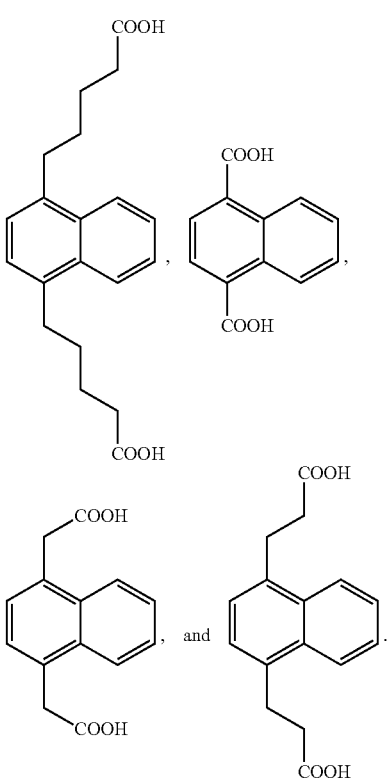

In some illustrative embodiments, compounds of formula III can include those in which J is

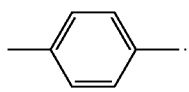

In some such illustrative embodiments, compounds of formula III can include those in which f and g are the same. In some such illustrative embodiments, compounds of formula III can include those in which f and g are 3 or 4.

In some illustrative embodiments, compounds of formula III can include, for example

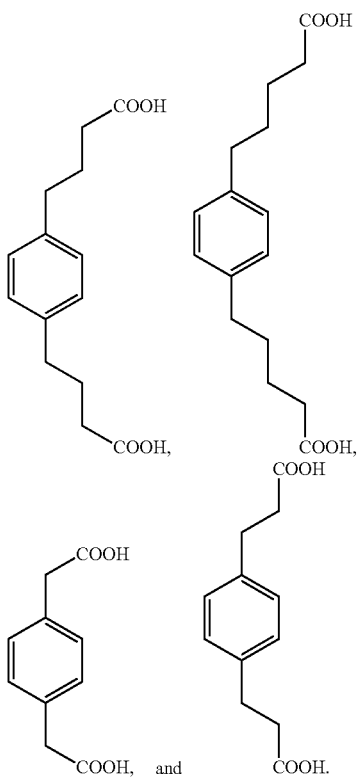

In some illustrative embodiments, compounds of formula III can include those in which J is

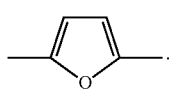

In some such illustrative embodiments, compounds of formula III can include those in which f and g are the same. In some illustrative embodiments, compounds of formula II can include, for example

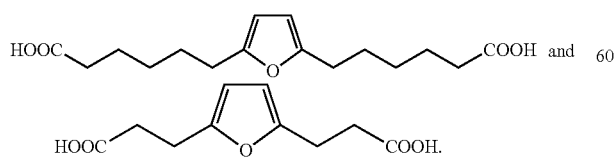

In some such illustrative embodiments, compounds of formula III can include those in which f and g are not the same. In some illustrative embodiments, compounds of formula II can include, for example

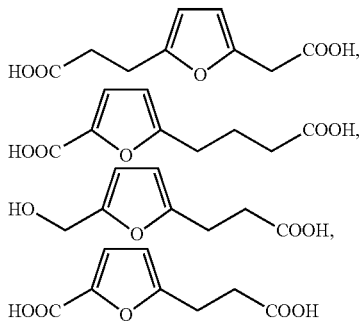

In some embodiments, compounds of formula III can be derived from cellulose, hemicellulose, or combinations thereof. In some embodiments, compounds of formula III can be derived from fructose from cellulose, hemicellulose or a combination thereof. In some such embodiments, the fructose can be dehydrated to form 5-hydroxymethylfurfural (HMF).

In some embodiments, compounds of formula III, as first monomeric units, can be polymerized, with at least second monomeric units. In some embodiments polymerization of compounds of formula III can be accomplished using free radical polymerization.

Some embodiments include compounds of formula V as first monomeric units:

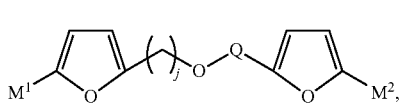

(V)

where $M^1$ and $M^2$ are independently —$(CH_2)_k$OH where k is 1, 2, 3, or 4; j is 1, 2, or 3; and Q is —$(CH_2)_p$ where p is 1, 2 or 3, or —$(CH_2)_qO(CH_2)$, where q and r are independently an integer from 1 to 10.

In some illustrative embodiments, compounds of formula V can include those in which $M^1$ and $M^2$ are both —$(CH_2)_k$OH. In some illustrative embodiments, compounds of formula V can include those in which $M^1$ and $M^2$ are the same. In some illustrative embodiments, compounds of formula V can include, for example

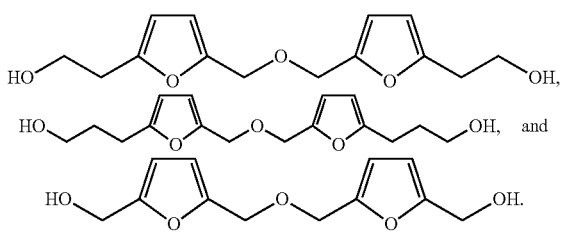

In some illustrative embodiments, compounds of formula V can include those in which Q is —$(CH_2)_qO(CH_2)_r$. In some illustrative embodiments, compounds of formula V can include, for example

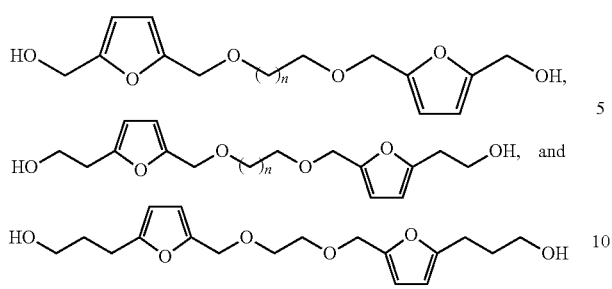

where n is an integer from 1 to 10.

In some embodiments, compounds of formula V can be derived from cellulose, hemicellulose, or combinations thereof. In some embodiments, compounds of formula V can be derived from fructose from cellulose, hemicellulose or a combination thereof. In some such embodiments, the fructose can be dehydrated to form 5-hydroxymethylfurfural (HMF).

In some embodiments, compounds of formula V, as first monomeric units can be polymerized with at least second monomeric units. In some embodiments polymerization of compounds of formula V can be accomplished using free radical polymerization.

In some embodiments, disclosed first monomeric units can include illustrative structures and/or compounds seen in compounds 17 to 20 below, which include a naphthalene group, which may be derived for example, from cellulose compounds.

(Cmpd. 17)

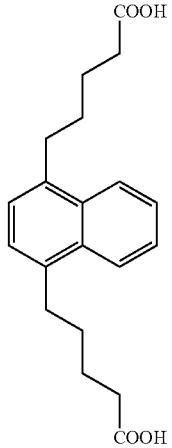

(Cmpd. 18)

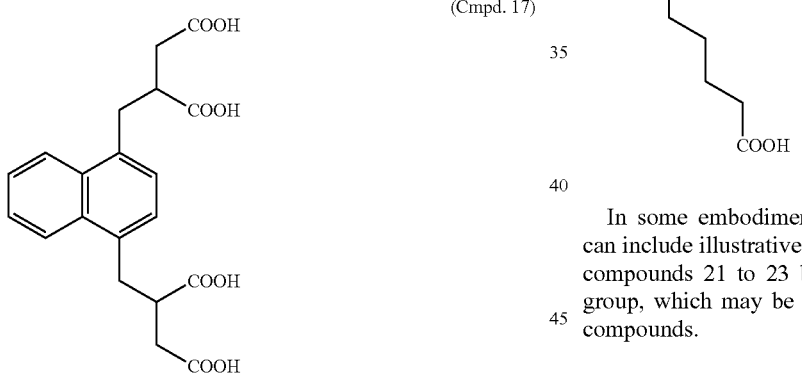

(Cmpd. 19)

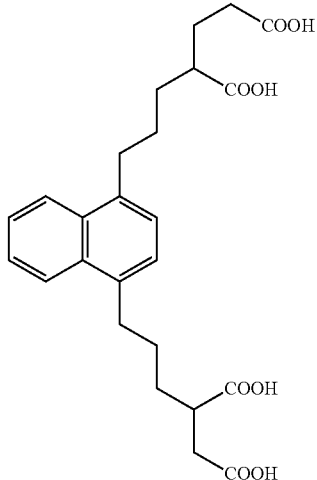

(Cmpd. 20)

In some embodiments, disclosed first monomeric units can include illustrative structures and/or compounds seen in compounds 21 to 23 below, which include a naphthalene group, which may be derived for example, from cellulose compounds.

(Cmpd. 21)

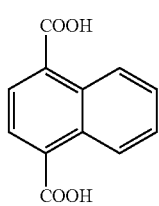

(Cmpd. 22)

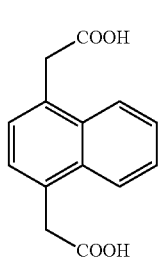

(Cmpd. 23)

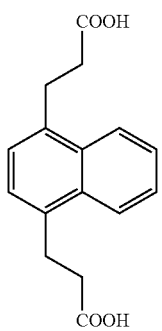

In some embodiments, disclosed first monomeric units can include illustrative structures and/or compounds seen in compounds 24 to 29 below, which include a furan group, which may be derived from cellulose compounds.

(Cmpd. 24)

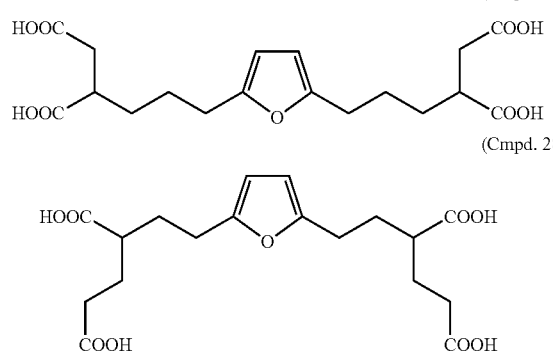

(Cmpd. 25)

(Cmpd. 26)

(Cmpd. 27)

(Cmpd. 28)

(Cmpd. 29)

In some embodiments, disclosed first monomeric units can include illustrative structures and/or compounds seen in compounds 30 to 32 below, which include a furan group, which may be derived from cellulose compounds.

(Cmpd. 30)

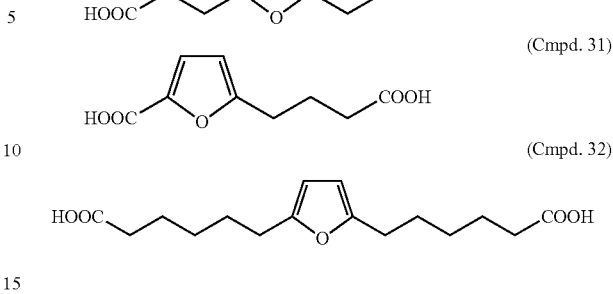

(Cmpd. 31)

(Cmpd. 32)

In some embodiments, disclosed first monomeric units can include illustrative structures and/or compounds seen in compounds 33 to 37 below, which include a furan group, which may be derived from cellulose compounds.

(Cmpd. 33)

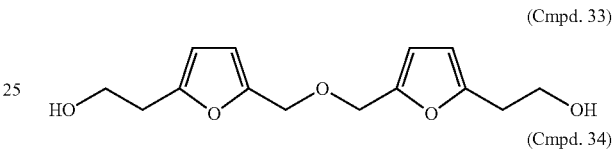

(Cmpd. 34)

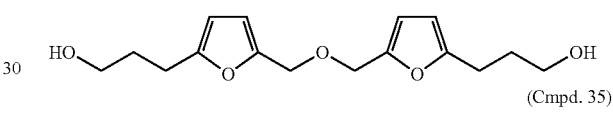

(Cmpd. 35)

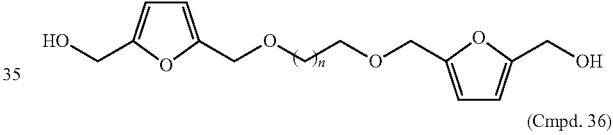

(Cmpd. 36)

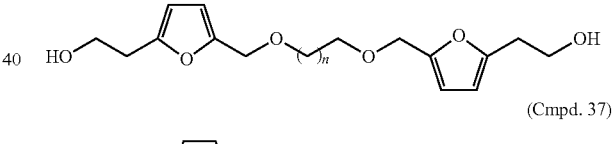

(Cmpd. 37)

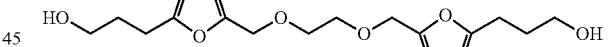

In some embodiments, disclosed first monomeric units can include illustrative structures and/or compounds seen in compounds 39 to 42 below, which include a furan group, which may be derived from cellulose compounds.

(Cmpd. 39)

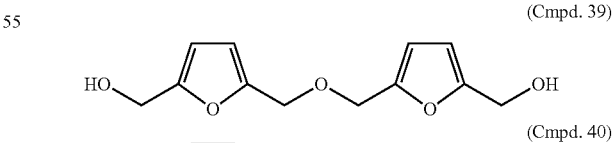

(Cmpd. 40)

(Cmpd. 41)

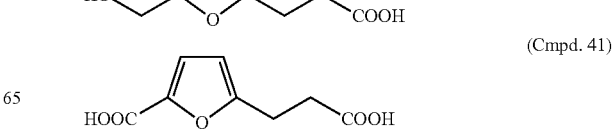

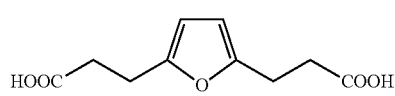
(Cmpd. 42)

The first monomeric units disclosed herein are typically functionalized, and can be optionally polyfunctionalized. The term "polyfunctionalized" includes functionalization with two (bifunctionalization) or more functional groups, which can be the same or different. Functionalization includes, but is not limited to, incorporation of a hydroxyl, aldehyde, carboxylic acid, ester, vinyl or allyl group into the monomer. Polyfunctionalized monomers can be symmetric or asymmetric. Monomers incorporating one or more aldehyde, carboxylic acid, or alcohol are especially useful as they can generally be interconverted, as well as extended by the addition of carbon fragments, using standard chemistries.

Second Monomers

Disclosed photodegradable polymers also include at least one second monomeric unit which includes a phototrigger. A phototrigger may broadly contain one or more functionalities that, when incorporated into a polymer chain, impart photocleavability or photodegradability to the polymer. A phototrigger unit is cleavable with the addition of light of a wavelength that is particular to the particular type of phototrigger.

The second, phototrigger containing, monomeric unit can be any bifunctional monomer that, when incorporated into a polymer, is photocleavable. In some embodiments, the phototrigger can be cleavable using UV light, such as UVA or UVB light. In some embodiments, visible light can also be used to cleave the phototrigger. In some embodiments, cleavage can be accomplished in the absence of an additive (e.g., a sensitizer). In other embodiments, cleavage can be accomplished in the presence of an additive (e.g., a sensitizer).

Illustrative second monomeric units and the wavelengths that can be used to photocleave them are shown below and include, but are not limited to, nitrobenzyl, coumaryl, arylmethyl, benzoin, and phenacyl containing monomers. It should be understood that the illustrative substitution patterns are representative examples, and the compounds can be differentially substituted in order to carry out degradation.

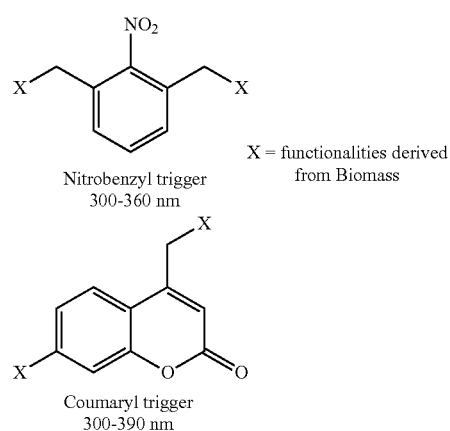

X = functionalities derived from Biomass

Nitrobenzyl trigger
300-360 nm

Coumaryl trigger
300-390 nm

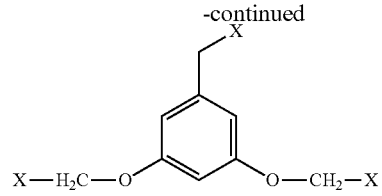

Arylmethyl trigger
300-390 nm

Coumaryl trigger is a subcategory of Arylmethyl trigger

Coumaryl Trigger is a Subcategory of Arylmethyl Trigger

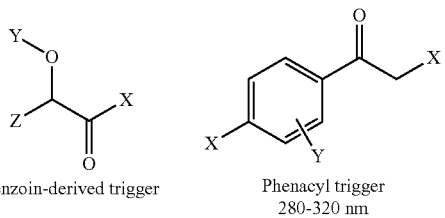

Benzoin-derived trigger

Phenacyl trigger
280-320 nm

In the above structures it should be understood that "X" generally represents a functionality derived from biomass, e.g. one of the first monomers, and is not limited to any particular functionality or structure. "X" can also represent a functionality present on a third (non-biomass) monomeric unit, if a third unit is present in the polymer, and is also not limited to any particular functionality or structure. More broadly, any of "X", "Y" and/or "Z" can represent a linkage to a functionality present on a compound obtained from biomass (i.e., first monomeric unit as described herein) or present on an optional third monomeric unit in the photodegradable polymer.

In the photodegradable polymers of the invention, the phototrigger second monomeric unit can be linked to a first, biomass-derived monomeric unit at one, two or three positions as exemplified by linkages X, Y and/or Z in the above structures; the phototrigger second monomeric unit can optionally be linked to a third (non-biomass derived) monomeric unit (if present) at one, two or three positions as exemplified in the above structures; or any combination thereof. The linkages represented by "X", "Y" and/or "Z", can be the same, or they can be different.

The second, phototrigger monomer can, for example, contain any of hydroxyl, aldehyde, carboxylic acid, and the like at the "X" position prior to polymerization with a first biomass monomer or a third monomer that includes a compatible functionality so as to permit polymerization using standard polymerization chemistries. "X", "Y" and/or "Z" can include, for example and without limitation, alkyl, alkoxy, or aryl. "Y" can include, for example, a functionalized group such as $OCH_2$—X where X represents a linkage to a biomass-derived component.

Optionally, the photodegradable polymer further includes at least one third monomeric unit, wherein the third monomeric unit is obtained from a petroleum product or is chemically or enzymatically synthesized. The optional third monomeric unit can be, for example, a hydrophilic monomer, such as an alkylene glycol.

The third monomeric unit, when present, can be selected to increase solubility of the polymer, to impart additional functionality to the resultant polymer, or to provide any desired properties. The optional third monomeric unit can impart additional functionality for example, by providing a site for cross-linking or further derivatization. An illustrative third monomeric unit is an alkylene glycol, such as ethylene glycol or propylene glycol; other examples of third monomeric units include, without limitation, cationic salts, anionic salts such as carboxylates or sulfonates, 1,4-butanediol, 1,6-hexanediol, 2,5-cis-bis(hydroxymethyl)tetrahydrofuran, and 1,6-hexamethylenediamine. The polymer may include a single third monomeric unit, or a plurality of different third monomeric units. In some embodiments, the third monomer includes an amine to increase solubility of the polymer and/or provide additional functionality.

The first, second and optional third monomeric units are at least bifunctional in order to facilitate polymerization; in some embodiments, the constituent monomers are compatibly bifunctionalized, such that a functional group of one bifunctionalized monomer is able to react with a chemically compatible functional group of another bifunctionalized monomer to form a covalent linkage. For example, the first, second or optional third monomeric unit can be a diol, a diacid, a diester, a dialdehyde, a diamine, a diallyl, a diether, a carbamate, an anhydride, a diamide, a diisocyanate, a diepoxide and/or a diaziridine. Illustrative functionalizations can include hydroxyl, aldehyde, carboxylic acid, amine, amide, ester, vinyl, or allyl group. In some embodiments, the functional groups on an individual monomeric unit are the same (e.g., two hydroxyl groups, or two acid groups) but they may be different. Polyfunctionalized monomers can be symmetric or asymmetric. Monomeric units incorporating one or more aldehyde, carboxylic acid, amine, or alcohol may be especially useful as they can generally be interconverted, as well as extended by the addition of carbon fragments, using standard chemistries. The first, second and optional third monomeric units may be selected so as to permit polymerization; for example, the first, biomass-derived monomeric unit can be a diol, and the second monomeric unit constituting the phototrigger can be a diacid. In some embodiments, when an optional third monomeric unit is incorporated into the polymer, it can have the same functionality as the second, phototrigger monomeric unit. For example, if the second, phototrigger monomeric unit is a diol, the third monomeric unit can also be a diol, such that both are capable of reacting with a diacid first monomeric unit derived from biomass.

Disclosed polymers may contain any amounts of first, second and optional third monomers. In some embodiments of the polymer, the polymer may contain a higher number of first and/or third monomeric units than second (phototrigger) monomeric units. The ratio of first:second:third monomeric units (x:y:z) can be any selected ratio, reflecting for example the desired properties of the polymer and/or its intended use. An example of the ratio x:y:z is 1:0.1:0.9 where x is 1, y is 0.1 and z is 0.9.

The polymers of the invention, derived from renewable resources, may be characterized by higher degrees of degradability and sustainability. The built-in photocleavable unit(s) result in photodegradable polymers that can be pre-programmed for degradation with light of a chosen wavelength, for example UV irradiation.

In some embodiments, photolytic decomposition of the polymer can optionally be followed by isolation, purification and/or recovery of one or more constituent monomeric or oligomeric units. In some embodiments, a monomeric or oligomeric unit derived from biomass can be isolated, purified, and/or recovered from decomposed polymer, which can in turn be reused or recycled, for example as components of other polymers, thereby minimizing the impact on the environment and making the process both green and sustainable. The examples below show that monomers produced after photodegradation can be successfully reused to build the polymer.

The invention thus includes methods of polymerizing the first, second and optional third monomers to form a polymer, as well as uses of the polymer in commercial, industrial, and medical applications, for example as a coatings, adhesives, oils, gels, films, paints, and the like. Polymers of the invention may include nylons, polyesters, polyurethanes, polyamides and the like. The invention further includes a method for degrading the polymer of the invention by exposing the polymer to radiation, for example UV irradiation at a selected wavelength, and for a time sufficient, to photocleave the polymer. For example, the solid polymer can be ground, a solvent added (e.g., THF/water) and the mixture can be irradiated with UV light for a time sufficient to achieve photocleavage. Degradation can alternatively take place in the powder form. Optionally, the degradation products, particularly the product derived from biomass, can be isolated, purified and/or recovered and reused.

Further details and specific embodiments are shown by the examples included herein. The examples provided herein synthesize model compounds comprising a first monomer derived from biomass and a second monomer, a nitrobenzyl chromophore, which functions as a phototrigger. Also shown is a polymer formed from a 1:1 combination of a biomass-derived monomer and a phototrigger. Also shown is a copolymer consisting of a first monomer derived from biomass (i.e., FDCA), a second monomer constituting a phototrigger, and a third monomer, ethylene glycol. These compounds are exemplary, and the invention is readily applicable to polymers formed from any bifunctionalized monomer derived from biomass, any bifunctionalized phototrigger, and any suitable bifunctionalized third polymer, provided that the monomer functionalizations are selected so as to permit polymerization. Preferably the constituent monomers are compatibly bifunctionalized, such that a functional group of one bifunctionalized monomer is able to react with a chemically compatible functional group of another bifunctionalized monomer to form a covalent linkage. The two functional groups of a bifunctionalized monomer may be the same, or they may be different.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the invention is not intended to describe each disclosed embodiment or every implementation of the present invention. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

EXAMPLES

The present invention is illustrated by the following examples. It is to be understood that the particular examples, materials, amounts, and procedures are to be interpreted broadly in accordance with the scope and spirit of the invention as set forth herein.

Example 1

Programmed Degradation of Polymeric/Oligomeric Materials Derived from Renewable Bio-Resources All commercially obtained reagents/solvents were used as received; chemicals were purchased from Alfa Aesar®, Sigma-Aldrich®, Acros Organics®, TCI America®, Mallinckrodt®, and Oakwood® Products, and were used as received without further purification. Unless stated otherwise, reactions were conducted in oven-dried glassware under nitrogen atmosphere. 1H-NMR and 13C-NMR spectra were recorded on Varian 500 MHz (125 MHz for $^{13}$C) or Bruker 400 MHz (100 MHz for $^{13}$C) or Varian 400 MHz (100 MHz for $^{13}$C) spectrometers. Data from the $^1$H-NMR spectroscopy are reported as chemical shift (δ ppm) with the corresponding integration values. Coupling constants (J) are reported in hertz (Hz). Standard abbreviations indicating multiplicity were used as follows: s (singlet), b (broad), d (doublet), t (triplet), q (quartet), m (multiplet) and virt (virtual). Data for $^{13}$C NMR spectra are reported in terms of chemical shift (δ ppm). High-resolution mass spectrum data in Electrospray Ionization mode were recorded on a Bruker—Daltronics® BioTof mass spectrometer in positive (ESI+) ion mode. IR spectra were recorded in Thermo Scientific Nicolet Nexus 470 FT-IR spectrometer and band positions are reported in reciprocal centimeters. Samples were made as pellet with KBR and IR spectrum was recorded. Absorbance measurements were performed using a Shimadzu® UV-2501PC UV-Vis spectrophotometer and Agilent® Cary 300 UV-Vis spectrophotometer. Tetrahydrofuran (THF) dried over sodium and HPLC graded $H_2O$ (Alfa Aesar®) were used for UV-Vis measurements. Powder X-Ray Diffraction (PXRD) measurements were made in Phillips X'Pert MPD powder X-ray diffractometer (λ=1.54060) with step size of 0.0500 (2θ) and continuous scan type. 2θ range from 5 to 80°. Thermo Gravimetric Analysis (TGA) were performed in TA instruments Q500 Hi-RES Thermogravimetric analyzer under nitrogen atmosphere with temperature increment of 10° C./min. Differential Scanning calorimeter measurements were performed in TA instruments' Q1000 Modulated Differential Scanning calorimeter. Gel permeation chromatography analysis were performed in Symyx Rapid GPC equipped with ELS detector (PL-ELS1000), two varian PL gel Mixed-β10 μm 300× 7.5 mm columns and HP 100 series pump.

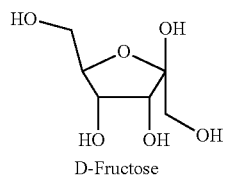

D-Fructose

1

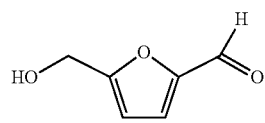

2

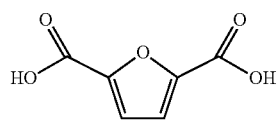

3

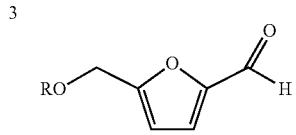

a) R = Bz
b) R = TIPS 4a-b

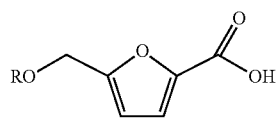

a) R = Bz
b) R = TIPS 5a-b

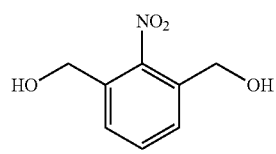

6

-continued

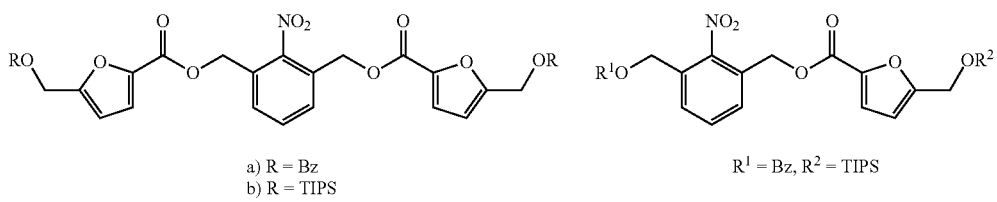

7a-b a) R = Bz
b) R = TIPS

9

$R^1$ = Bz, $R^2$ = TIPS

PhCOOH

10

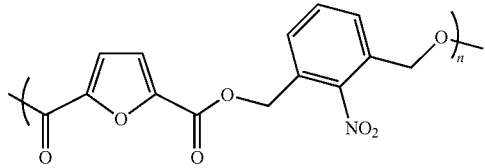

11

12

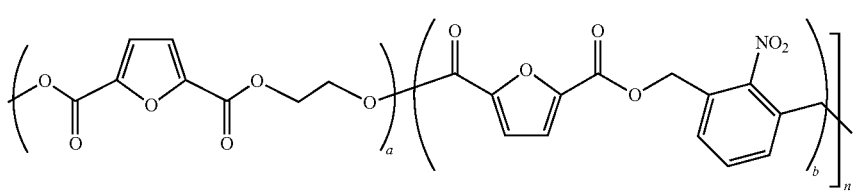

13

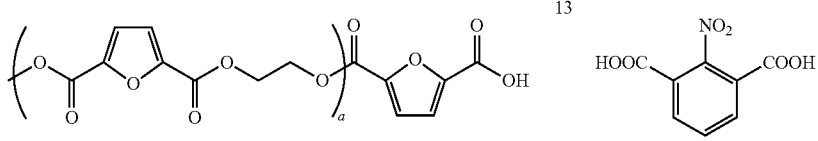

14

15

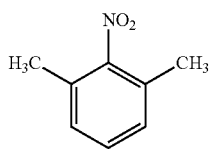

16

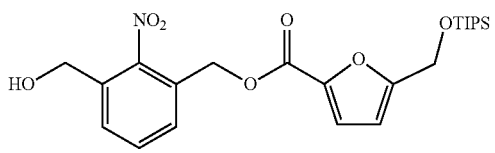

Renewable polymeric materials derived from biomass with built-in phototriggers were synthesized and evaluated for degradation under UV irradiation. Complete decomposition of the polymeric materials was observed with recovery of monomers that was used to resynthesize the polymers. Our proof of principle strategy has shown that one can successfully append triggering units to monomers derived from biomass and recover them after degradation so that the monomers can be reused to minimize impact on the environment making the process both green and sustainable. Illustrative compounds were utilized to establish the reaction conditions and to investigate degradation efficiency and recoverability.

The synthesis of such illustrative compounds from renewable materials for programmed degradation can be seen in Scheme 1 below.

Scheme 1

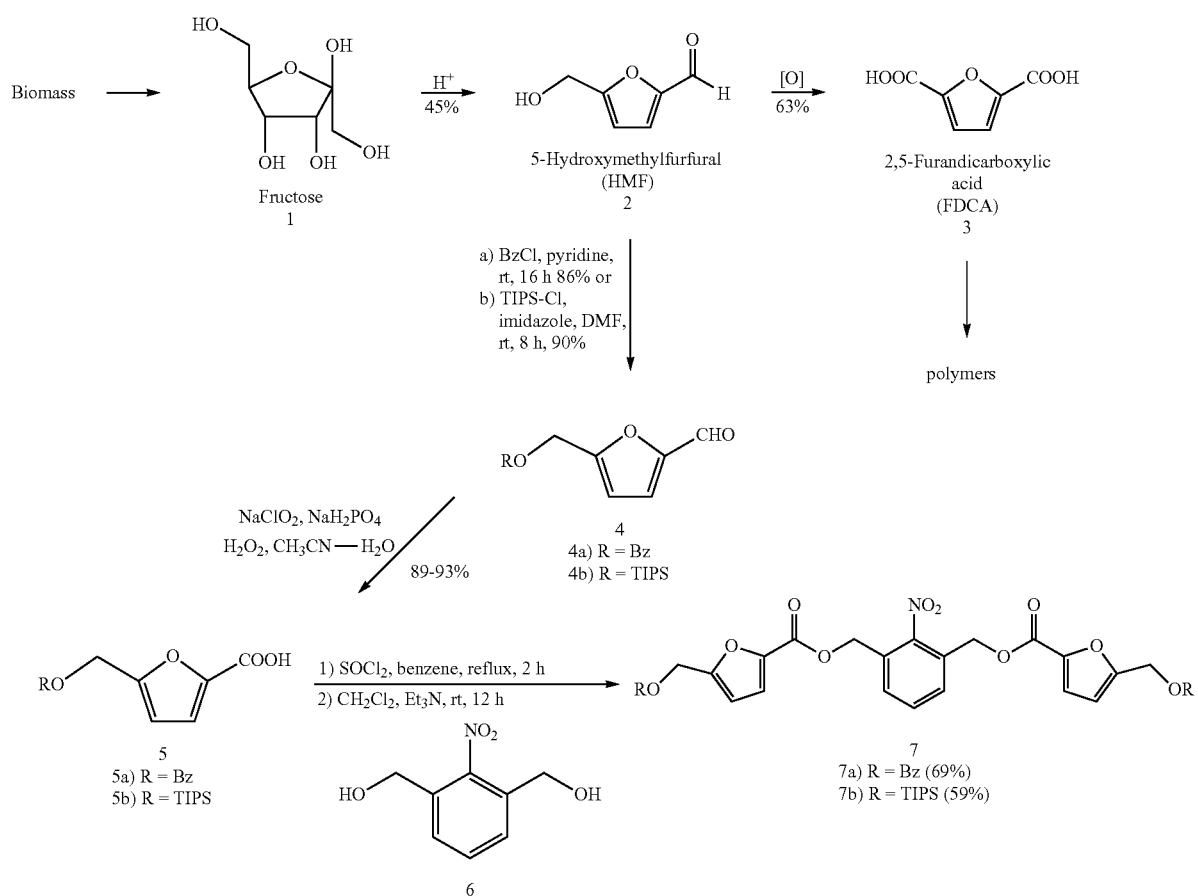

Generally, established literature procedures (J. B. Binder, R. T. Raines, *J. Am. Chem. Soc.* 2009, 131, 1979-1985) were utilized to convert fructose 1 to furan based derivatives viz., HMF 2 and FDCA 3 as they are synthetically accessible. These bio-based furan derivatives were employed both as building blocks for model compounds and as monomers and were functionalized with 2-nitro-1,3-benzenedimethanol 6, which served as a phototrigger.

Following are specific details regarding synthesis and characterization of the above noted compounds.

Synthesis of 5-hydroxymethylfurfural 2

Scheme S1: Synthesis of 5-hydroxymethylfurfural 2

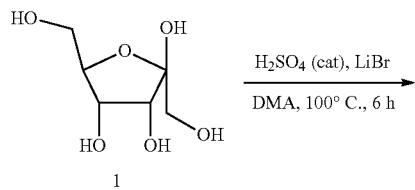

-continued

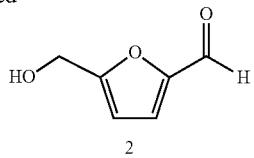

5-Hydroxymethylfurfural 2 was synthesized according to a procedure reported in the literature.) To a solution of D-fructose (10 g, 55.5 mmol, 1 equiv.) in N,N-dimethylacetamide (DMA, 100 mL) under $N_2$ atmosphere, LiBr (10 g, 10% wt) was added, followed by catalytic amount of $H_2SO_4$ (0.326 g, 3.33 mmol, 0.06 equiv. 0.17 mL) and stirred at 100° C. for 6 h. After the reaction, the mixture was cooled to room temperature and filtered through celite bed to remove any insoluble residue. Celite bed was washed with ethyl acetate (EtOAc) (3×25 mL). Ethyl acetate in the filtrate was removed under reduced pressure, followed by removal of DMA by vacuum distillation. The residue after vacuum distillation was diluted with EtOAc, washed with brine solution, extracted with EtOAc. The organic layer was dried over anhyd.$Na_2SO_4$, and the solvent was removed under reduced pressure. The crude product was purified by column chromatography using hexane-ethyl acetate mixture. 5-hydroxymethylfurfural (HMF, 2) was obtained as brown viscous oil (which solidifies upon cooling).

Figure 2:
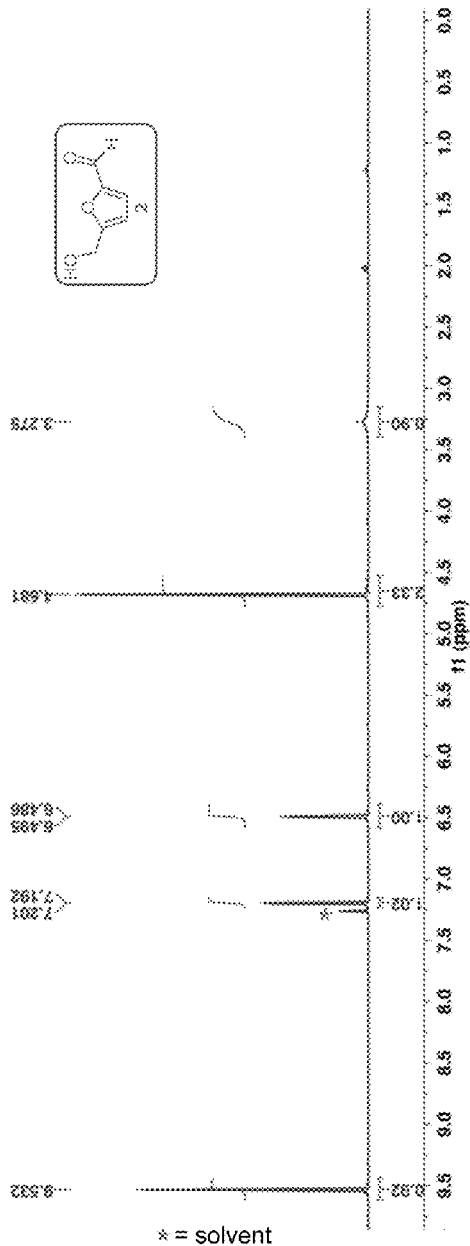
FIG. 2 is a $^1$H nuclear magnetic resonance (NMR) spectrum (400 MHz, CDCl$_3$, δ ppm) of compound 2.
Figure 3:
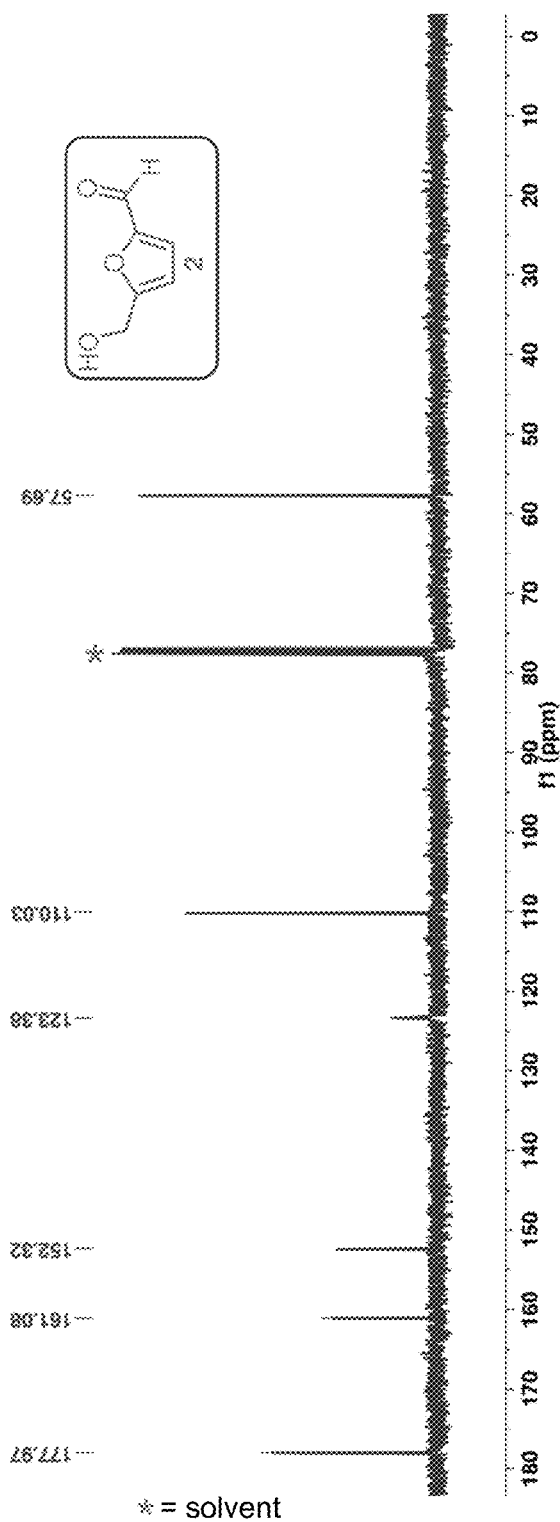
FIG. 3 is a $^{13}$C NMR spectrum (100 MHz, CDCl$_3$, δ ppm) of compound 2.

TLC condition—Rf=0.30 (40% hexanes: 60% ethyl acetate) for 2 (Yield=45%). FIG. 2 shows a $^1$H-NMR and FIG. 3 shows a $^{13}$C-NMR of hydroxymethylfurfural 2.

2 Synthesis of 2,5-furandicarboxylic acid (FDCA) 3

Scheme S2: Synthesis of 2,5-furandicarboxylic acid (FDCA) 3

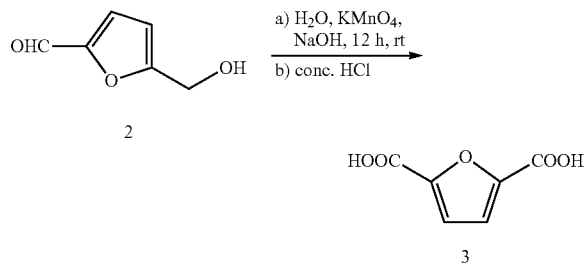

2,5-Furan dicarboxylic acid (FDCA) was synthesized according to a procedure reported in the literature (D. Yoon, D. E. Gross, V. M Lynch, J. L. Sessler, B. P. Hay, C. Lee, *Angew. Chem. Int. Ed.*, 2008, 47, 5308) To a solution of HMF (2) (6.99 g, 0.055 mmol, 1 equiv.) in H$_2$O (370 mL), aq. NaOH (51 g, 1.27 mol, 23 equiv. in 93 mL of water) was added followed by the addition of KMnO$_4$ (20.17 g, 0.127 mol, 2.3 equiv. in 92 mL of water) and the reaction mixture was stirred at room temperature for 12 h. After completion the reaction mixture was filtered to remove the insoluble residue. The filtrate was cooled to 0-5° C. and pH of the solution was adjusted to ~1 with concd. HCl. The product precipitates as pale yellow solid that was filtered, washed with excess of water and dried in high vacuum at 60° C. to give pure product 3. Yield=64%

Figure 4:
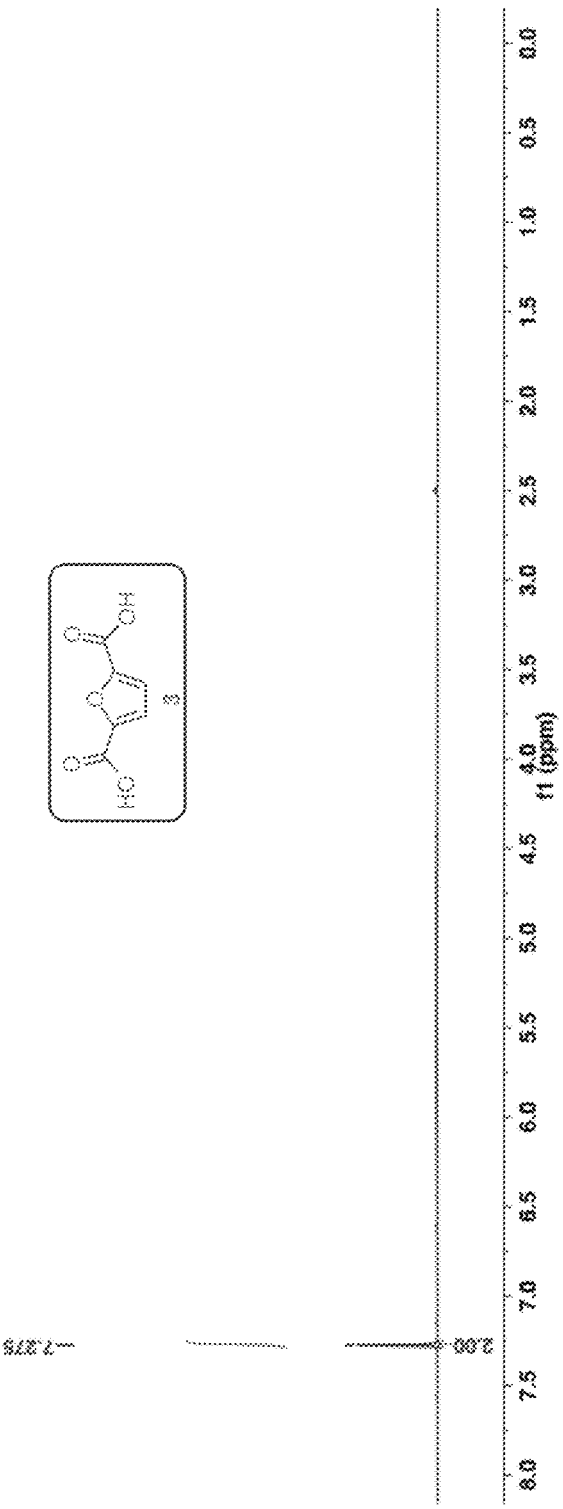
FIG. 4 is a $^1$H NMR spectrum (500 MHz, DMSO-d$_6$, δ ppm) of compound 3.
Figure 5:
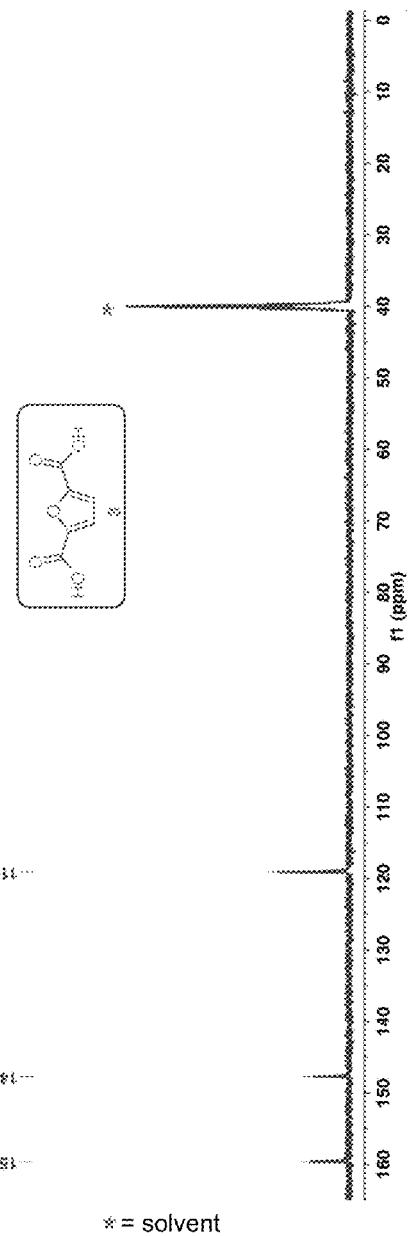
FIG. 5 is a $^{13}$C NMR spectrum (125 MHz, DMSO-d$_6$, δ ppm) and ESI-MS (electrospray ionization-mass spectrometry) data of compound 3.

FIG. 4 shows a $^1$H NMR and FIG. 5 shows a $^{13}$C NMR, ESI-MS data and IR data of 2,5-furandicarboxylic acid (FDCA) 3.

Synthesis of Benzoyl Protected 5-Hydroxymethylfurfural 4a

Scheme S3:
Synthesis of benzoyl protected 5-hydroxymethylfurfural 4a

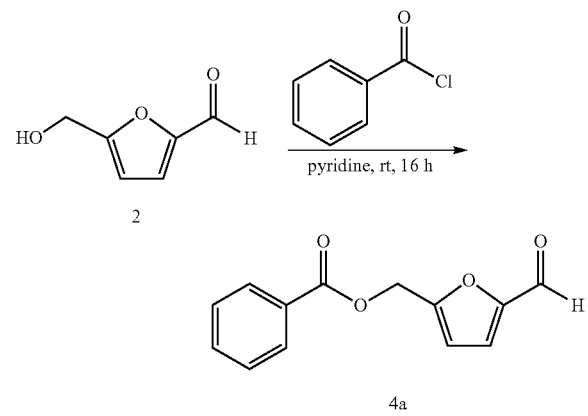

Compound 4a was synthesized according to a procedure reported in the literature (R. Bognar, P. Herczegh, M. Zsely, *Carbohydr. Res.*, 1987, 164, 465.) To a stirred solution of 5-hydroxymethylfurfural (2) (1.5 g, 11.9 mmol, 1 equiv.) in pyridine (6 mL), benzoyl chloride (3.35 g, 23.8 mmol, 2 equiv., 2.8 mL) was added drop wise at 0° C. The resulting mixture was allowed to warm to room temperature over 16 h. After the reaction, the mixture was quenched with cold dil. H$_2$SO$_4$ (5%) and extracted with CH2Cl2 (3×25 mL). The combined organic layer was washed with satd. NaHCO3 (~30 mL) solution, dried over anhyd. Na$_2$SO$_4$, and the solvent was removed under reduced pressure. The crude product was purified by column chromatography using hexane-ethyl acetate. Benzoyl protected HMF (4a) was obtained as white solid. TLC condition—Rf=0.50 (60% hexanes: 40% ethyl acetate) for 4a (Yield=86%)

Figure 6:
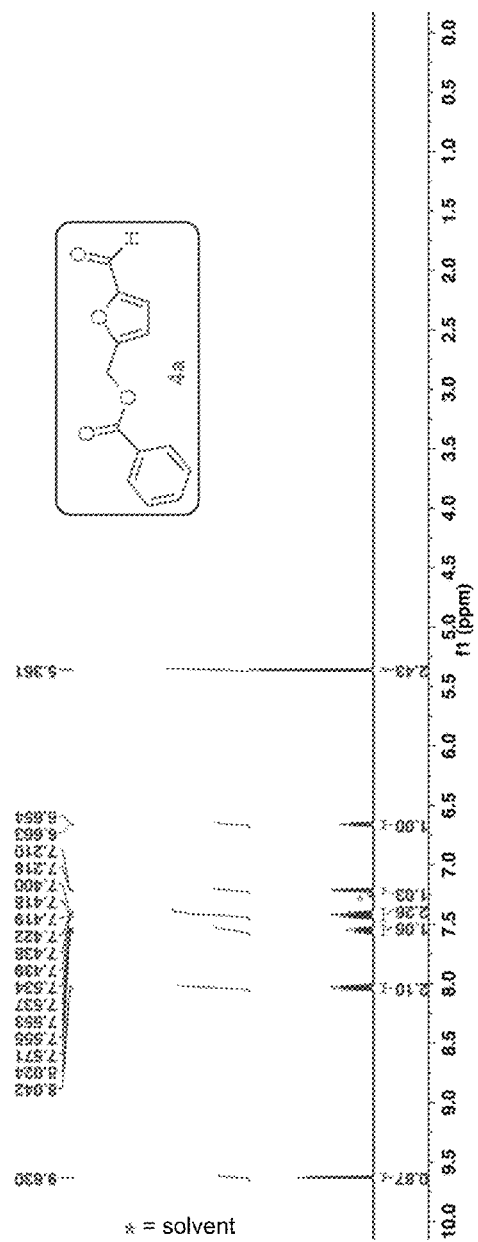
Figure 7:
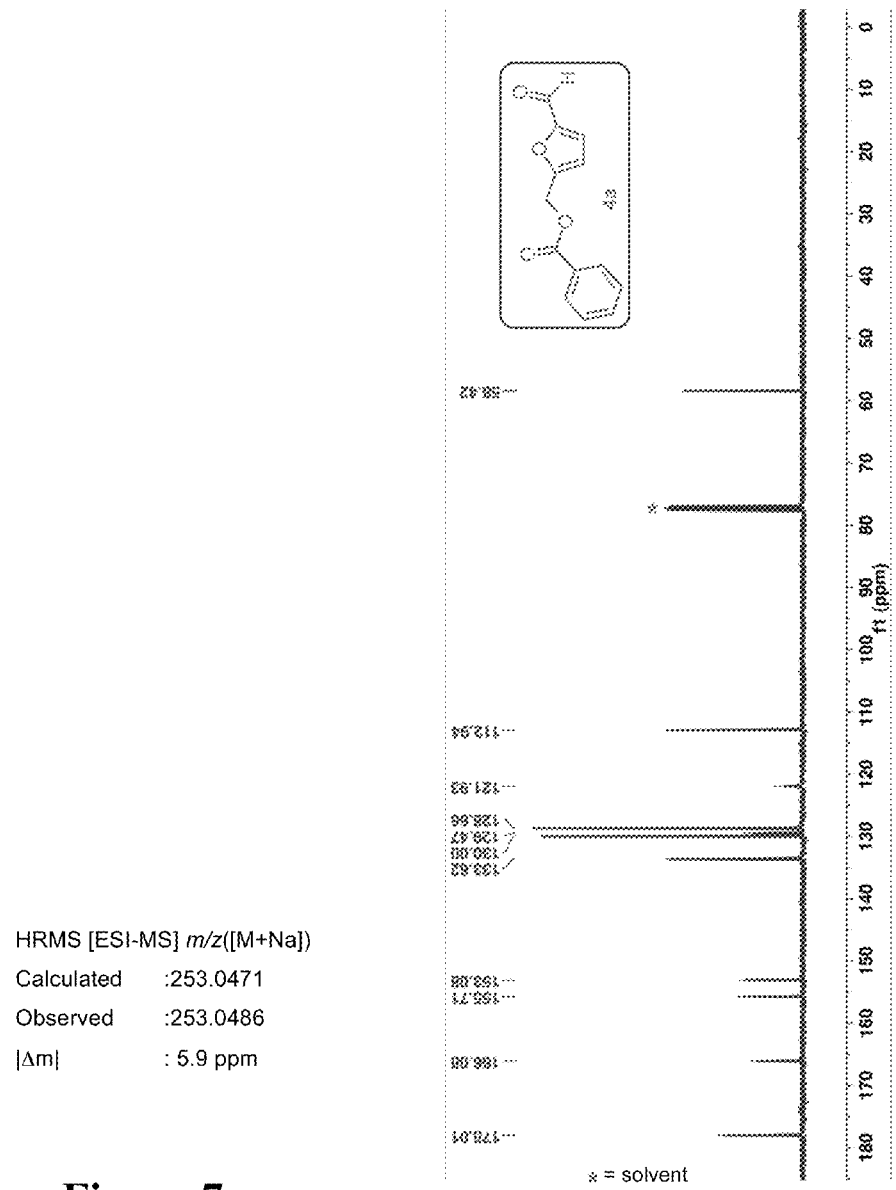

FIG. 6 shows a 1H NMR and FIG. 7 shows a 13C NMR and ESI-MS data of benzoyl protected 5-hydroxymethylfural 4a.

Synthesis of TIPS Protected 5-Hydroxymethylfurfural 4b

Scheme S4: Synthesis of TIPS protected 5-hydroxymethylfurfural 4b

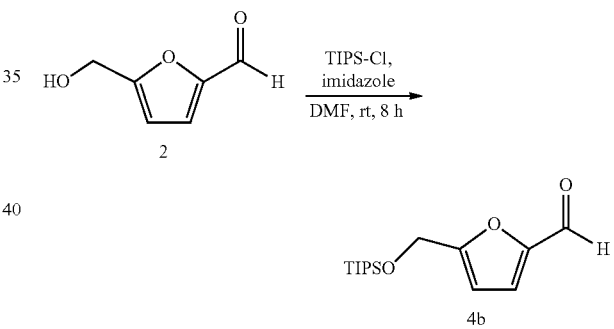

Literature reported procedure was followed for the synthesis of 4b (B. J. McNeils, D. D. Sternbach, A. T. Macphail. *Tetrahedron*, 1994, 50, 6767.) To a solution of triisopropylsilyl chloride (1.16 g, 6 mmol, 1.2 equiv., 1.28 mL) in DMF (5 mL), imidazole (0.687 g, 10 mmol, 2 equiv.), and 2 (0.63 g, 5 mmol, 1 equiv.) were added and stirred at room temperature for 8 h. After the reaction, the mixture was diluted with water and extracted with hexane. The organic layer was dried over anhyd. Na$_2$SO$_4$ and the solvent was removed under reduced pressure. The crude product was purified by column chromatography using hexane-ethyl acetate mixture. Pure compound (4b) was obtained as pale yellow viscous liquid. TLC condition—Rf=0.80 (85% hexanes: 15% ethyl acetate) for 4b (Yield=90%).

Figure 8:
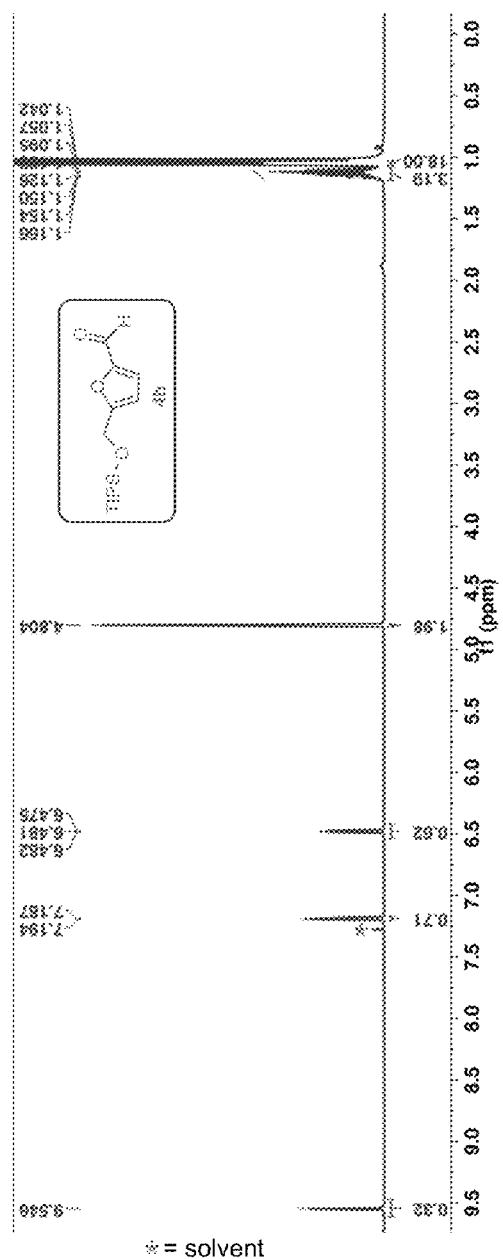
FIG. 8 is a $^1$H NMR spectrum (500 MHz, CDCl$_3$, δ ppm) of compound 4b.
Figure 9:
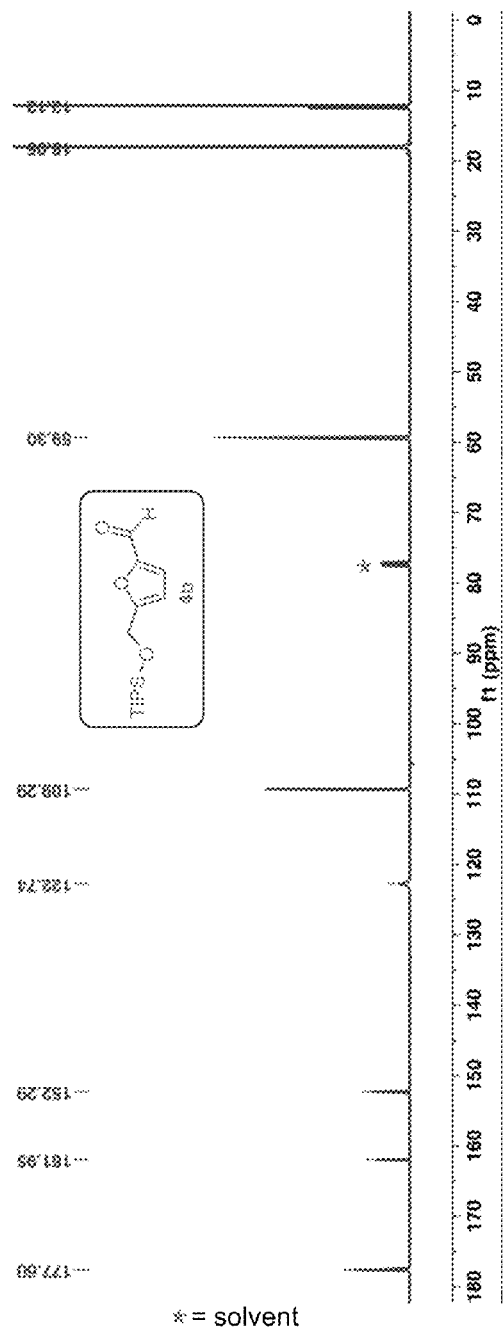
FIG. 9 is a $^{13}$C NMR spectrum (125 MHz, CDCl$_3$, δ ppm) and ESI-MS (electrospray ionization-mass spectroscopy) data of compound 4b.

FIG. 8 shows a $^1$H NMR and FIG. 9 shows a $^{13}$C NMR and ESI-MS data of TIPS protected 5-hydroxymethylfurfural 4b.

Scheme S5:
Synthesis of 5-((benzoyloxy)methyl)furan-2-carboxylic acid 5a

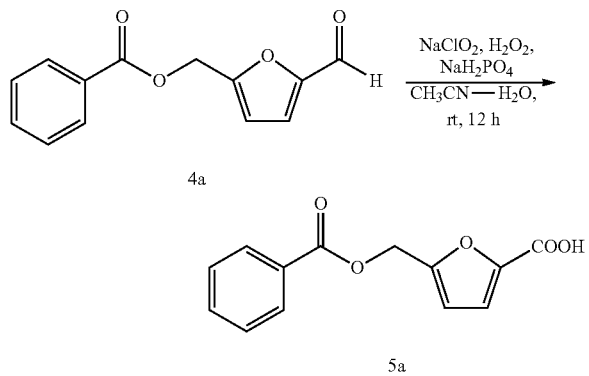

Figure 10:
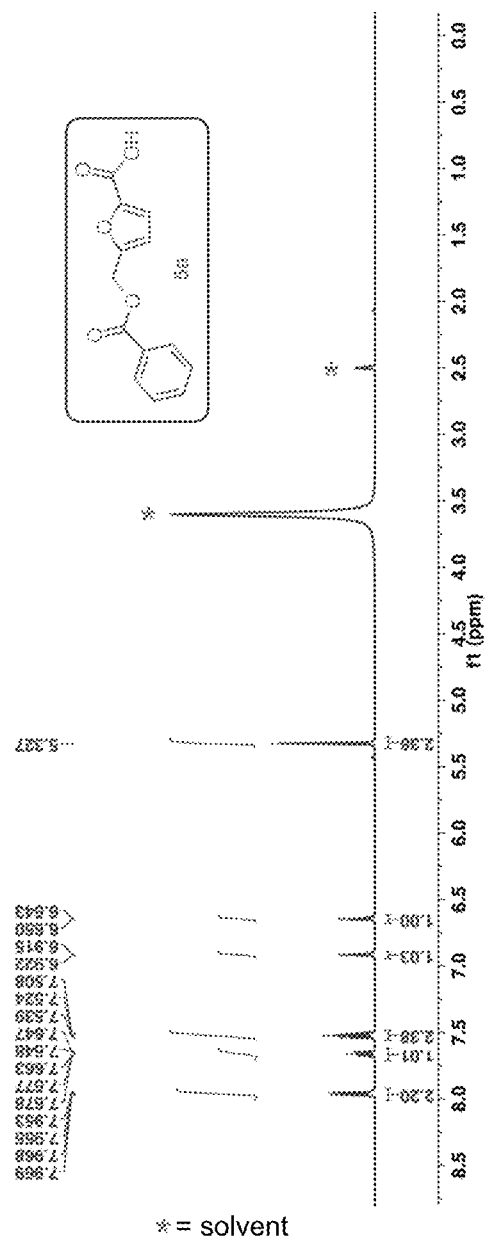
Figure 11:
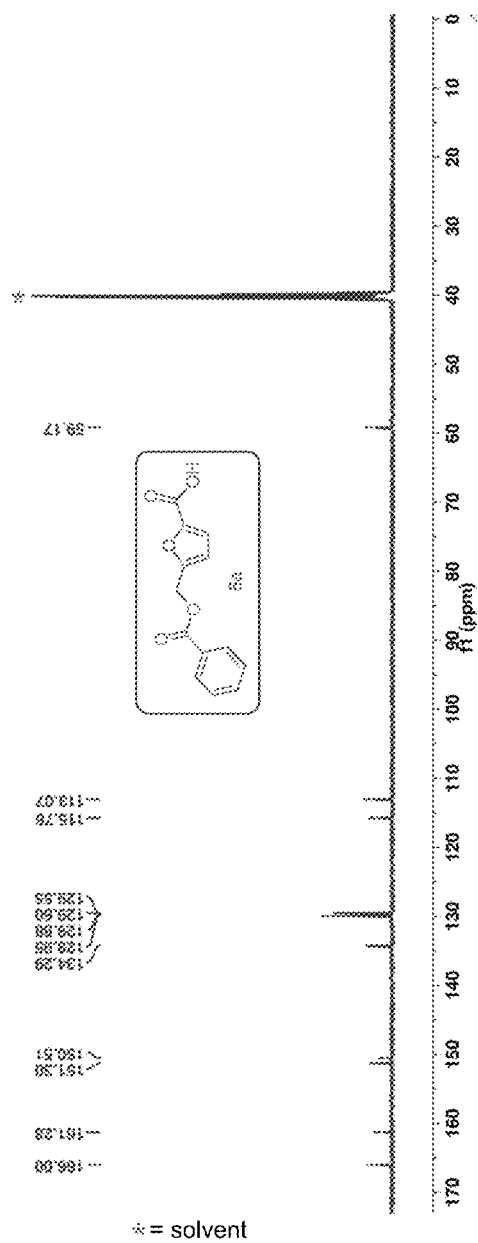

Literature reported procedure was followed for the synthesis of compound 5a (E. Dalcanale, F. Montanari, *J. Org. Chem.*, 1986, 51, 567). To a solution of 4a (0.23 g, 1 mmol, 1 equiv.) in acetonitrile (2 mL) at 0° C., aq NaH$_2$PO$_4$ (50 mg in 0.5 mL of water) was added. To this mixture, 30% aq. H$_2$O$_2$ (5 mmol, 5 equiv., 0.6 mL) was added drop wise followed by the addition of aq. NaClO$_2$ (0.135 g, 1.5 mmol, 1.5 equiv., 2 mL water) over 15 min. The resulting mixture was allowed to warm to room temperature over 12 h. The product precipitated as white solid, which was filtered, washed with excess of water, acetone and dried in high vacuum to give pure product. Compound 5a was obtained as white solid. TLC condition—Rf=0.60 (60% hexanes: 40% ethyl acetate) for 5a (Yield=89%). FIG. 10 shows a $^1$H NMR and FIG. 11 shows a $^{13}$C NMR and ESI-MS data of 5-((benzoyloxy)methyl)furan-2-carboxylic acid 5a.

Synthesis of 5-(((triisopropylsilyl)oxy)methyl)furan-2-carboxylic acid 5b

Scheme S6: Synthesis of 5-(((triisopropylsilyl)oxy)methyl)furan-2-carboxylic acid 5b

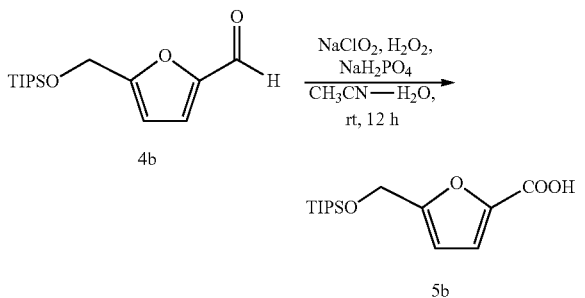

Literature reported procedure was followed for the synthesis of 5b (E. Dalcanale, F. Montanari, *J. Org. Chem.*, 1986, 51, 567) To a solution of 4b (23 g, 0.081 mol, 1 equiv.) in acetonitrile (120 mL) at 0° C., aq. NaH$_2$PO$_4$ (7 g in 30 mL of water) was added. To this mixture, 30% aq. H$_2$O$_2$ (0.407 mol, 5 equiv., ~50 mL) was added drop wise followed by the drop wise addition of aq. NaClO$_2$ (11.04 g, 0.122 mol, 1.5 equiv., 120 mL of water) over 1 h. The resulting mixture was allowed to warm to room temperature over 12 h. After reaction, the mixture was quenched with water and extracted with EtOAc. The organic layer was dried over anhyd. Na2SO4 and the solvent was removed under reduced pressure to give pure compound 5b as white semi-solid. TLC condition—Rf=0.50 (85% hexanes: 15% ethyl acetate) for 5b (Yield=90%).

Figure 12:
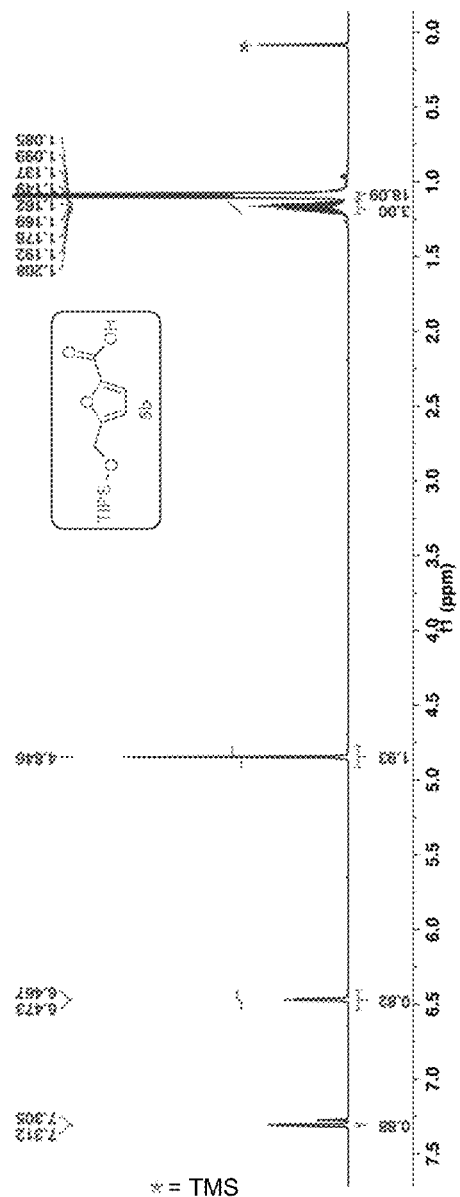
FIG. 12 is a $^1$H NMR spectrum (500 MHz, CDCl$_3$, δ ppm) of compound 5b.
Figure 13:
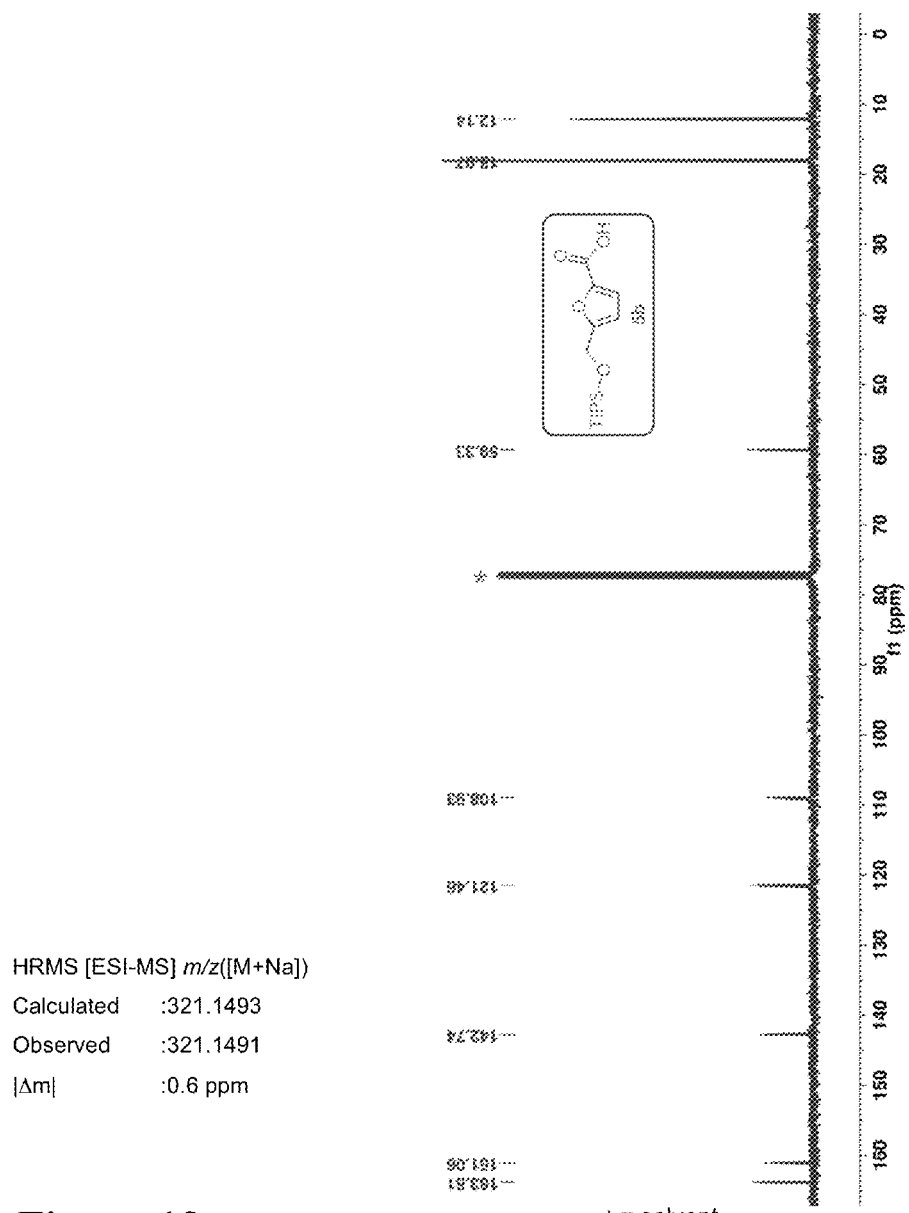
FIG. 13 is a $^{13}$C NMR spectrum (100 MHz, CDCl$_3$, δ ppm) and ESI-MS data of compound 5b.

FIG. 12 shows a $^1$H NMR and FIG. 13 shows a $^{13}$C NMR and ESI-MS data of 5-(((triisopropylsilyl)oxy)methyl)furan-2-carboxylic acid 5b.

Synthesis of 2-nitro-1,3-benzenedicarboxylic acid 14

Scheme S7: Synthesis of 2-Nitro-1,3-benzenedicarboxylic acid 14

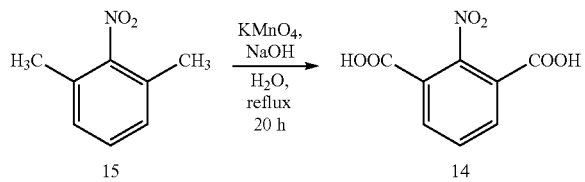

Literature reported procedure was followed for the synthesis of 14. (D. Han, X. Tong, Y. Zhao, *Macromolecules*, 2011, 44, 437.) To a stirred solution of 1,3-dimethyl-2-nitrobenzene 15 (15.1 g, 0.1 mol, 1 equiv.) in water (750 mL), NaOH (6 g, 0.15 mol, 1.5 equiv.) was added and refluxed. To this KMnO$_4$ (60 g, 0.38 mol, 3.8 equiv.) was added slowly over a period of 3 h. The resulting mixture was refluxed for 20 h. After the reaction, the mixture was cooled to room temperature and filtered. The filtrate was acidified with concd. HCl. The title compound, 14 precipitated out as white solid. The precipitate was filtered, washed with excess water and dried under vacuum. TLC condition—Rf=0.60 (90% hexanes: 10% ethyl acetate) for 15 (Yield=72%).

Figure 14:
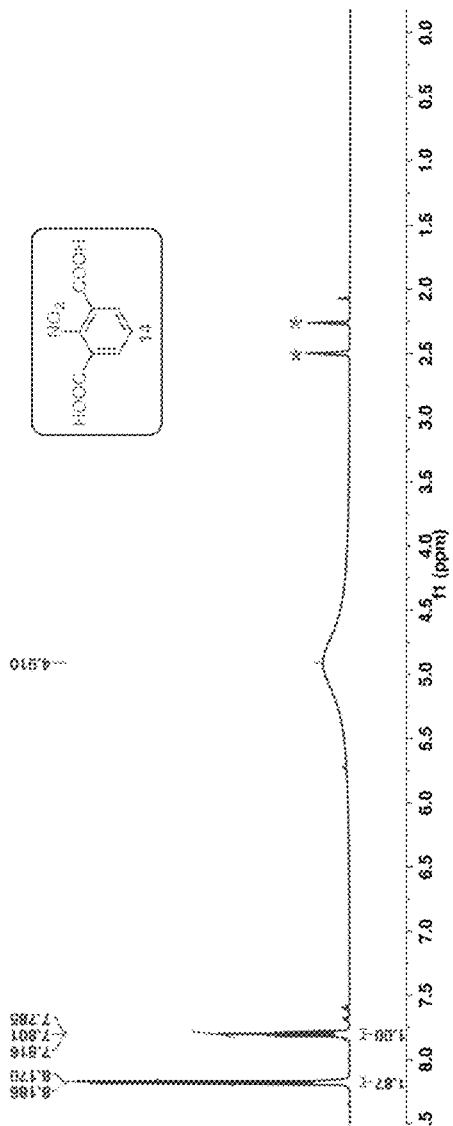
FIG. 14 is a $^1$H NMR spectrum (500 MHz, DMSO-d$_6$, δ ppm) of compound 14.
Figure 15:
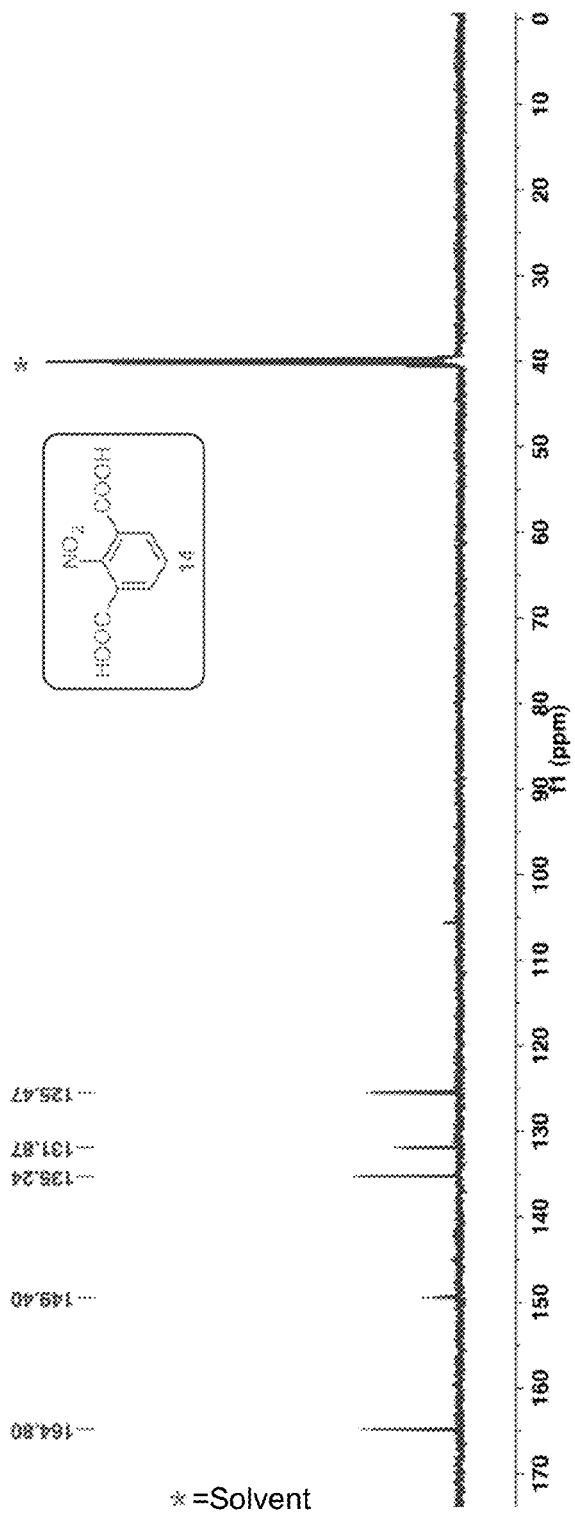
FIG. 15 is a $^{13}$C NMR spectrum (125 MHz, DMSO-d$_6$, δ ppm) of compound 14.

FIG. 14 shows a $^1$H NMR and FIG. 15 shows a $^{13}$C NMR of 2-nitro-1,3-benzenedicarboxylic acid 14.

Synthesis of 2-nitro-1,3-benzenedimethanol 6

Scheme S8: Synthesis of 2-Nitro-1,3-benzenedimethanol 6

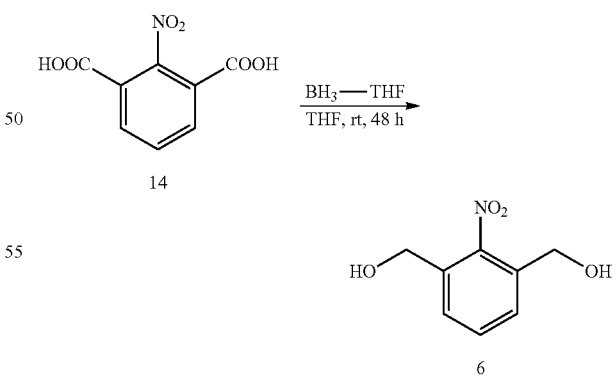

2-Nitro-1,3-benzenedimethanol 6 was synthesized according to a procedure reported in the literature. (D. Han, X. Tong, Y. Zhao, *Macromolecules*, 2011, 44, 437.) To a solution of 2-nitro-1,3-benzenedicarboxylic acid (14) (1.25 g, 5.9 mmol, 1 equiv.) in THF, BH$_3$-THF complex (1.0 M in THF. 2.53 g, 29.5 mmol, 5 equiv., 29.5 mL) was added at 0°

C. over 1 h. The resulting mixture was allowed to warm to room temperature over 48 h. After reaction, THF was removed under vacuum; the reaction mixture was quenched with water, and extracted with EtOAc. The combined organic layer was dried over anhyd. $Na_2SO_4$ and solvent were removed under reduced pressure to give crude product. Crude product was purified by column chromatography (hexane-EtOAc). 2-Nitro-1,3-benzenedimethanol 6 was obtained as a white solid. TLC condition—Rf=0.8 (95% DCM: 05% Methanol) for 6 (Yield=81%).

Figure 16:
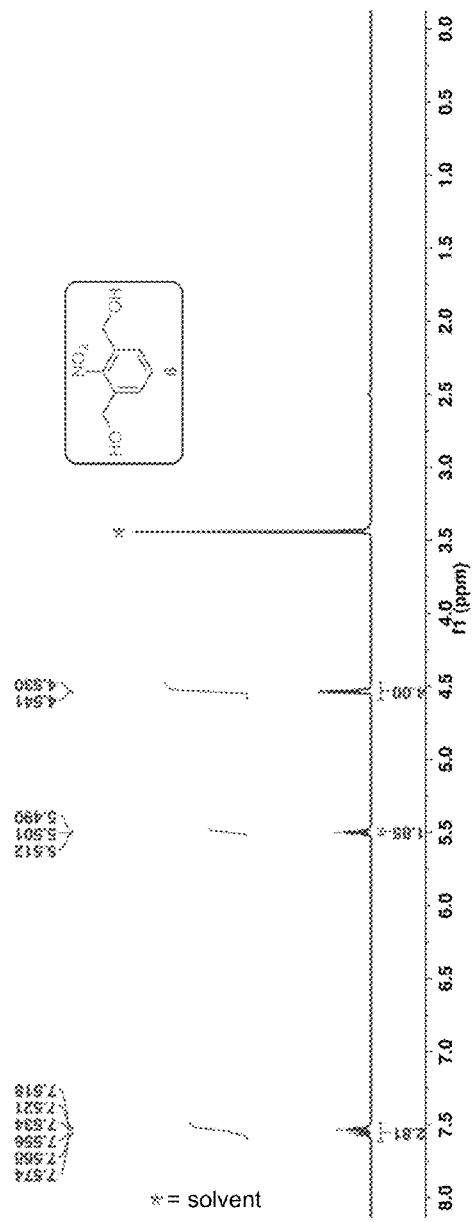
FIG. 16 is a $^1$H NMR spectrum (500 MHz, DMSO-d$_6$, δ ppm) of compound 6.
Figure 17:
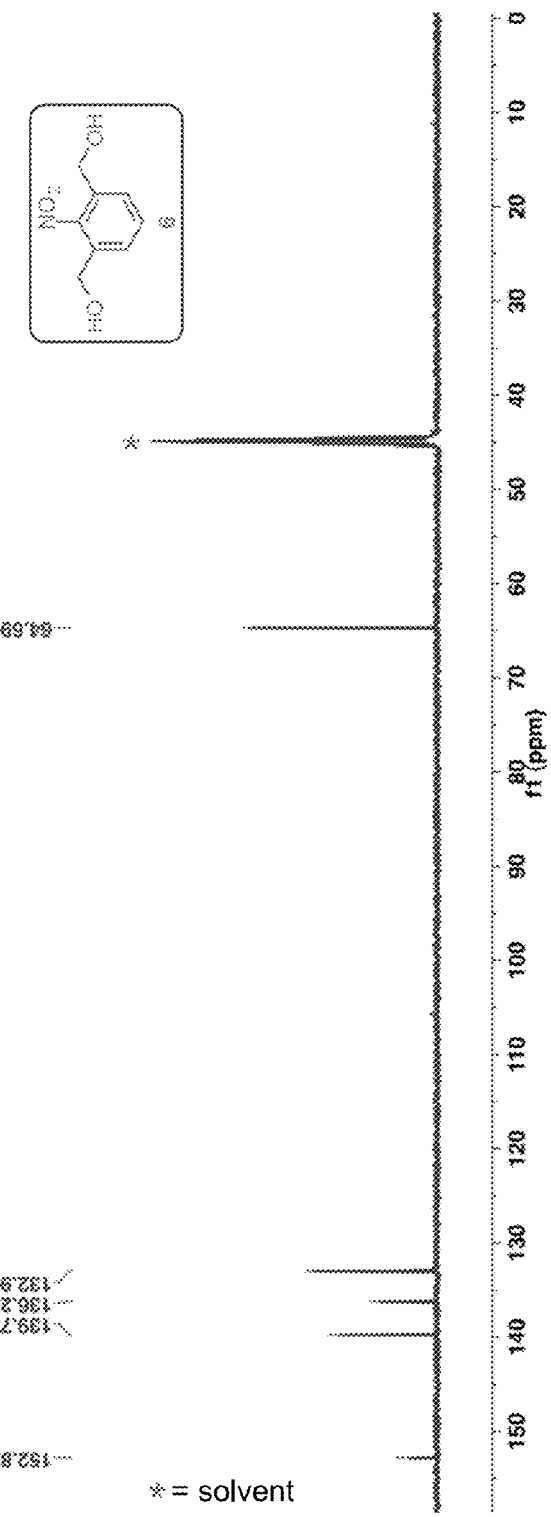
FIG. 17 is a $^{13}$C NMR spectrum (125 MHz, DMSO-d$_6$, δ ppm) of compound 6.

FIG. 16 shows a $^1H$ NMR and FIG. 17 shows a $^{13}C$ NMR of 2-nitro-1,3-benzenedimethanol 6.

Scheme 2 shows the photodegradation pathway of a particular symmetrical ester compound (Scheme 2A) and an unsymmetrical ester compound (Scheme 2B).

Analysis of $^1H$ NMR spectra revealed that the photocleavage of 7a and 7b was very efficient with excellent mass balance of 89 and 80 respectively. The ortho-nitrobenzyl protons resonance at 5.45 ppm was utilized as an NMR handle to monitor the reaction progress. As expected, we observed the formation of the nitrosoaldehyde 8 that was substantiated by the appearance of the aldehyde proton resonance at 9.17 ppm. The nitrosoaldehyde 8 underwent further decomposition to the give furan carboxylic acid 5 (based on the methylene proton resonance at ~4.82 ppm). As the model compound 7 was a symmetrically substituted substrate, we also evaluated the unsymmetrically substituted ester 9 and found that it underwent decomposition with

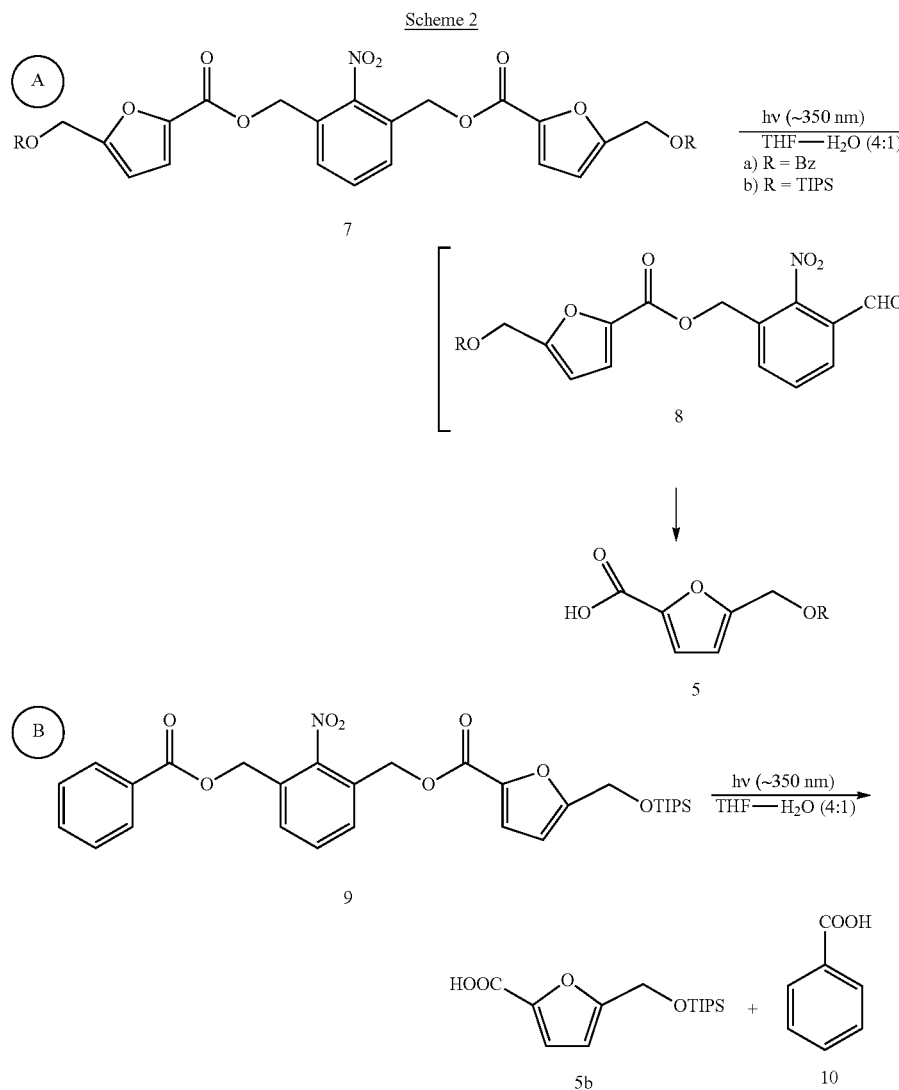

Figure 41:
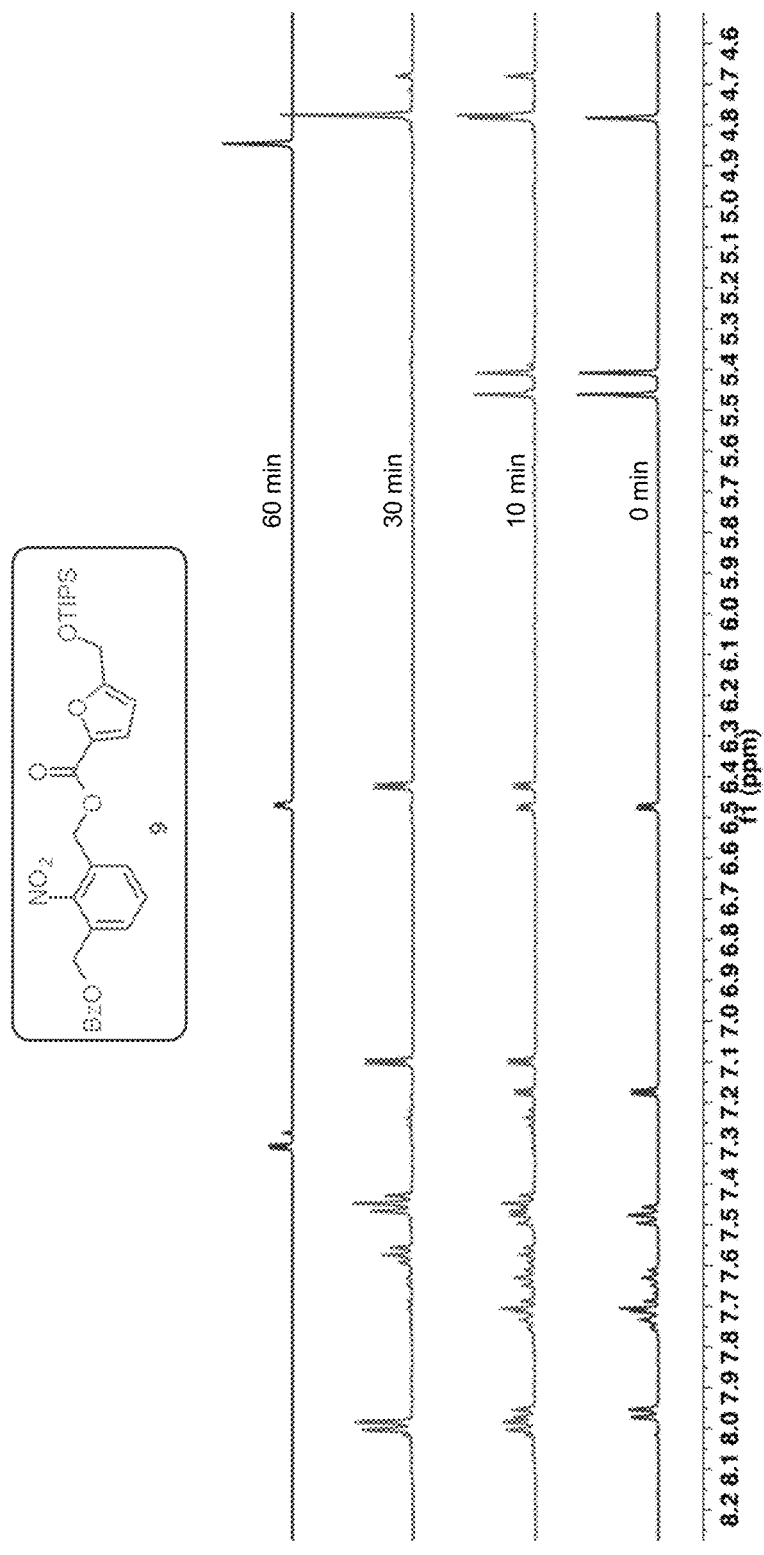
FIG. 41 shows $^1$H NMR spectra (400 MHz in THF-D$_2$O (4:1)) of compound 9 before irradiation (0 min), after 10 min irradiation, after 30 min irradiation and after 60 min irradiation.

Irradiation of illustrated compounds was carried out in a Rayonet reactor equipped with sixteen 14-Watt lamps (~350 nm). A known concentration of symmetrically substituted ester 7a or 7b in THF-$H_2O$ (7a: 1 mM or 0.1 mM and 7b=1 mM or 0.1 mM) was irradiated at ~350 nm (Scheme 2). The progress of the reaction was monitored every 30 min by both UV-Vis (see FIGS. 48a and 48b) and $^1H$-NMR spectroscopy.

equal effectiveness (FIG. 41). This proof of study with the model compounds clearly substantiated that the strategy of employing a nitrobenzyl trigger for the programmed degradation of oligomers/polymers derived from 5 (Scheme 1) was indeed viable as we could not only utilize monomers derived from biomass but also recover them with high fidelity.

Following are specific details regarding synthesis and characterization of the above noted compounds.

3.9 Synthesis of Ester Derivative 7a

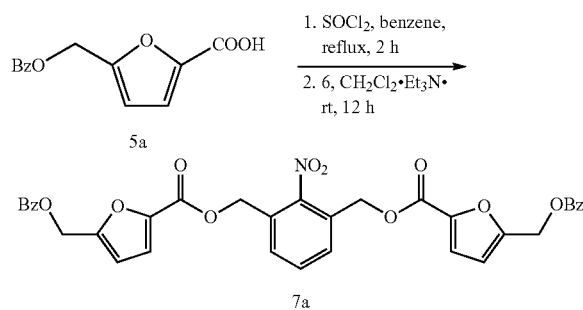

To a solution of acid 5a (2.46 g, 10 mmol, 1 equiv.) in benzene (15 mL), SOCl₂ (1.784 g, 15 mmol, 1.5 equiv. 1.1 mL) was added and refluxed for 2 h. Benzene and excess SOCl₂ was removed by distillation and dried under vacuum. The residue was dissolved in CH₂Cl₂ (15 mL) and added drop wise to a solution of 2-nitro-1,3-benzenedimethanol 6 (0.91 g, 5 mmol, 0.5 equiv.) and Et₃N (2.53 g, 25 mmol, 2.5 equiv., 3.5 mL) in CH₂Cl₂ (15 mL) and stirred at room temperature for 12 h. After the reaction, the mixture was quenched with water, extracted with CH₂Cl₂. The organic layer was dried over anhyd. Na₂SO₄ and the solvent was removed under reduced pressure. The crude product was purified by column chromatography hexanes-EtOAc mixture. The ester 7a was obtained as white solid. TLC condition—Rf=0.30 (60% hexanes: 40% ethyl acetate) for 7a (Yield=69%).

Figure 18:
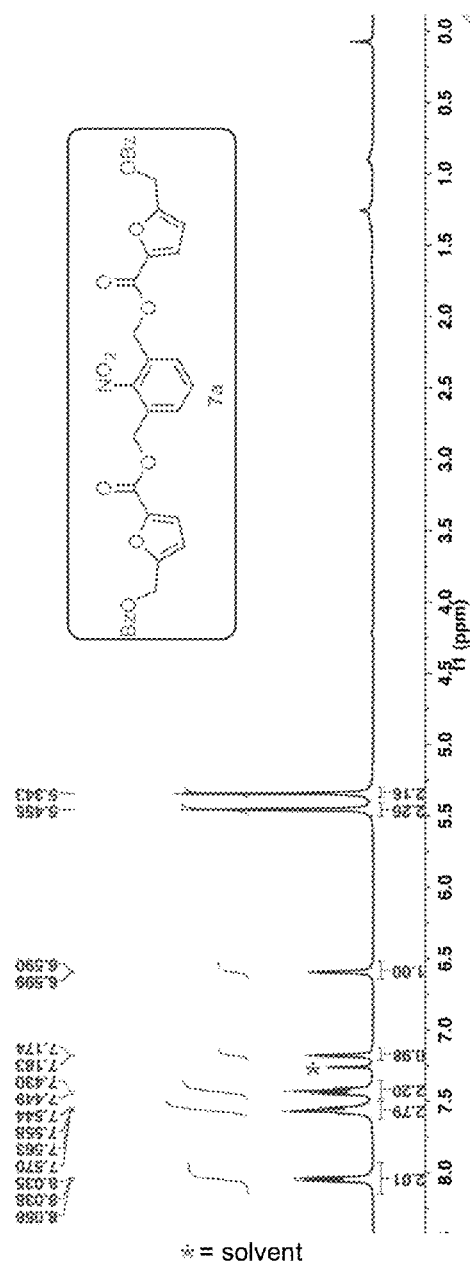
Figure 19:
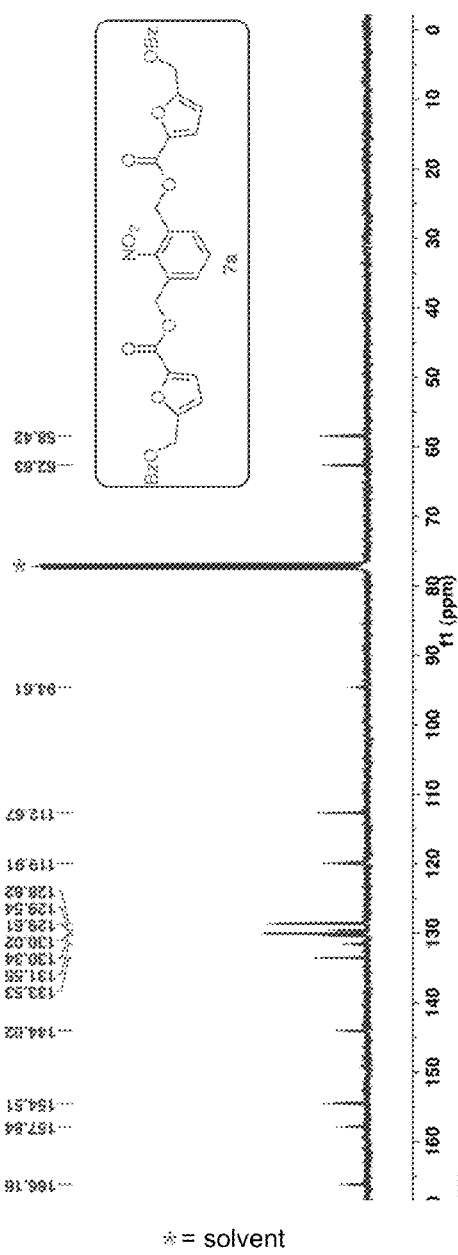
Figure 20:
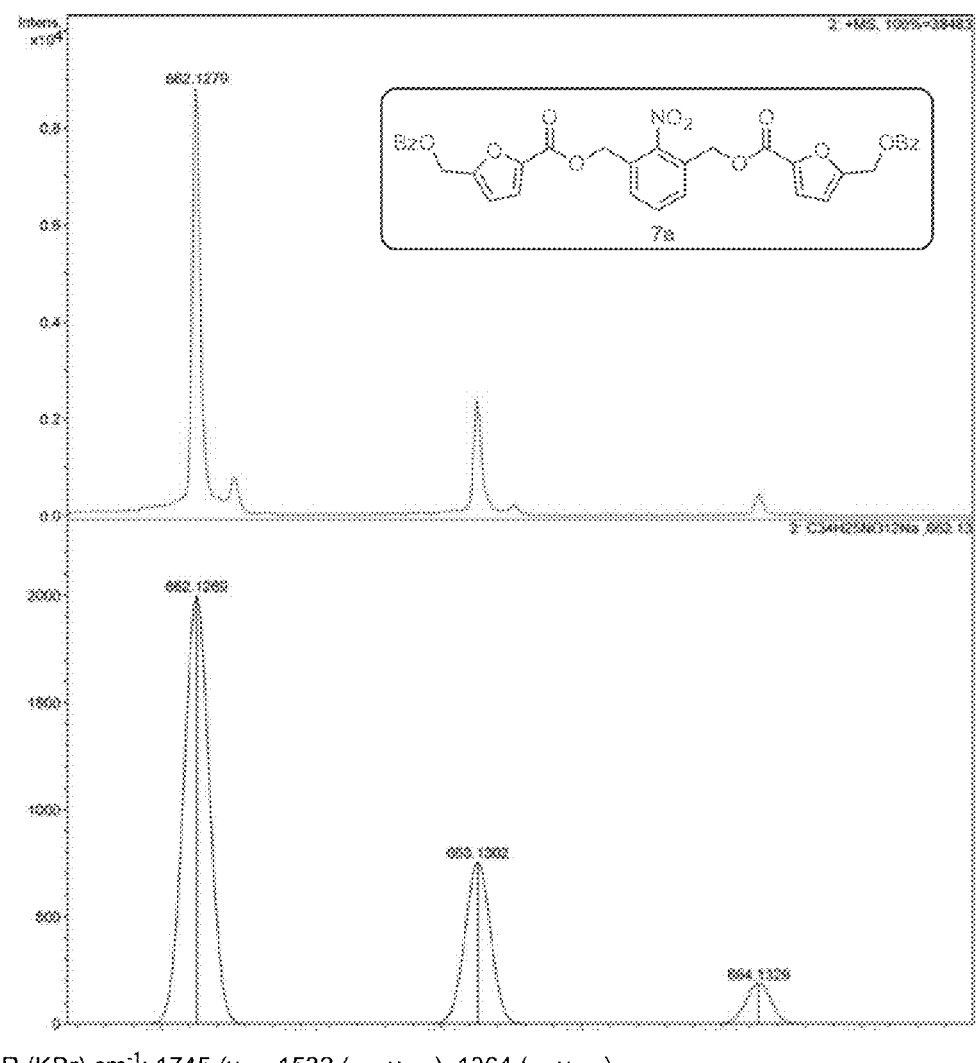

FIG. 18 shows a ¹H NMR, FIG. 19 shows a 13C NMR, and FIG. 20 shows ESI-MS data and FT-IR data of the ester derivative 7a.

3.10 Synthesis of Ester Derivative 7b

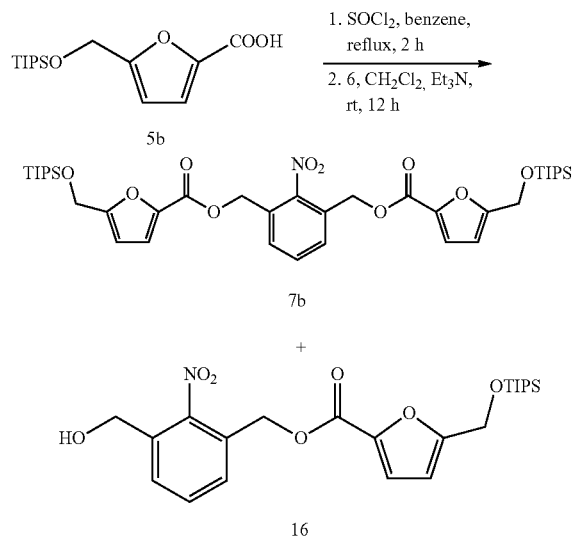

To a solution of 5b (0.149 g, 0.5 mmol, 1 equiv.) in benzene (5 mL) SOCl₂ (0.089 g, 0.75 mmol, 1.5 equiv. 54 μL) was added and refluxed for 2 h. Benzene and excess SOCl₂ was distilled and the residue was dried under vacuum. The residue was dissolved in CH₂Cl₂ (5 mL) and added drop wise to a solution of 2-nitro-1,3-benzenedimethanol 6 (0.046 g, 0.25 mmol, 0.5 equiv.) and Et₃N (0.126 g, 1.25 mmol, 2.5 equiv., 0.174 mL) in CH₂Cl₂ (5 mL) and stirred for 12 h at room temperature. After the reaction, the mixture was quenched with water, extracted with CH₂Cl₂. The organic layer was dried over anhyd. Na₂SO₄ and concentrated under reduced pressure. Crude product was purified by column chromatography using hexanes-EtOAc mixture. The ester 7b was obtained as colorless viscous oil and monoester 16 was obtained as minor product. Compound 7b: TLC condition—Rf=0.60 (60% hexanes: 40% ethyl acetate) for 7b (Yield=59%). Compound 16: TLC condition—Rf=0.50 (60% hexanes: 40% ethyl acetate) for 16 (Yield=10%).

Figure 21:
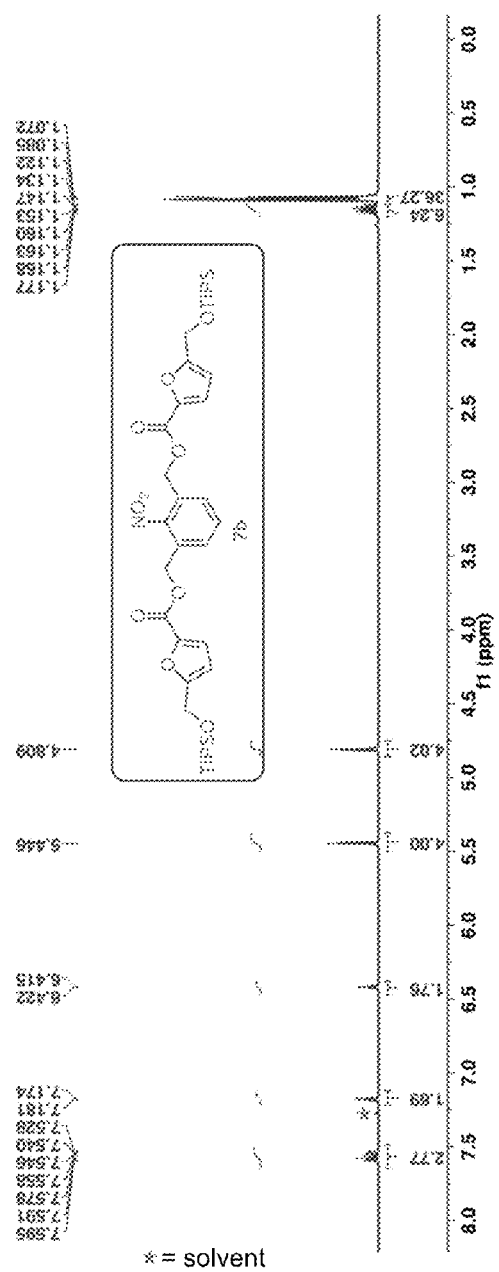
FIG. 21 is a $^1$H NMR spectrum (500 MHz, CDCl$_3$, δ ppm) of compound 7b.
Figure 22:
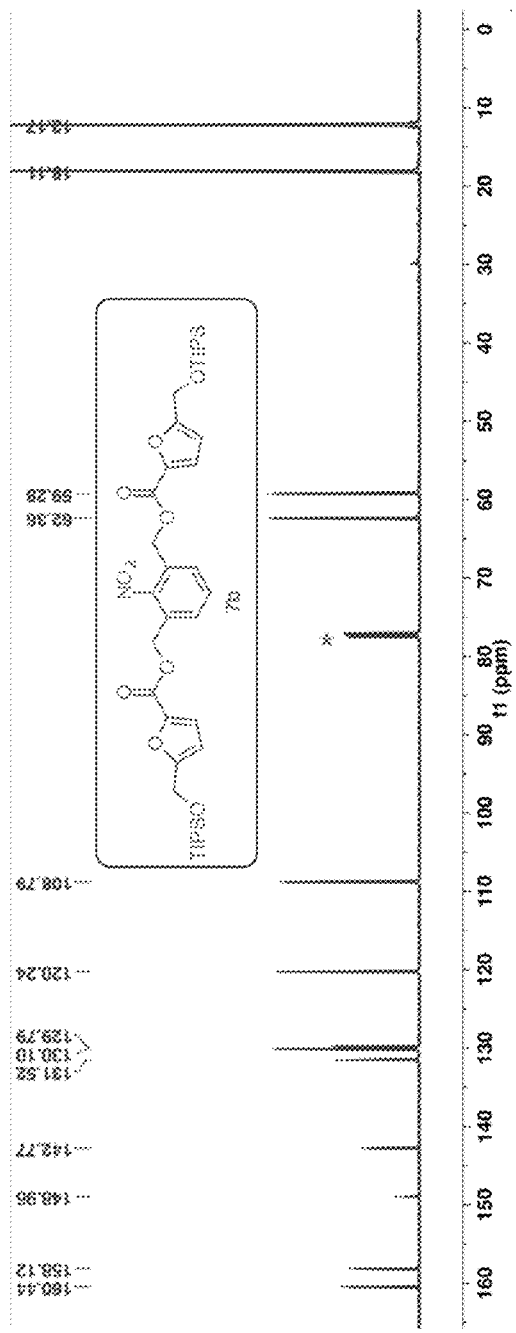
FIG. 22 is a $^{13}$C NMR spectrum (125 MHz, CDCl$_3$, δ ppm) of compound 7b.
Figure 23:
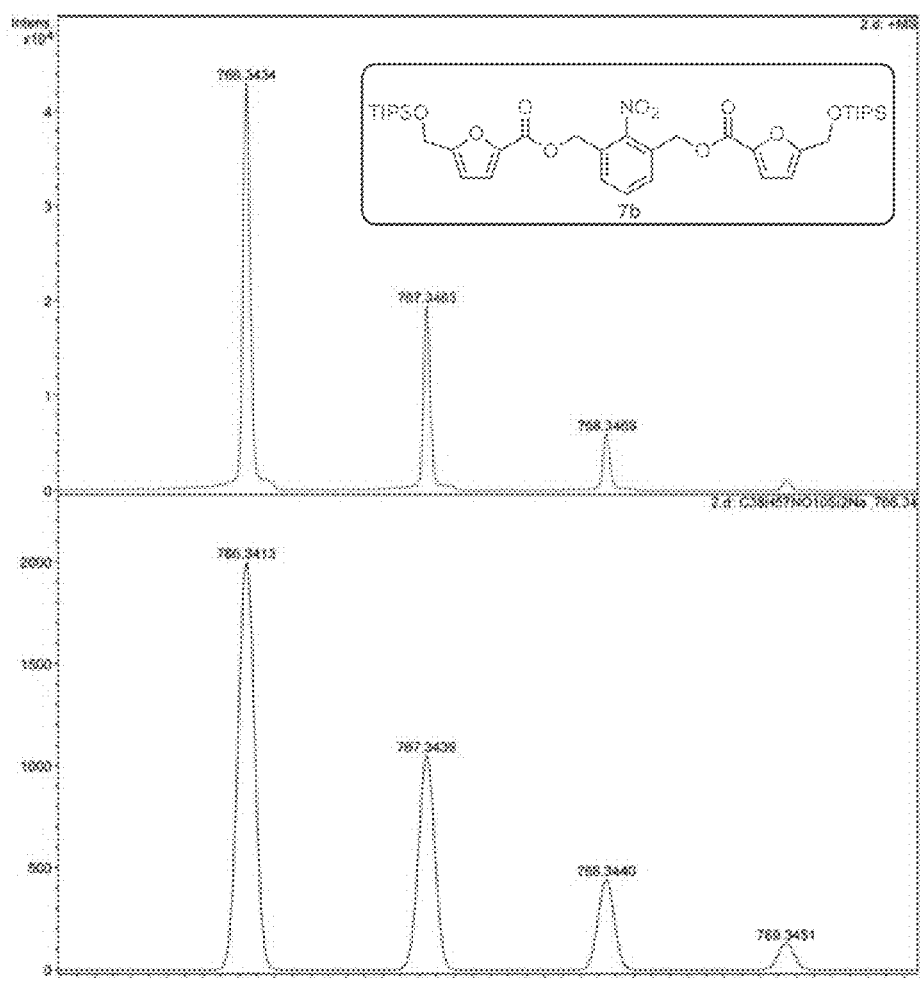
FIG. 23 is ESI-MS data of compound 7b.
Figure 24:
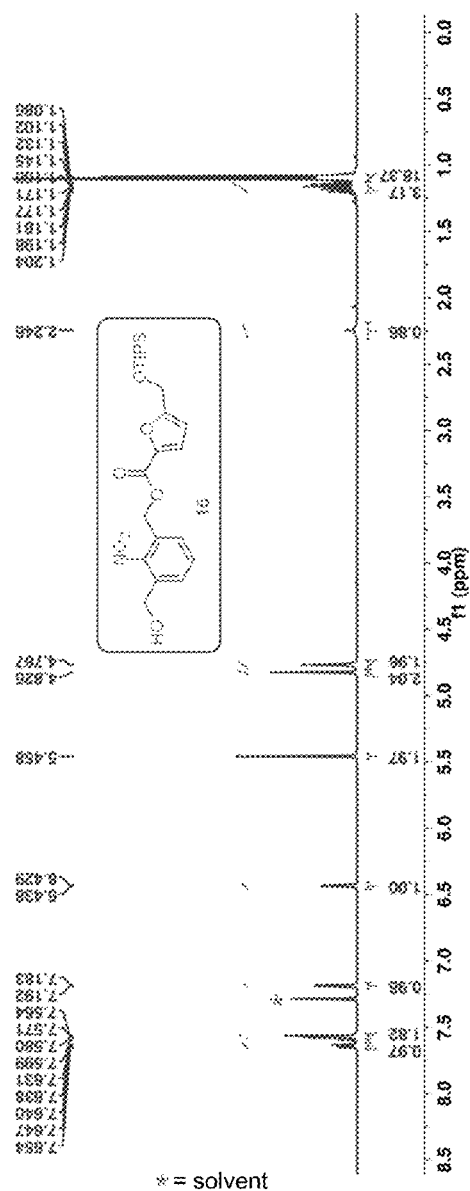
FIG. 24 is a $^1$H NMR spectrum (400 MHz, CDCl$_3$, δ ppm) of compound 16.
Figure 25:
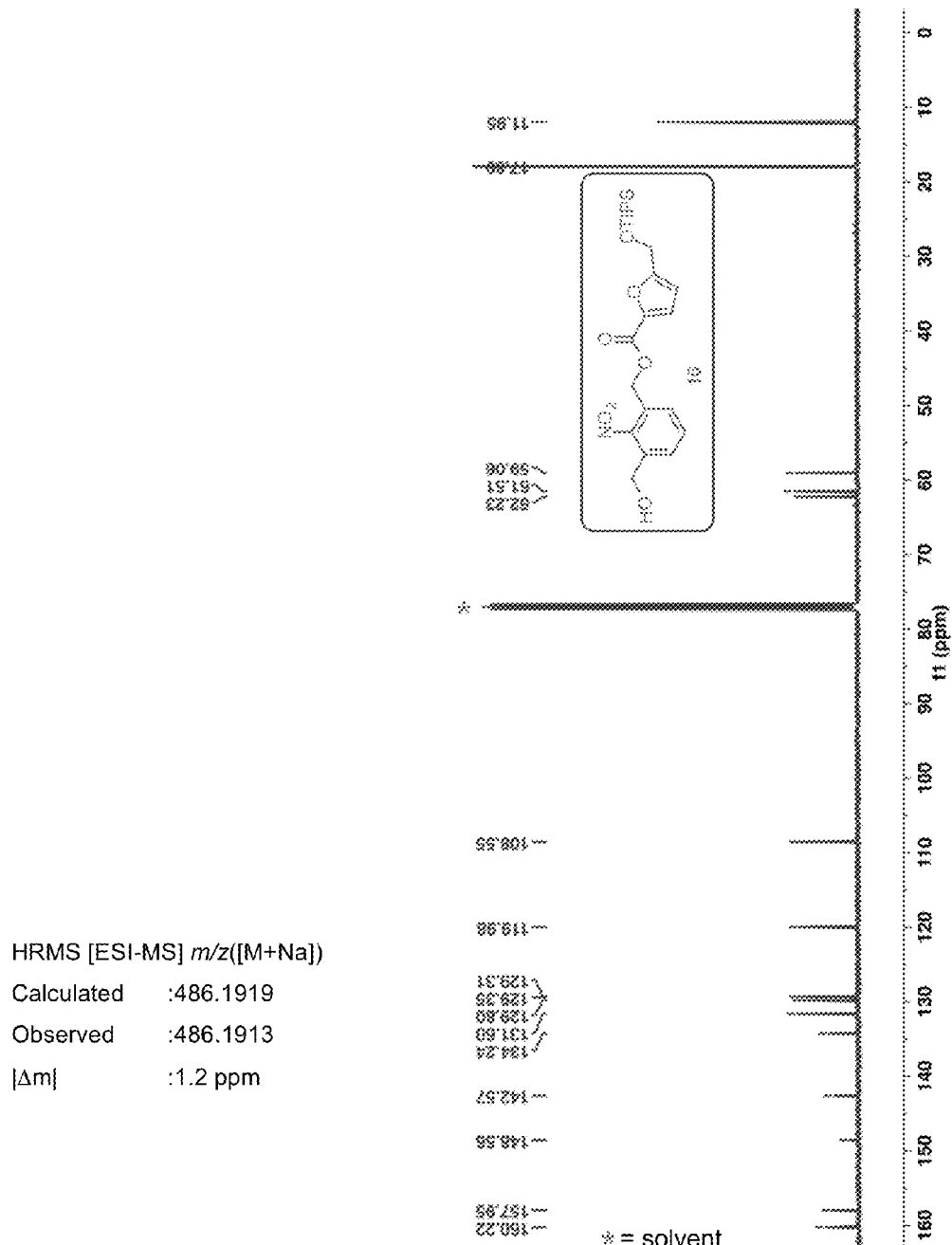
FIG. 25 is a $^{13}$C NMR spectrum (100 MHz, CDCl$_3$, δ ppm) and ESI-MS data of compound 16.

FIG. 21 shows 1H NMR, FIG. 22 shows 13C NMR and FIG. 23 shows ESI-MS data of the ester derivative 7b. FIG. 24 shows 1H NMR and FIG. 25 shows 13C NMR and ESI-MS data of monoester 16b.

3.11 Synthesis of Ester Derivative 9

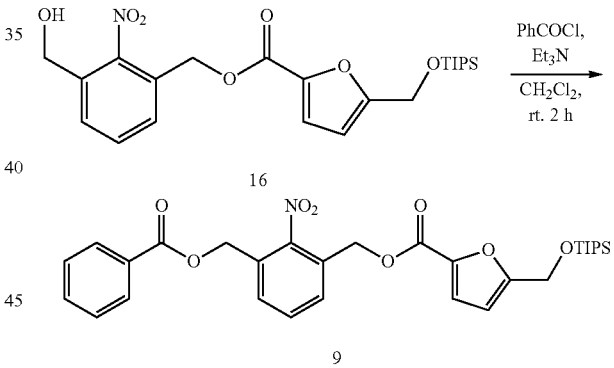

To a solution of 16 (0.463 g, 1 mmol, 1 equiv.) in CH2Cl2 (25 mL), Et₃N (0.151 g, 1.5 mmol, 1.5 equiv., 0.21 mL) was added followed by drop wise addition of benzoyl chloride (0.168 g, 1.2 mmol, 1.2 equiv., 0.14 mL). The reaction mixture was stirred for 2 h at room temperature. After the reaction, the mixture was quenched with satd. NaHCO₃ solution, extracted with CH₂Cl₂. The combined organic layer was dried over anhyd. Na₂SO₄ and concentrated under reduced pressure. The crude product was purified by column chromatography using hexanes:EtOAc mixture. The pure compound 9 was obtained as colorless viscous oil (which solidifies upon cooling). TLC condition—Rf=0.60 (70% hexanes: 30% ethyl acetate) for 9 (Yield=93%).

Figure 26:
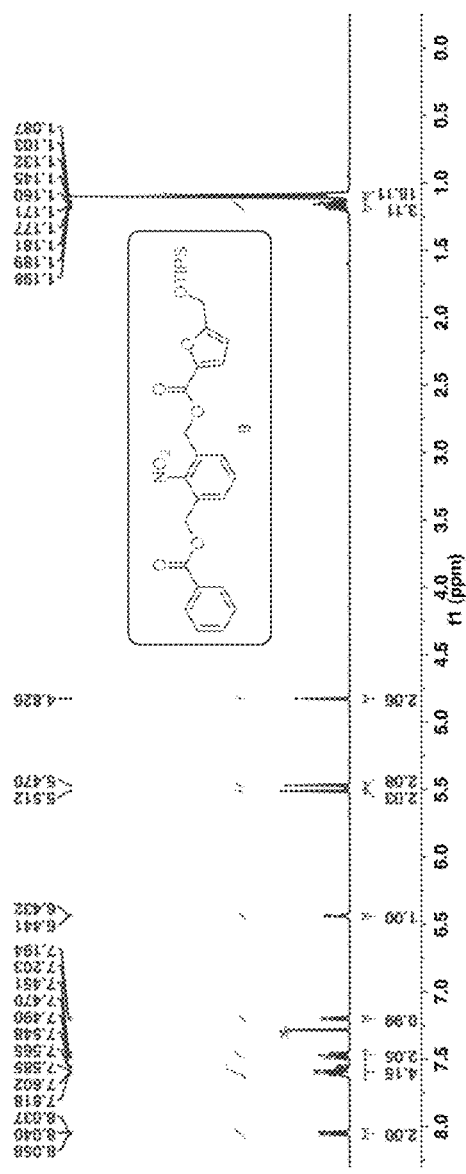
FIG. 26 is a $^1$H NMR spectrum (400 MHz, CDCl$_3$, δ ppm) of compound 9.
Figure 27:
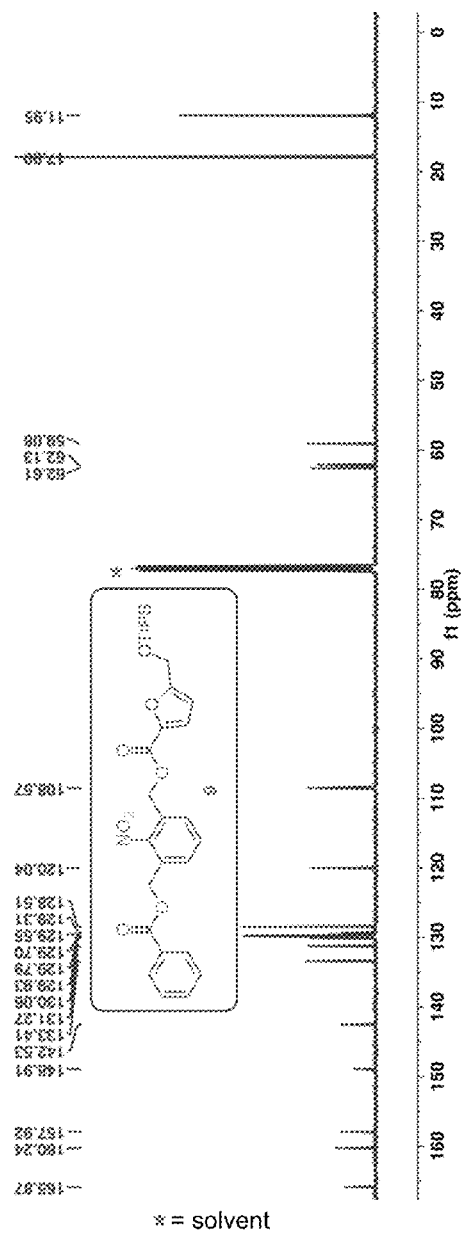
FIG. 27 is a $^{13}$C NMR spectrum (100 MHz, CDCl$_3$, δ ppm) of compound 9.
Figure 28:
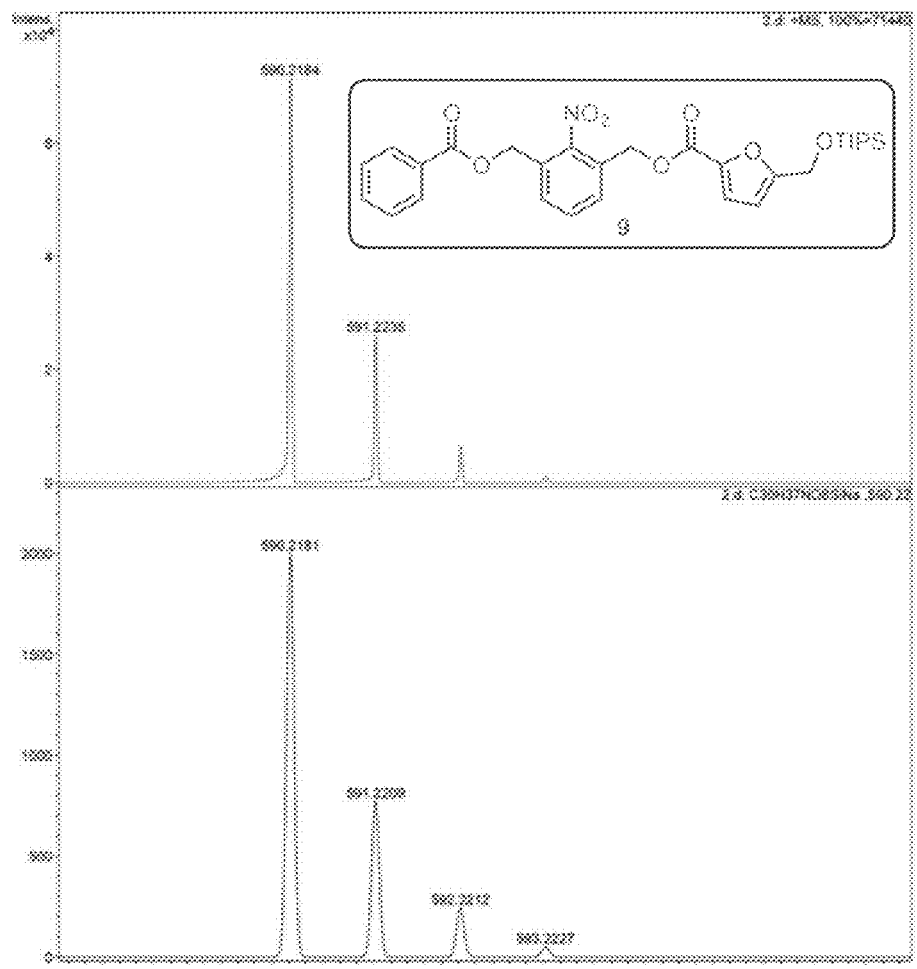
FIG. 28 is ESI-MS data of compound 9.

FIG. 26 shows 1H NMR, FIG. 27 shows 13C NMR and FIG. 28 shows ESI-MS data of ester derivative 9

Scheme 3. Synthesis of polymer/oligomer 11 derived from biomass.

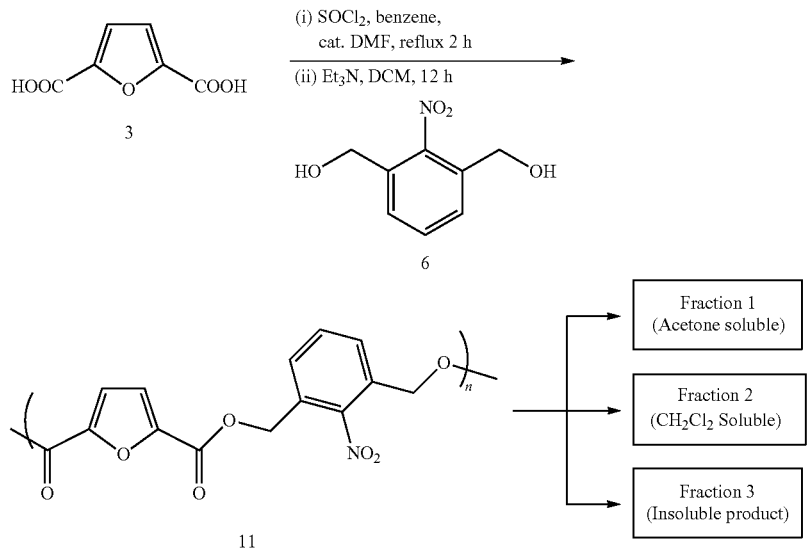

With the knowledge gained through the photocleavage of model compounds, we proceeded to synthesize polymer/oligomers from FDCA 3 that featured the nitrobenzyl functionality to evaluate the efficiency of photocleavage as well as the recovery of the monomer 3. In a one-pot reaction, 3 was converted to the corresponding acid chloride with thionyl chloride and reacted with nitrobenzyl phototrigger 6 to obtain a pale brown solid (Scheme 3). Following are specific details regarding synthesis and characterization of the polymer 11.

3.12 Synthesis of Polymer/Oligomer 11

Scheme S12: Synthesis of polymer/oligomer 11

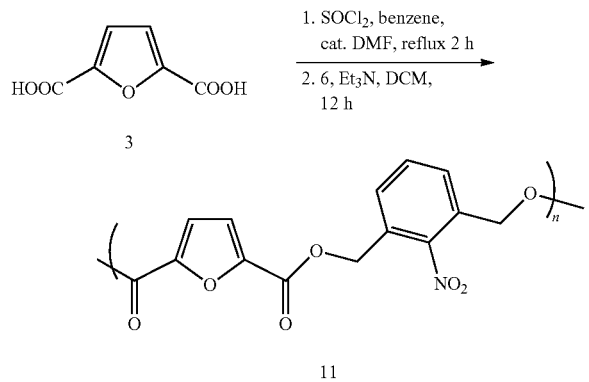

To a solution of 3 (0.312 g, 2 mmol, 1 equiv.) in dry benzene (15 mL), SOCl$_2$ (0.713 g, 6 mmol, 3 equiv. 0.5 mL) and DMF (0.2 mL) were added and was refluxed for 2 h. After 2 h, benzene and excess SOCl$_2$ were distilled and dried under vacuum. The residue was dissolved in CH$_2$Cl$_2$ (10 mL) and added drop wise to a solution of 2-nitro-1,3-benzenedimethanol 6 (0.183 g, 1 mmol, 0.5 equiv.) and Et$_3$N (0.606 g, 6 mmol, 3 equiv., 0.8 mL) in CH$_2$Cl$_2$ (10 mL) and continued stirring for 12 h at room temperature. After the reaction, pale brown solid was precipitated. It was filtered and washed with methanol (3×~25 mL) to remove any unreacted monomer. Followed by washing with Dichloromethane (2×20 mL) and acetone (2×20 mL) to remove low molecular weight oligomer. The insoluble material obtained was pale yellow solid (11) in 0.175 g. It was insoluble in common organic solvents such as DMSO, DMF, CH$_2$Cl$_2$, EtOAc, MeOH, THF and CHCl3. It was characterized by 1H, 13C NMR in DMSO-d6 (the suspension was heated at 60-80° C. to make it completely soluble), IR spectroscopy, GPC, TGA, DSC and PXRD. For GPC analysis, the compound was suspended in THF and sonicated for 5 h at room temperature. The residue was filtered and the supernatant was injected in the GPC. Yield: 0.175 g (insoluble portion). IR (KBr) cm-1: 1739 (vC═O), 1529 (asym. vNO2), 1367 (sym. NO2), 1129 (vC—O).

% Crystallinity of compound 11 was determined by PXRD data It is calculated to be 20.26% with respect to Cristobalite (98% crystallinity) as standard.

The above experiment was repeated at least three times to check the reproducibility of the crystallinity of the product formed. PXRD patterns are almost identical (Figure S7).

% Crystallinity of compound 11 synthesized for second and third time are found to be 19.93% and 21.47% respectively.

Figure 29:
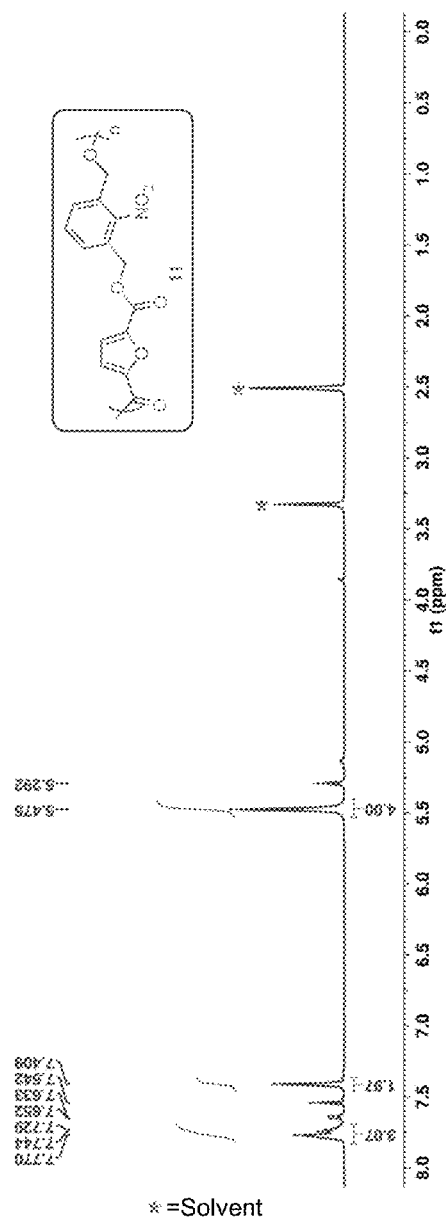
FIG. 29 is a $^1$H NMR spectrum (400 MHz, DMSO-d$_6$, δ ppm) of compound 11.
Figure 30:
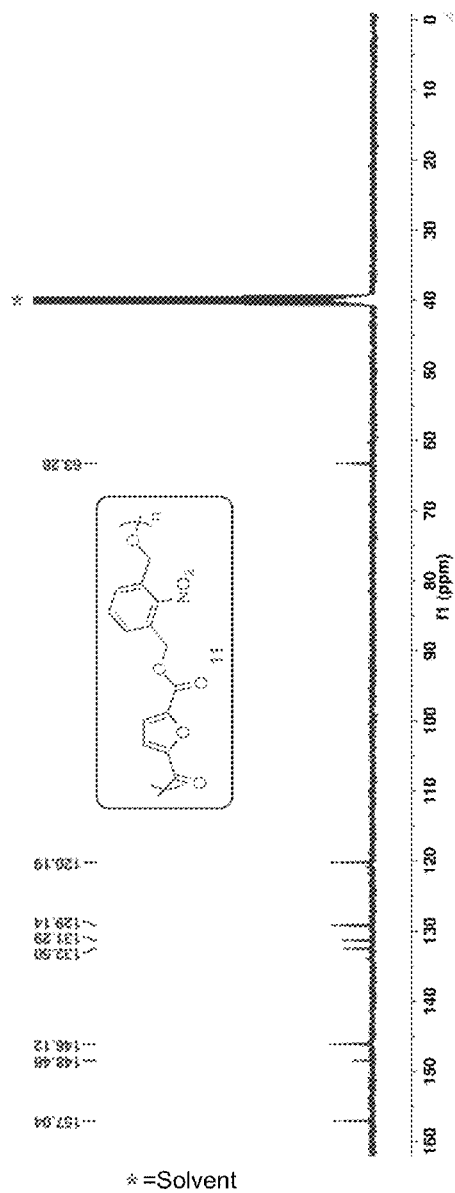
FIG. 30 is a $^{13}$C NMR spectrum (100 MHz, DMSO-d$_6$, δ ppm) of compound 11.

FIG. 29 shows 1H NMR and FIG. 30 shows 13C NMR of polymer/oligomer 11.

Figure 51:
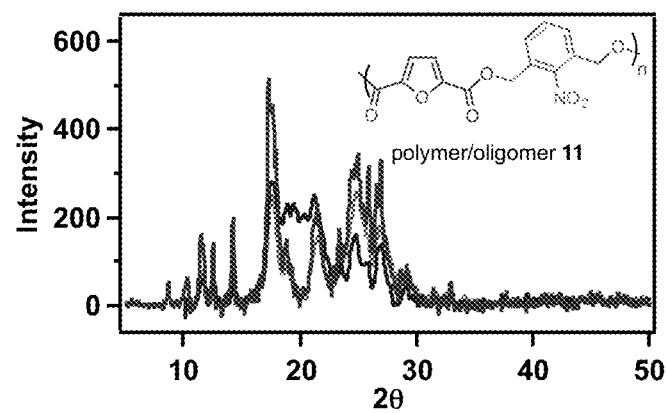
FIG. 51 shows a stacked powder XRD (PXRD) pattern of three separately synthesized batches of polymer/oligomer 11.

The insoluble product was washed with methanol to remove any unreacted monomer. The product was then triturated followed by the addition of acetone and CH$_2$Cl$_2$ to remove low molecular weight oligomers. The left over insoluble solid was then washed with methanol and dried under reduced pressure and was characterized by FT-IR spectroscopy, GPC, powder X-ray diffraction (PXRD) (FIG. 51), NMR spectroscopy, TGA and DSC. As the residue was partially soluble in THF at room temperature, the material was suspended in THF and sonicated for 5 h. The solution was filtered and the supernatant was analysed by GPC (FIG.

Figure 31A:
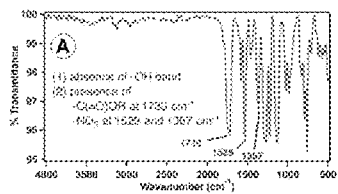
FIGS. 31A to 31F are for the characterization of compound 11: FTIR spectrum of compound 11 derived from biomass (FIG. 31A), a gel permeation chromatography (GPC) trace of compound 11 derived from biomass (FIG. 31B), a GPC trace of compound 11 from recycled monomer (FIG. 31C), a thermogravimetric analysis (TGA) of compound 11 from recycled monomer (FIG. 31D), a differential scanning calorimetry (DSC) of compound 11 from recycled monomer (FIG. 31E), and powder X-ray diffraction (XRD) of compound 11 (FIG. 31F).
Figure 31B:
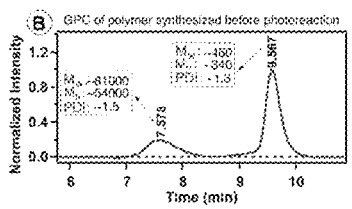

31B). shows that the material is a mixture of polymer ($M_w$=81000; $M_n$=54000 and PDI=1.5) and oligomer ($M_w$=450; $M_n$=340 and PDI=1.3). The synthetic procedure for accessing the polymer/oligomer 11 was repeated for reproducibility and characterized by PXRD (vide infra). Inspection of FT-IR spectrum of the pale brown solid (FIG. 31A) revealed a strong vibration band at 1739 cm$^{-1}$ indicating an ester functionality. In addition, the presence of the nitro group was unequivocally established by its characteristic asymmetric and symmetric stretching at 1529 and 1367 cm$^{-1}$ respectively. All these clearly pointed out that the insoluble solid material 11 was polymer/oligomer between 3 and 6.

Figure 31C:
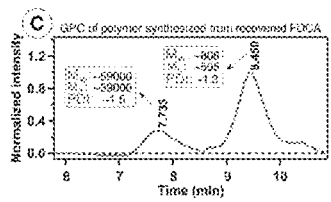
Figure 31D:
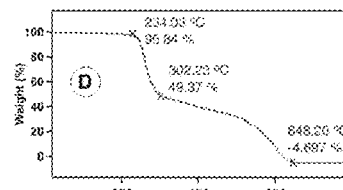
Figure 31E:
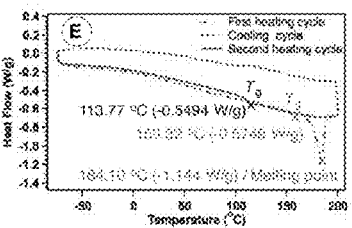
Figure 31F:
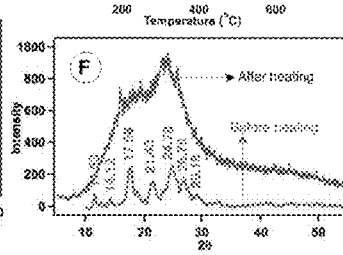

To further characterize the material obtained from the condensation of 3 and 6, we made a completely soluble solution of 11 by heating a suspension in DMSO-d6 at 60-80° C. as it was insoluble in common organic solvents (CHCl$_3$, EtOAc, MeOH) at room temperature. The solution was analyzed by H-NMR spectroscopy that showed aromatic resonances corresponding to the furan and phenyl functionalities. In addition, two singlet resonances at 5.48 ppm and 5.29 ppm indicated distinct benzylic functionalities with a ratio ~11:1. The mixture of polymers/oligomers is consistent with the NMR studies that showed two singlet resonances for the benzylic protons once again reflecting the two distinct oligomer/polymer present in our system (consistent with GPC data). TGA analysis of polymer/oligomer 11 showed that it was thermally stable with no considerable weight loss up to 234° C. (FIG. 31D). When the temperature was increased to 302° C., a 50% weight loss was observed which is likely due to decomposition of the polymer/oligomer. Decomposition of the remaining residue was complete at 648° C. DSC analysis (FIG. 31E) of polymer/oligomer 11 showed a glass transition temperature ($T_g$) at 159° C. followed by melting at 184° C. during the first heating cycle suggesting that polymer/oligomeric 11 was a mixture of amorphous and crystalline states. The cooling cycle showed a slight recrystallization but was not sharp as expected due to the lack of crystallinity in the oligomer. The second heating cycle showed more discernible $T_g$ at 113° C. suggesting a mostly amorphous oligomer. To substantiate this observation we analysed the synthesized oligomer/polymer 11 by powder XRD diffraction (PXRD). Closer inspection of the PXRD data (FIG. 31F) indicated that 11 as synthesized had sharp peaks (2θ value) and the percentage crystallinity was estimated to be 24.34% using Cristobalite (SiO$_2$) as the reference standard. Upon heating the sample to 200° C. and cooling 11, there was a complete loss of crystallinity with a broad peak in the PXRD indicating that the sample was likely amorphous (FIG. 31F).

While 11 was not soluble in common organic solvents, we were interested in evaluating its photodegradability and in gauging the amount of the monomer that could be recovered for recycling. Photodegradation of 11 formed 3 as seen below:

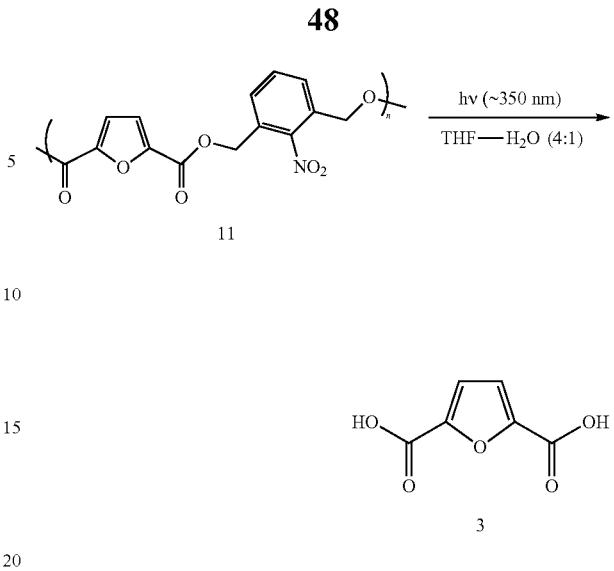

Figure 32:
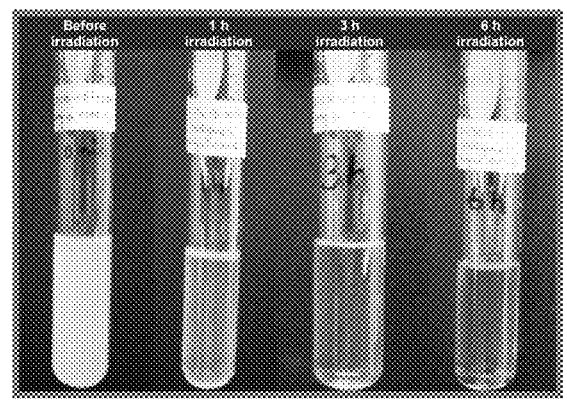
FIG. 32 is a photographic image of the polymer/oligomer 11 before irradiation, after being irradiated for 1 hour, after being irradiated for 3 hours, and after being irradiated for 6 hours.

The photodegradation of 11 was evaluated as a suspension in a 4:1 THF-H$_2$O mixture (FIG. 32) After 6 h of irradiation the sample was concentrated and the residue was analyzed by 1H NMR spectroscopy using triphenylmethane (10$^{-2}$ M in CHCl$_3$, 1 mL) as an internal standard. Analyzing the 1H and 13C-NMR spectrum of 6 h irradiated sample showed the presence of FDCA (by comparing the spectra of authentic FDCA sample) and the recovery of FDCA was found to be 40±5%. The experiments were performed with two different internal standards (triphenylmethane and maleic acid) and the results are an average of three runs.

Figure 43:
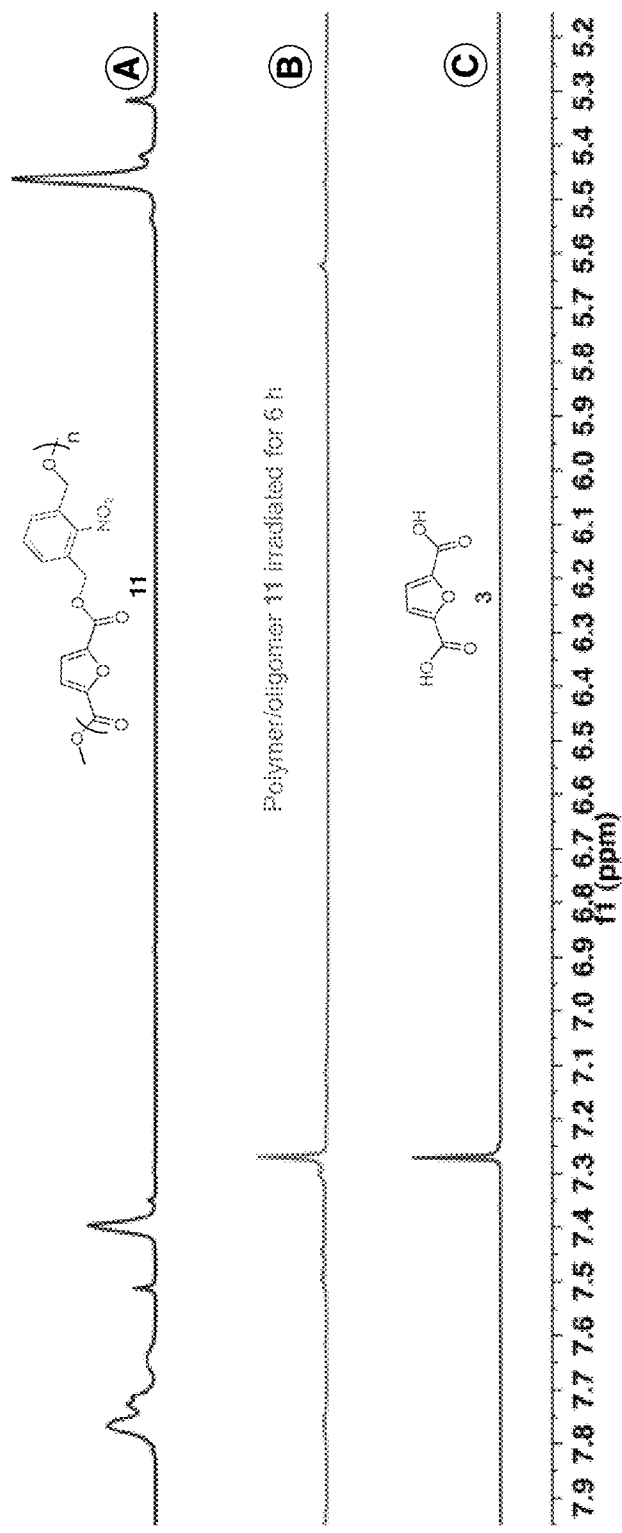
FIG. 43 shows $^1$H NMR spectra (400 MHz in DMSO-d$_6$) of compound 11 before irradiation, after 6 h irradiation and compound 3.
Figure 44:
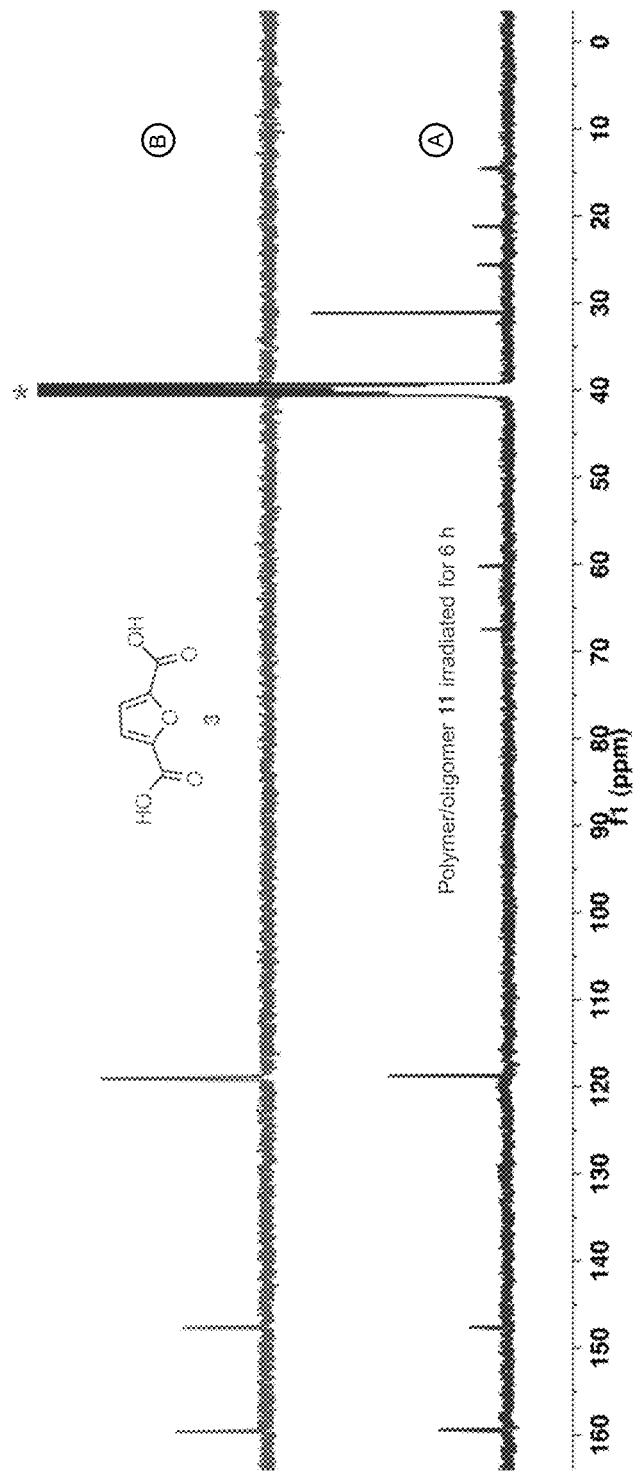
FIG. 44 shows $^{13}$C NMR spectra (125 MHz in DMSO-d$_6$) of compound 11 after 6 hr irradiation and compound 3.

Irradiation of the slurry at ~350 nm resulted in a slightly turbid solution after 1 h and the solution became completely transparent after 3 h of light exposure. The irradiated samples were analysed by NMR spectroscopy that showed complete decomposition of 11 to give the monomer, FDCA 3 as seen in FIGS. 43 and 44. FIG. 43 shows a 1H NMR spectra of polymer/oligomer 11 before radiation (trace A) and after irradiation (trace B) and of FDCA 3 for the sake of comparison. FIG. 44 a 13C NMR spectra of polymer/oligomer 11 after 6 h irradiation (trace A) and of FDCA 3 (trace B) for the sake of comparison.

Figure 33:
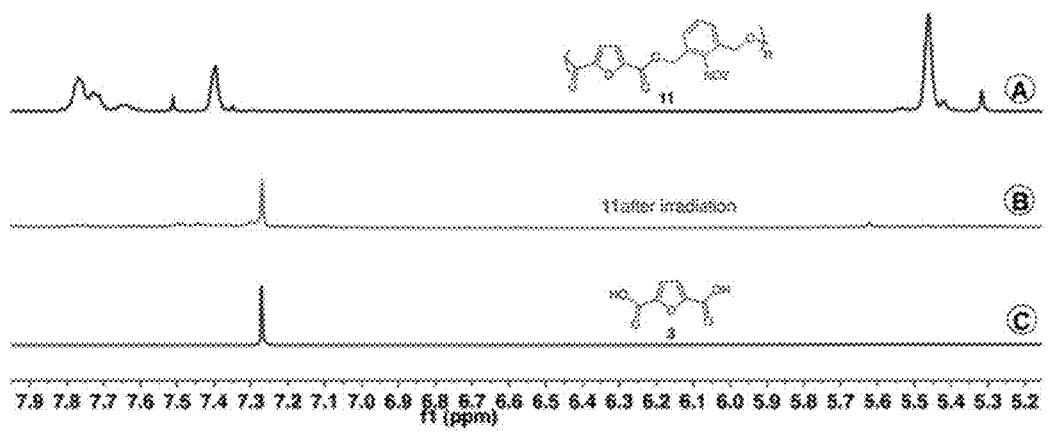
FIG. 33 shows $^1$H NMR spectra (500 MHz, DMSO-d$_6$, δ ppm) of polymer 11 before irradiation and after irradiation, and authentic FDCA 3.
Figure 45:
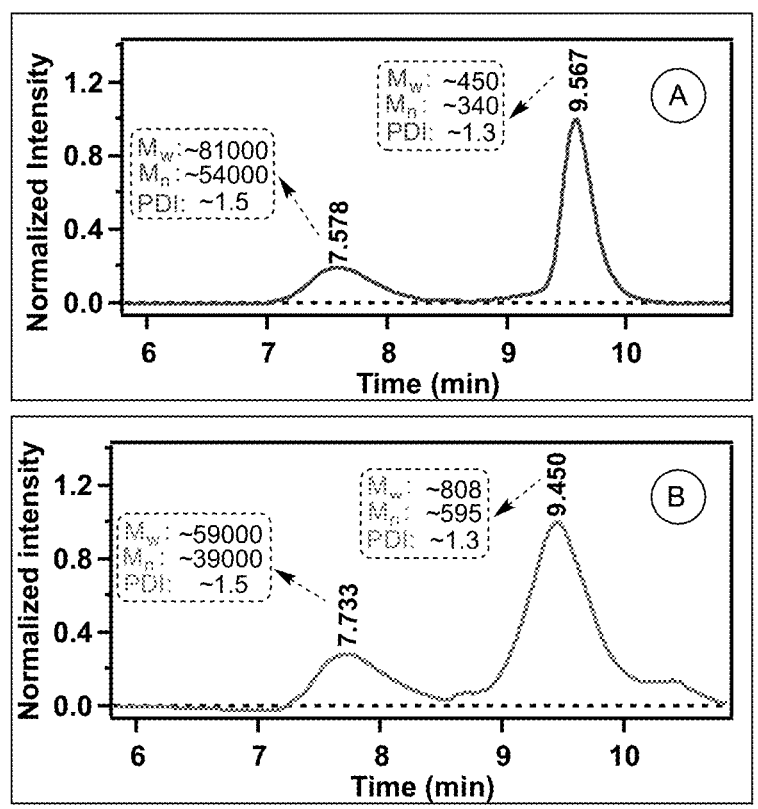
FIG. 45 shows GPC traces of polymer/oligomer 11 synthesized from monomer derived from biomass (A) and synthesized using recovered FDCA (B).
Figure 46:
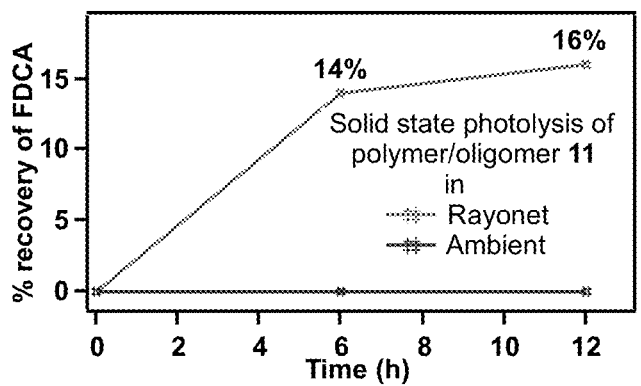
FIG. 46 shows the recovery of FDCA upon solid-state irradiation (Rayonet irradiation—top line (red), and ambient light irradiation—bottom line (blue)). Recovery was monitored by $^1$H NMR spectroscopy.

The formation of the parent monomer was further confirmed by comparing the NMR spectra of the sample after irradiation with an authentic sample of 3 synthesized by an independent route (FIG. 33). Irradiation of 11 was also evaluated in the solid state under UV light that showed slow degradation, when compared to slurry irradiation where complete degradation was observed (FIG. 46). Based on recovery after irradiation as a slurry (THF/H$_2$O: 4:1), 40(±5)% of the monomer 3 was isolated. We were also successful in recycling the recovered monomer 3 back to the polymer (FIG. 31C) that highlighted the viability and practicality of our strategy. FIG. 45a shows the GPC trace of polymer/oligomer 11 synthesized from monomers derived from biomass and FIG. 45b is the GPC trace of the polymer/oligomer 11 synthesized using recovered FDCA.

Scheme 5. Synthesis and photocleavage of co-polymer 12.

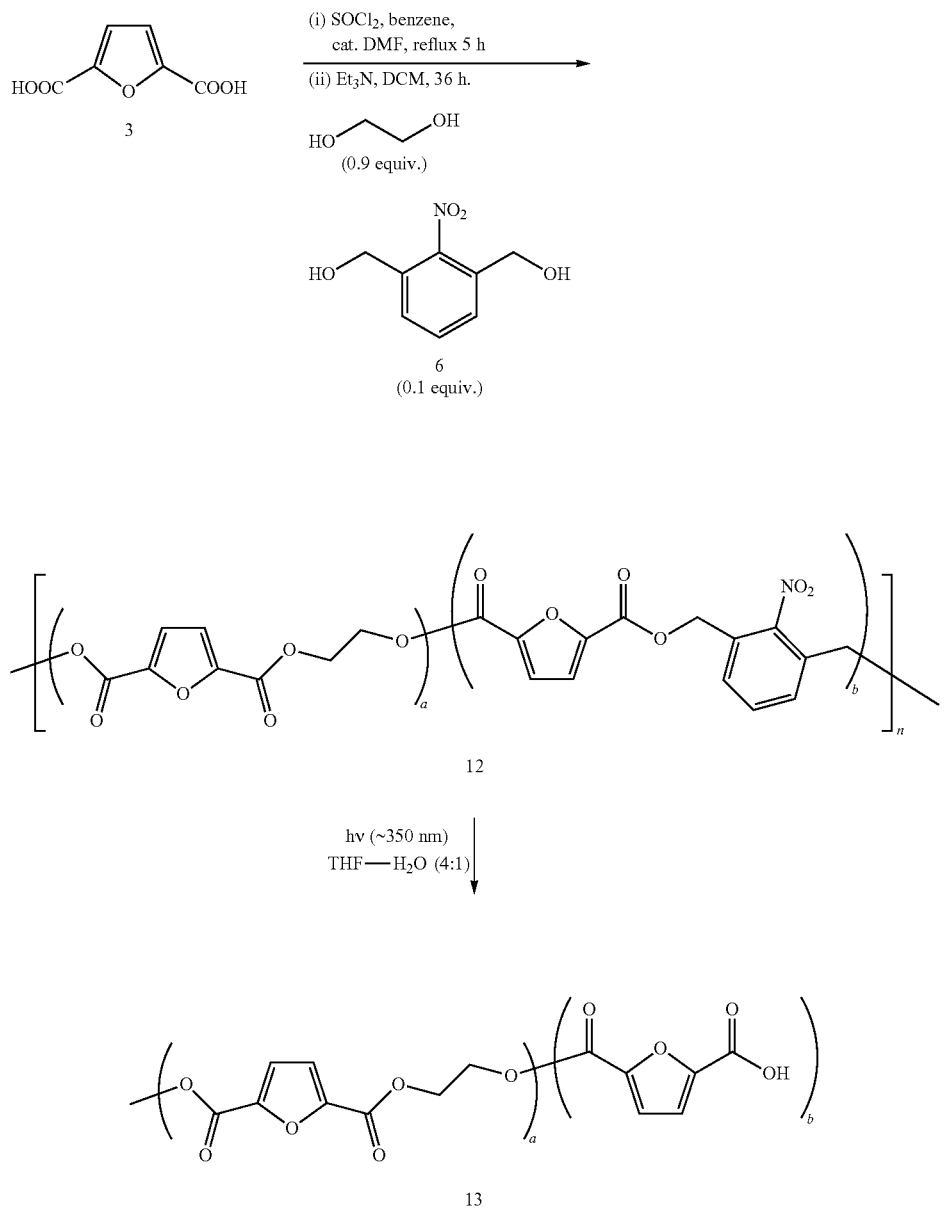

To evaluate if our strategy can be extended to co-polymers incorporating glycols other than the phototrigger 6, we synthesized co-polymer 12. In a single pot reaction (Scheme 5), FDCA 3 was converted to the corresponding acid chloride with thionyl chloride and subsequently reacted with mixture of ethylene glycol (0.9 equiv.) and 6 (0.1 equiv.). After the reaction was complete, methanol was added to the reaction that resulted in the co-polymer 12, which was characterized as before.

Further details regarding synthesis and characterization of the copolymer/oligomer 12 can be found below.

3.13 Synthesis of Co-Polymer/Oligomer 12

Scheme S13: Synthesis of co-polymer/oligomer 12

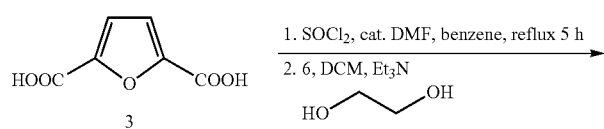

-continued

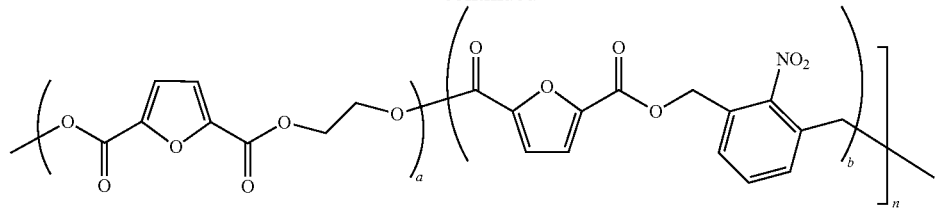

12

To a solution of 2,5-furandicarboxylic acid (FDCA) 3 (0.468 g, 3 mmol, 1 equiv.) in dry benzene (15 mL), SOCl$_2$ (2.14 g, 18 mmol, 6 equiv. 1.3 mL) and catalytic amount of DMF (0.2 mL) were added and refluxed for 3 h. After the reaction, benzene and excess SOCl$_2$ were distilled and dried under reduced pressure. The residue obtained was dissolved in CH$_2$Cl$_2$ (10 mL) and added drop wise to a solution of 2-nitro-1,3-benzenedimethanol 6 (0.055 g, 0.3 mmol, 0.1 equiv.), ethylene glycol (0.167 g, 2.7 mmol, 0.9 equiv., 0.15 mL) and Et$_3$N (0.91 g, 9 mmol, 3 equiv., 1.25 mL) in CH$_2$Cl$_2$ (10 mL) and continued stirring for 36 h at room temperature. After the reaction, the mixture was concentrated under reduced pressure to obtain crude product as pale brown solid. It was then washed with excess of water (2×~200 mL) and methanol (2×~50 mL) and dried under vacuum to get off-white solid in 260 mg. The obtained solid was characterized by 1H, 13C NMR IR spectroscopy, GPC, TGA, DSC and PXRD.

For GPC analysis, the compound was suspended in THF for 5 h at room temperature. The residue was filtered and the supernatant was injected in the GPC.

ESI-MS: Sample was dispersed in THF and sonicated for 5 min and allow to settle down for 2 h. The supernatant solution was analyzed by ESI-MS. A series of peaks appeared in the range of m/z 531-839 as binomial series with difference of 44 between every peak which is typical for ethylene glycol unit.

[ESI-MS] m/z: 531.4567, 575, 4870, 619.5200, 663, 5516, 707.5837, 751.6145, 795.6462, 839, 6800.

IR (KBr) cm-1: 3520 (b, vO—H), 1754 (vC=O), 1581 (asym. vNO2), 1308 (sym. NO2), 1124 (vC—O).

Figure 34:
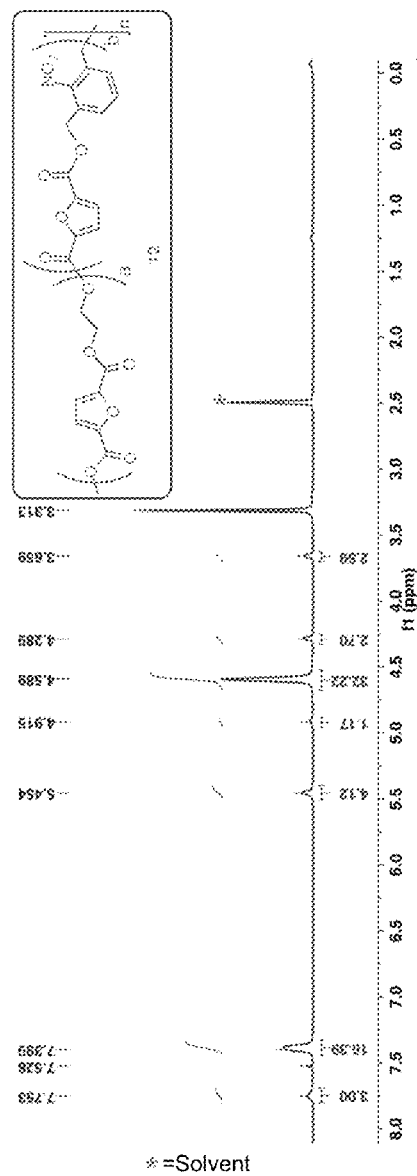
FIG. 34 is a $^1$H NMR spectrum (500 MHz, DMSO-d$_6$, δ ppm) of compound 12.

% Crystallinity of above copolymer/oligomer was determined by PXRD. It is calculated to be 21.05% with respect to Cristobalite (98% crystallinity) standard FIG. 34 is a $^1$H NMR and FIG. 35 is a $^{13}$C NMR of the co-polymer/oligomer 12.

Due to the presence of the ethylene glycol unit, the co-polymer 12 showed higher solubility than 11 and was partially soluble in common organic solvents (acetone, CHCl$_3$, DMSO) at room temperature but was completely soluble in DMSO at 75° C. $^1$H-NMR spectroscopic analysis of co-polymer 12 in DMSO-d6 showed proton resonances for the furan functionality around 7.39 ppm and the resonances nitrophenyl unit appeared around 7.76 and 5.45 ppm. The proton resonances of the ethylene glycol units appeared at 4.91, 4.59, 4.28 and 3.65 ppm.

Figures 36A, 36B, 36C:
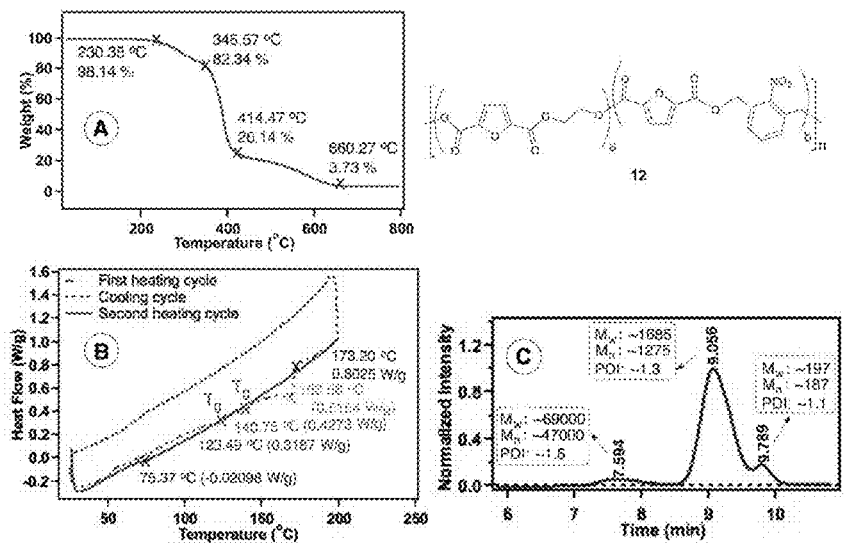
FIGS. 36A to 36C are characterization of copolymer 12: TGA of compound 12 (FIG. 36A), a DSC of compound 12 (FIG. 36B) and a GPC trace of compound 12 (FIG. 36C).
Figure 50:
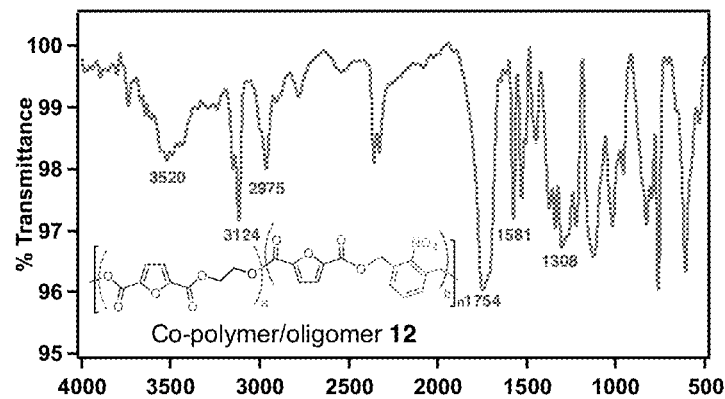
FIG. 50 shows FT-IR spectra of co-polymer/oligomer 12.
Figure 52:
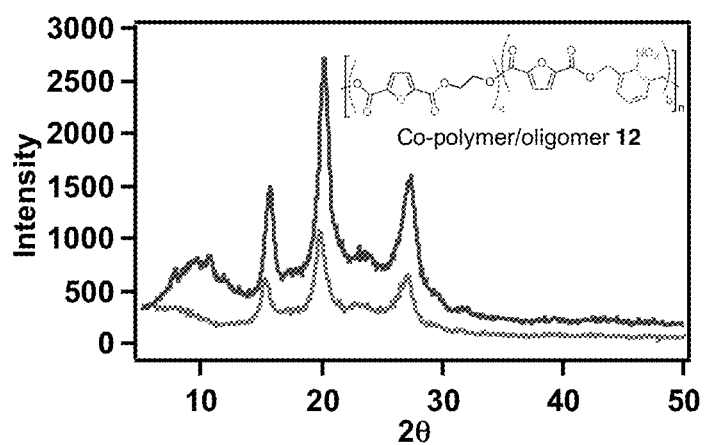
FIG. 52 shows a stacked PXRD pattern of three separately synthesized batches of co-polymer/oligomer 12.

FT-IR spectra of 12 showed the ester carbonyl vibration at 1739 cm as well as the characteristic asymmetric and symmetric stretching vibrations of the nitro group at 1581 and 1308 cm$^{-1}$ respectively (FIG. 50). The co-polymer 12 (Scheme 5) was sonicated in THF and the residue was filtered followed by GPC analysis of the supernatant. Inspection of FIG. 36c shows that the residue is a mixture of polymer ($M_w$: 69000; $M_n$: 47000 and PDI: 1.5), oligomer ($M_w$: 1685; $M_n$: 1275 and PDI: 1.3) and unreacted 6 (retention time 9.789 min). TGA analysis of the co-polymer 12 showed that it was thermally stable up to 230° C. (FIG. 36A). A weight loss of 13% was observed in the temperature range of 230-345° C., and a 56% weight loss was observed in the temperature range of 345-414° C. that likely indicated a decomposition of the co-oligomer/polymer. The decomposition was complete by 660° C. DSC thermogram of 12 (FIG. 36B) showed two glass transition temperatures at 123 and 140° C. during the first heating cycle that was likely due to the mixture of co-polymers present in the material viz., FDCA-glycol-nitrobenzyl co-polymer and FDCA-glycol polymer. There was an endotherm at 168° C. that did not correspond to a melting point as no visible crystallization exotherm was observed during the cooling cycle. During the second heating cycle, a shift in the glass transition temperature (75° C.) was observed that indicated an amorphous material. The DSC data for 12 was strikingly similar to the one observed for 11 (FIG. 31E). PXRD data for 12 can be found in FIG. 52

Figure 47:
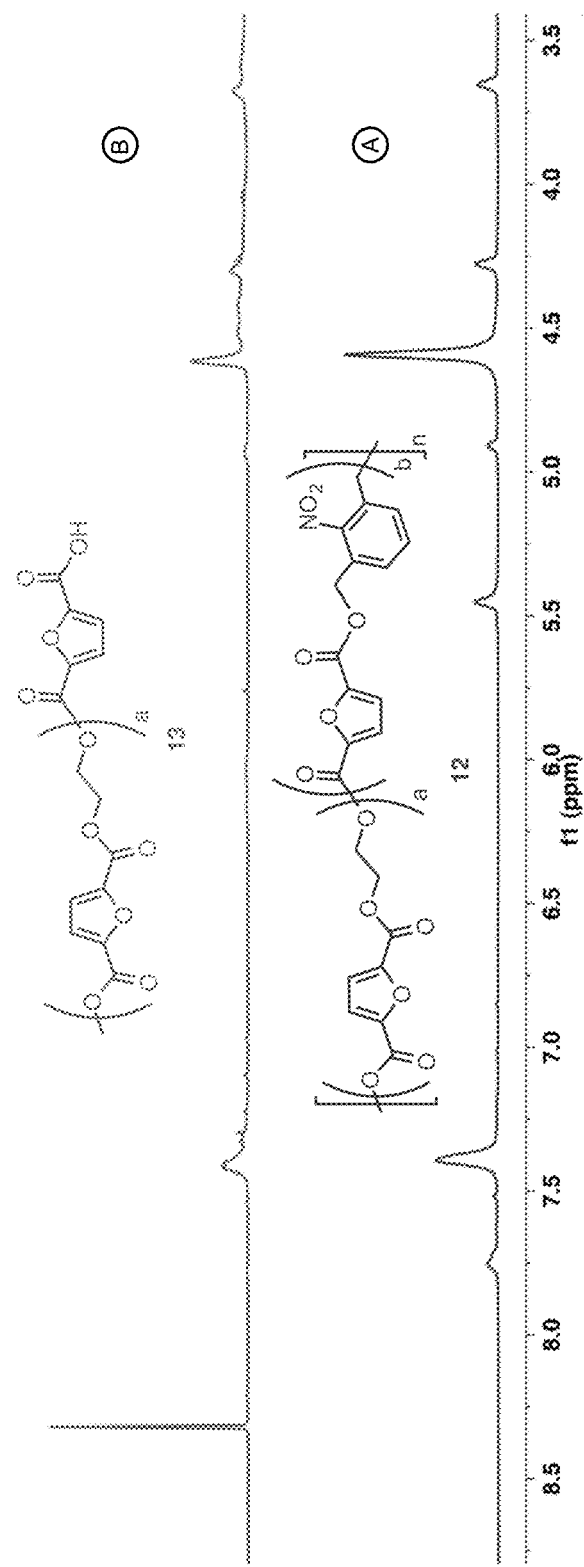
FIG. 47 shows $^1$H NMR spectra (500 MHz in DMSO-d$_6$) of compound 12 before irradiation and after 12 h irradiation (compound 13).

Having characterized the co-polymer 12, we proceeded to evaluate its photodegradability. A suspension of the co-polymer mixture in 4:1 THF-H$_2$O was irradiated at ~350 nm. The turbid solution turned transparent after irradiation and the solution was concentrated under reduced pressure. Analysis of the residue by $^1$H NMR spectroscopy indicated that the co-polymer 12 with the nitrobenzyl unit photodegraded efficiently (FIG. 47). Thus our strategy of employing phototriggers to degrade oligomers/polymers derived from biomass was successful with good recoverability of the monomer.

General procedures for irradiating compounds and/or polymers/oligomers that were used in the examples above include the following. Nitrobenzyl phototrigger based model compound 7a-b, 9 and polymeric/oligomeric compounds 11, co-polymer/oligomeric compound 12 in respective solvent were irradiated for a given time interval in pyrex tube in Rayonet reactor RPR-200 at 350 nm (16 bulbs×14 Watts). The photocleaved mixture was analyzed by NMR spectroscopy.

Conversion and Mass Balance after Photoreaction:

Mass balance and conversion of photocleaved compounds were obtained using triphenylmethane as an internal standard (IS). 1 mL of $10^{-2}$ M (122 mg in 50 mL of $CHCl_3$) solution of triphenylmethane was added to the crude product and evaporated. To the mixture of Internal standard and the photosylate about ~0.6 mL of deuterated solvent is added and 1H and $^{13}$C NMR was recorded. From the integral value of respective peaks, the % conversion and mass balance was calculated using the formula given below.

$$mol_a = mol_i \times \left(\frac{\text{Integral (analyte)}}{\text{Integral (analyte)}}\right) \times \frac{N_i}{N_a}$$

Where, Na and Ni are the number of nuclei giving rise to the relevant analyte and internal standard signals respectively. Similarly mola and moli are the molarity of analyte and the internal standard in deuterated solvent respectively.

Calculation for the Recovery of FDCA

Literature reported method was followed for the calculation of FDCA recovery.7 The recovery of FDCA from the irradiated polymer/oligomer sample was determined with NMR spectroscopy using an internal standard (IS). The mass of the FDCA was calculated from the integrated peak areas using the formula $$m_{FDCA} = \frac{MW_{FDCA}}{MW_{IS}} \times \frac{N_{FDCA}}{N_{IS}} \times \frac{m_{IS} \times A_{FDCA}}{A_{IS}}$$

Where mFDCA, mIS are the mass; NFDCA, NIS are the number of nuclei giving rise to the signals; AFDCA, AIS are the areas of the peak and MWFDCA, MWIS are the molecular weights of FDCA and IS respectively.

4.1 Photoreaction, Mass Balance and Conversion Studies of Ester Derivative 7a A 1 mM solution of 7a in THF-d8-D2O was employed for the mass balance and conversion studies. Schematic representation of the procedure is given below:

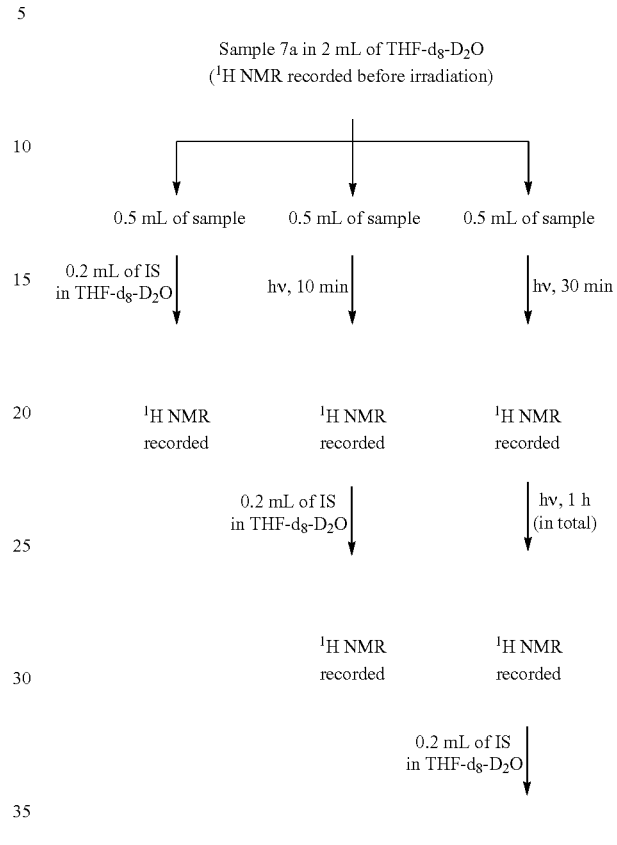

Conversion = 100%
Mass balance = 89%

Figure 37:
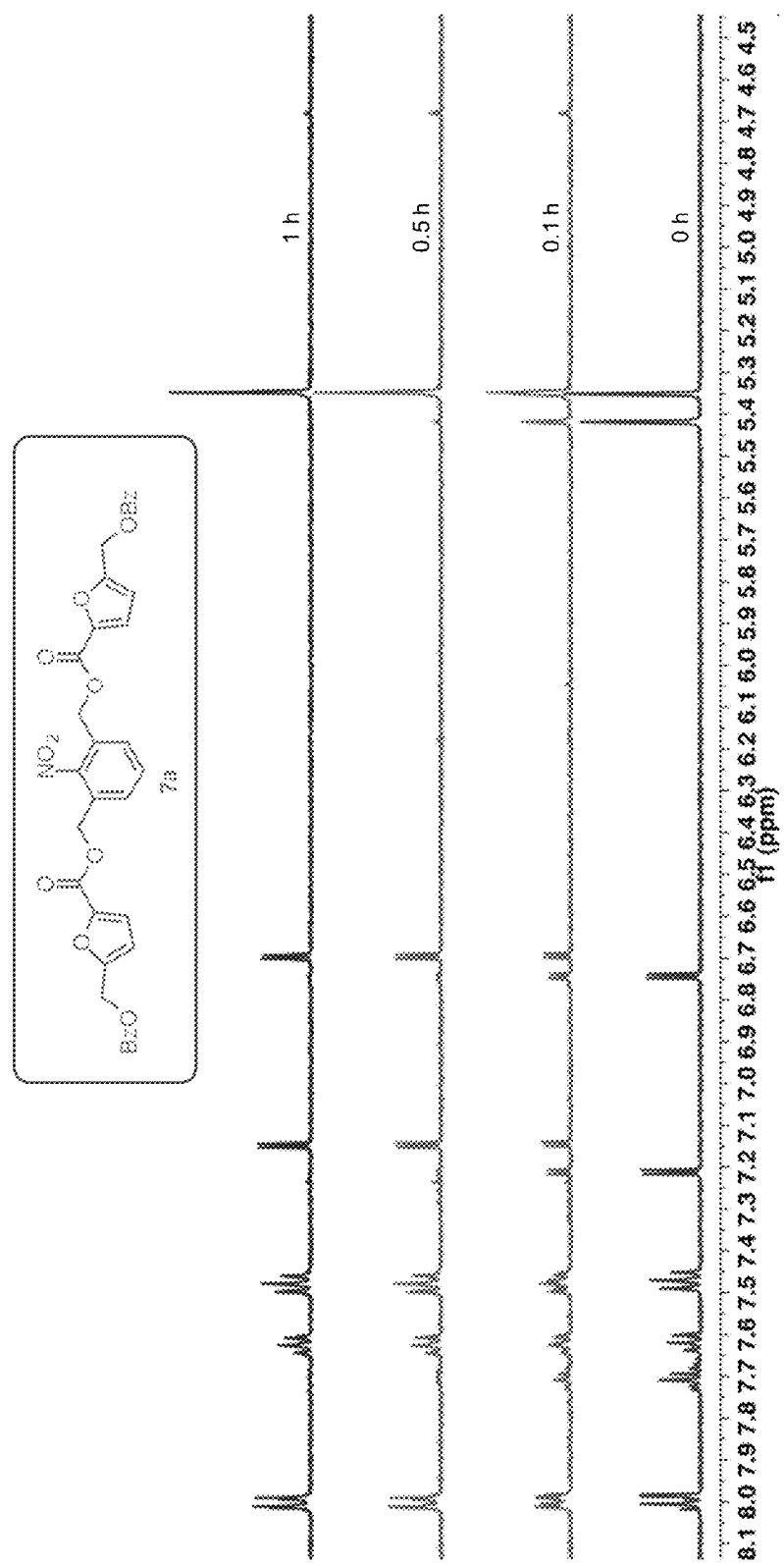
FIG. 37 shows $^1$H NMR spectra (500 MHz in THF-D$_2$O (4:1)) of compound 7a before irradiation (0 h) after 0.1 h irradiation, after 0.5 h irradiation and after 1 h irradiation.
Figure 38:
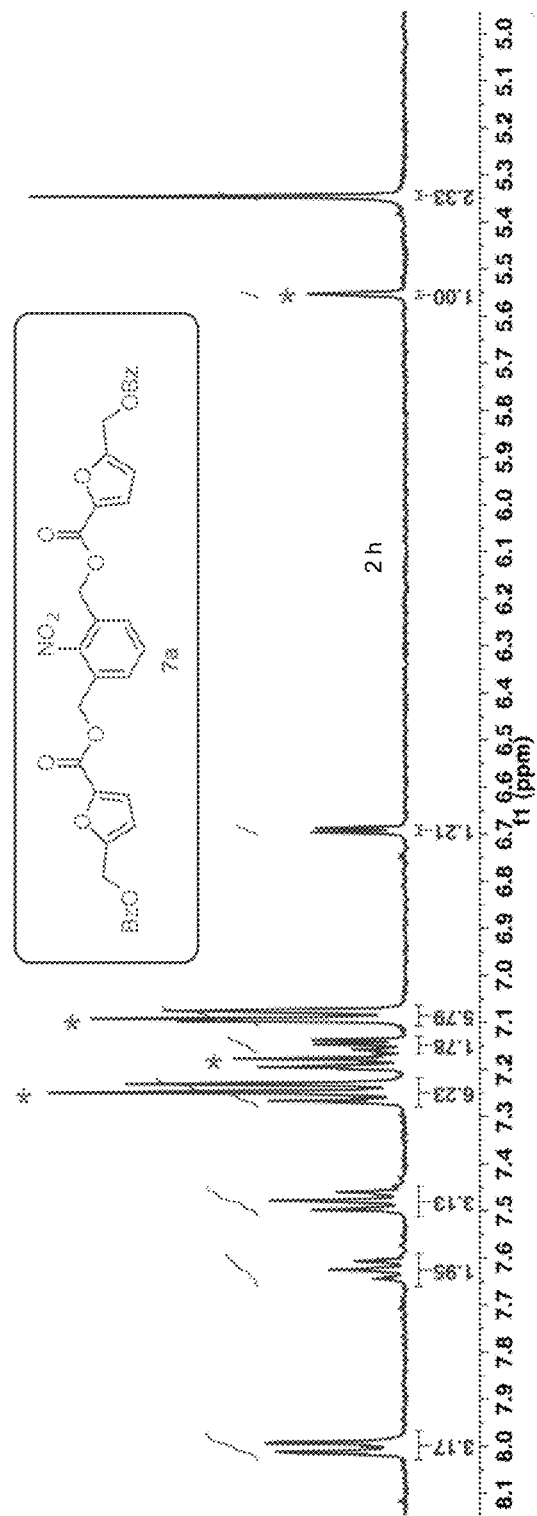
FIG. 38 shows a portion of the $^1$H NMR spectra (400 MHz in THF-D$_2$O (4:1)) of compound 7a after 2 h irradiation.

FIG. 37 shows a 500 MHz 1H NMR spectra of 7a irradiated at different time intervals. FIG. 38 shows 1H NMR spectra of 7a irradiated for 2 h (only a portion of the spectra is shown for clarity.)

Scheme S14: Photoreaction of ester derivative 7a

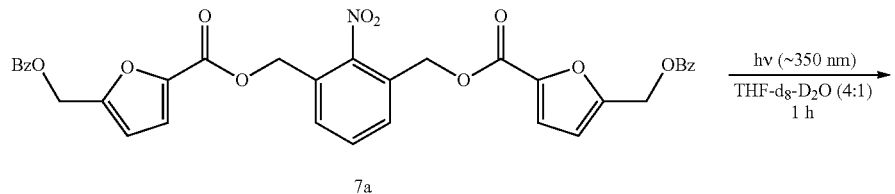

7a

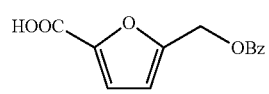

5a

4.2 Photoreaction, Mass Balance and Conversion Studies of Ester Derivative 7b Scheme S15: Photoreaction of ester derivative 7b

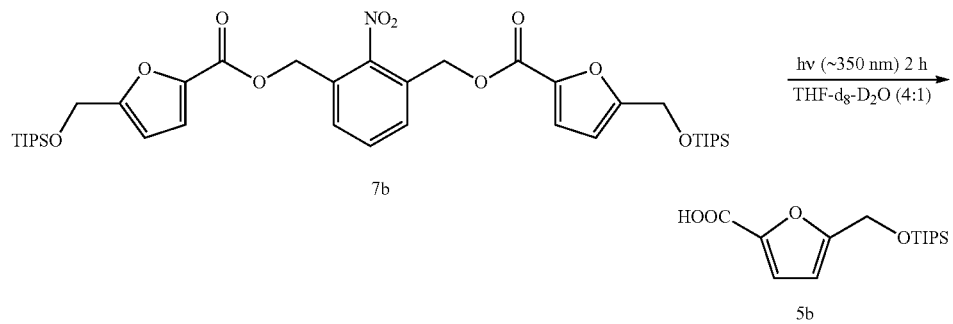

A 1 mM solution of 7b in THF-d8-D2O was employed for the mass balance and conversion studies. Schematic representation of procedure is given below:

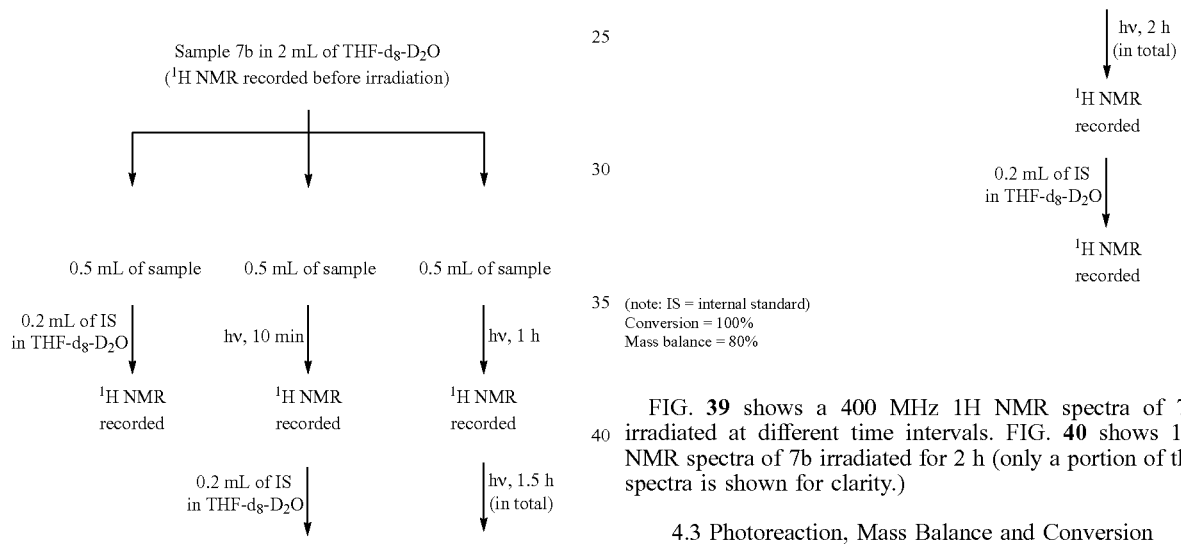

(note: IS = internal standard)
Conversion = 100%
Mass balance = 80%

Figure 39:
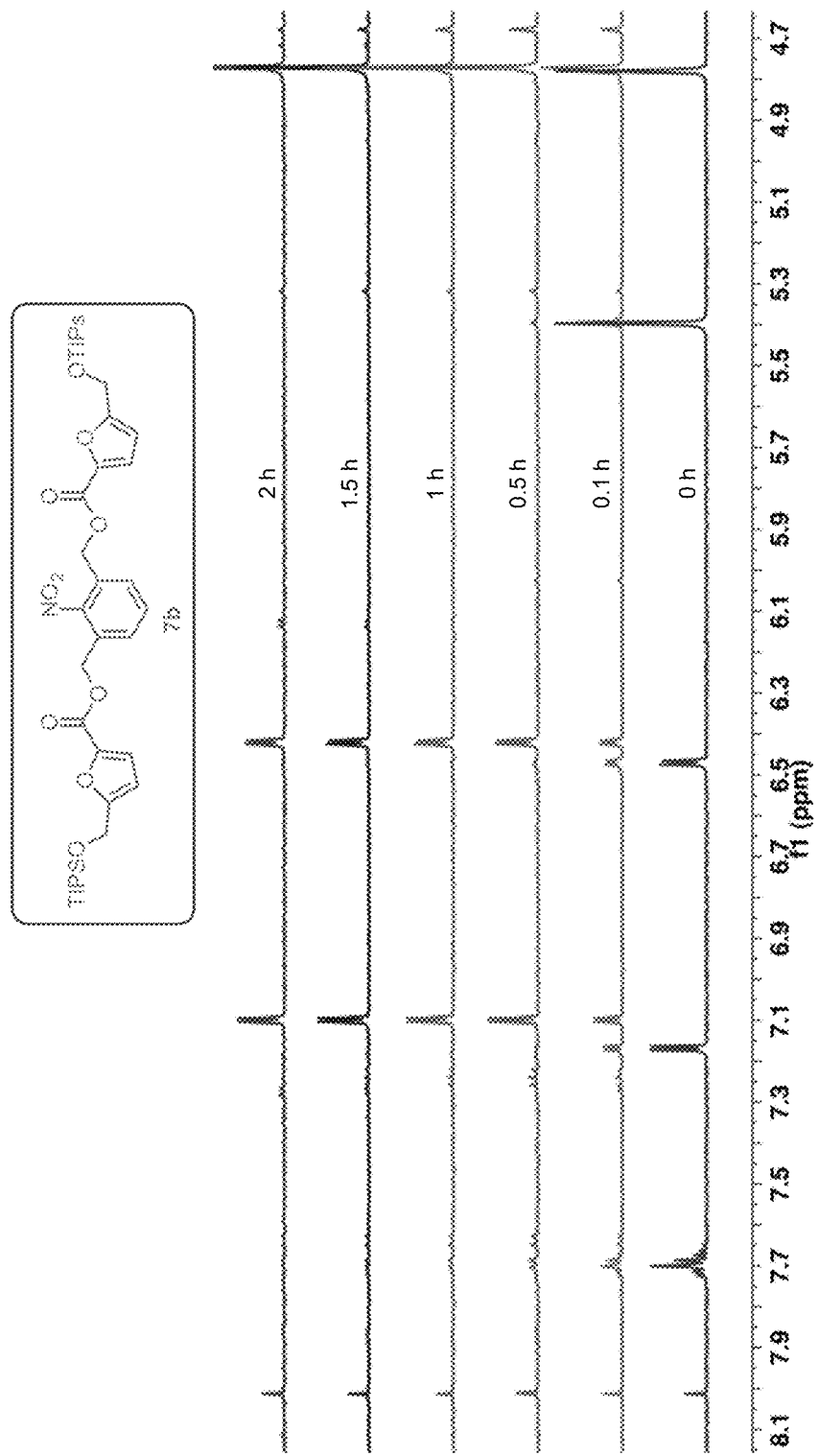
FIG. 39 shows $^1$H NMR spectra (400 MHz in THF-D$_2$O (4:1)) of compound 7b before irradiation (0 h) after 0.1 h irradiation, after 0.5 h irradiation, after 1 h irradiation, after 1.5 h irradiation, and after 2 h irradiation.
Figure 40:
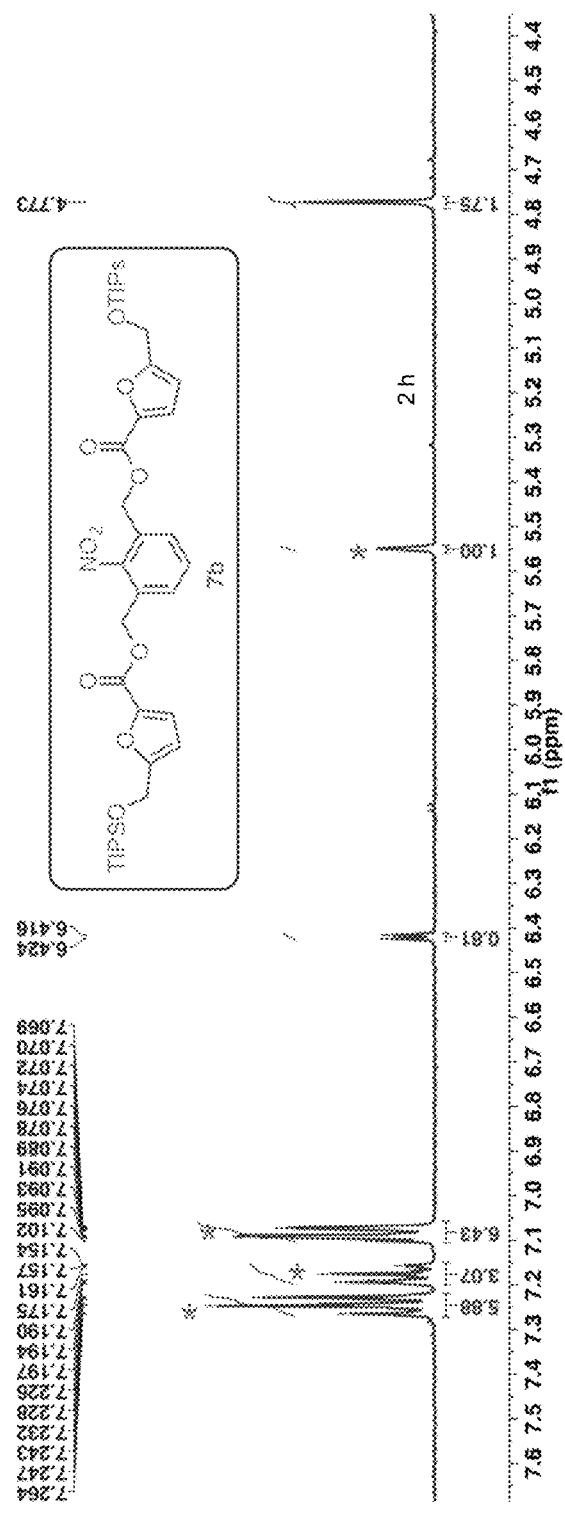
FIG. 40 shows a portion of the 2 h trace in FIG. 39.

FIG. 39 shows a 400 MHz 1H NMR spectra of 7b irradiated at different time intervals. FIG. 40 shows 1H NMR spectra of 7b irradiated for 2 h (only a portion of the spectra is shown for clarity.)

4.3 Photoreaction, Mass Balance and Conversion Studies of Ester Derivative 9

Scheme S16: Photoreaction of ester derivative 9

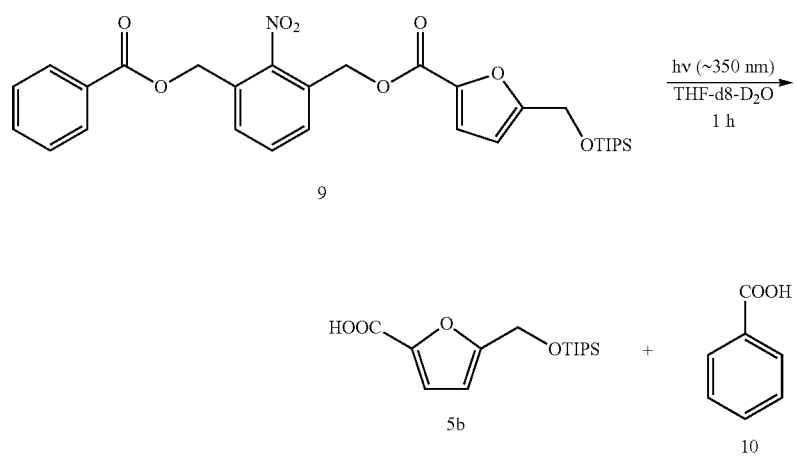

A 5 mM solution of ester 19 in THF-d8-D2O (NMR tube) was irradiated for 1 h. For every 0.5 h photocleavage was followed up 1H NMR spectrum. Schematic representation of procedure is given below:

Sample 9 in 0.5 mL of THF-d$_8$-D$_2$O
($^1$H NMR recorded before irradiation)

hv, 10 min ↓

$^1$H NMR recorded hv, 40 min (in total) ↓

$^1$H NMR recorded hv, 60 min (in total) ↓

-continued $^1$H NMR recorded 0.2 mL of IS in THF-d$_8$-D$_2$O ↓

$^1$H NMR recorded (note: IS = internal standard)
Conversion = 100%
Mass balance = 60% (for furan acid, 5b) and 74% (for benzoic acid, 10)

Figure 42:
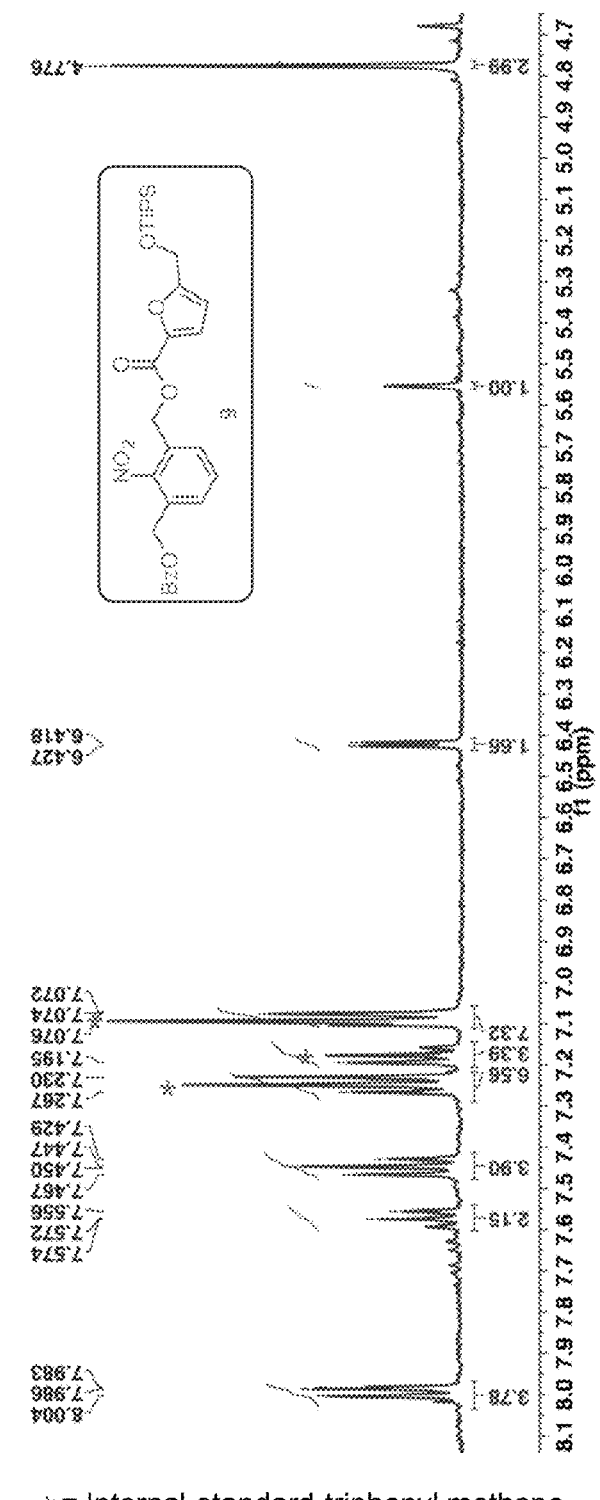
FIG. 42 shows a portion of the traces in FIG. 41.

FIG. 41 shows a 400 MHz 1H NMR spectra of 9 irradiated at different time intervals. FIG. 42 shows 1H NMR spectra of 9 irradiated for 1 h (only a portion of the spectra is shown clarity.)

Previous studies in the literature, done on nitrobenzyl phototriggers, established that the presence of the nitro group is necessary for the hydrogen abstraction leading to photocleavage resulting in nitroso aldehyde photoproduct. The above studies were performed with nitrobenzyl compounds that feature substitution at one of the ortho positions. However, disclosed polymer/oligomers have both the ortho positions of the nitrobenzyl trigger functionalized/substituted. This makes the break down mechanism more complicated, as the nitroso aldehyde has to initiate the second cleavage for complete decomposition leading to monomer (the carboxylic acid that was originally used to synthesize the model compounds).

Scheme 4

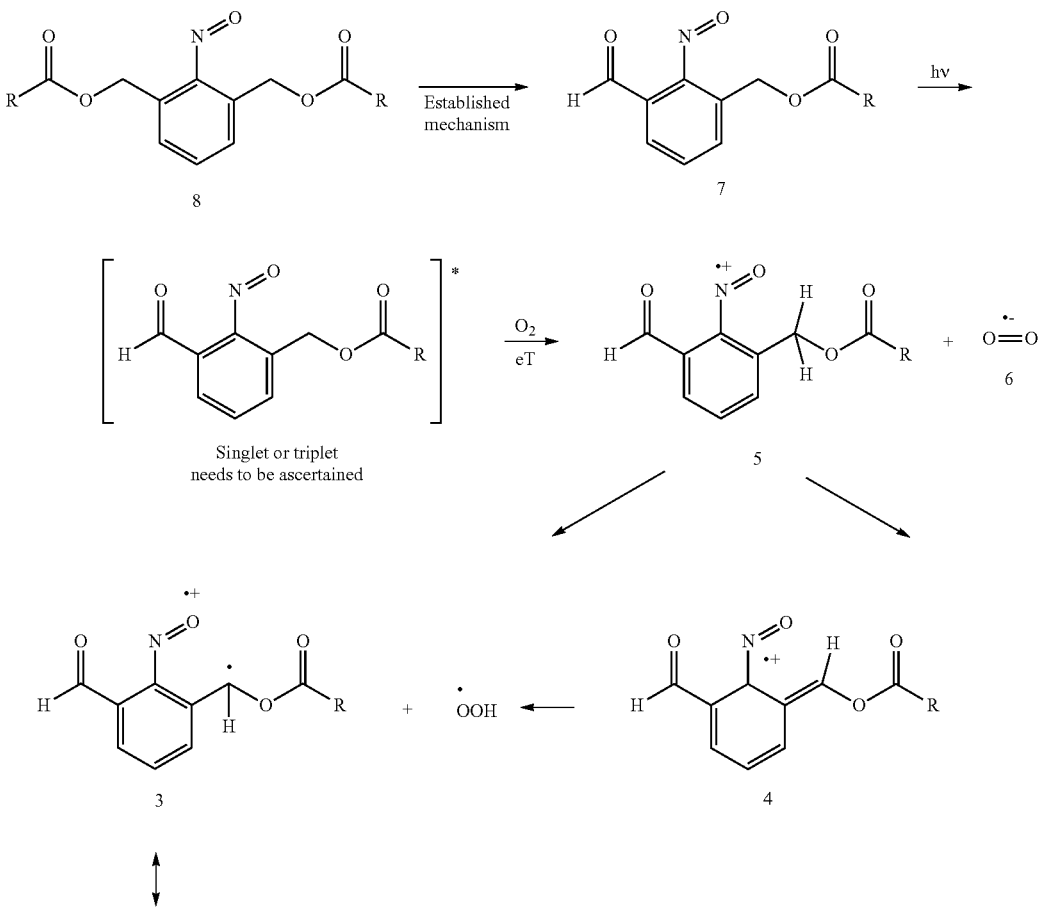

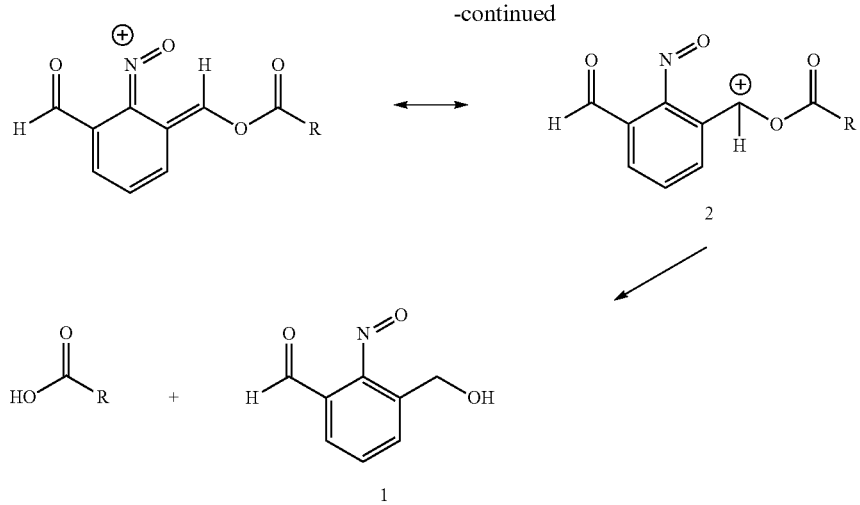

Figure 53A:
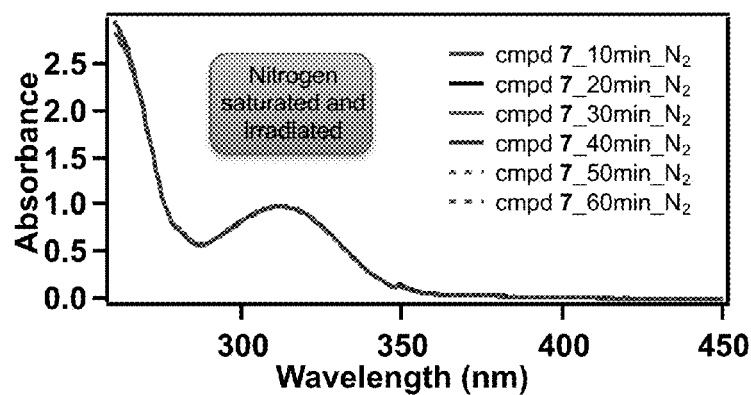
FIGS. 53a, 53b, and 53c are UV-VIS spectra of nitrogen saturated nitroso derivative in THF-H$_2$O irradiated at different time intervals (FIG. 53a), oxygen saturated nitroso derivative in THF-H$_2$O irradiated at different time interval (FIG. 53b), and oxygen saturated nitroso derivative in THF-H$_2$O at different time interval (FIG. 53c).
Figure 53B:
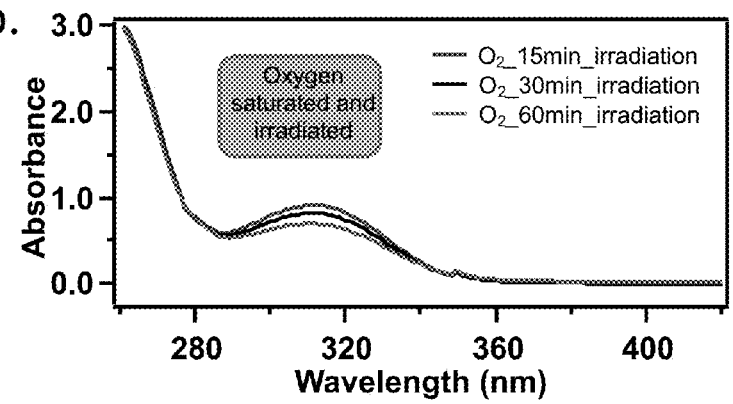
Figure 53C:
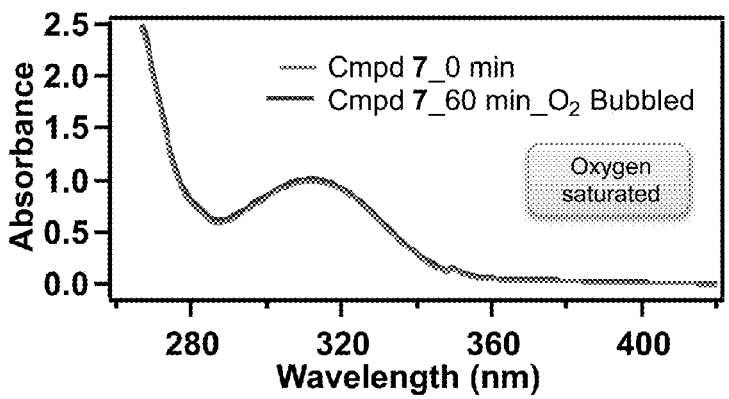

To understand the mechanistic aspect of photodegradation in disclosed polymer(s)/oligomer(s), systematic investigations were carried out into nitro trigger functionalized model compounds that are substituted at both the ortho positions. The monocleaved nitroso compound was successfully isolated. No decomposition of the nitrosoaldehyde 7 (Scheme 4) was observed upon light exposure in the presence of nitrogen atmosphere as evidenced by UV-Vis spectral analysis (FIG. 53a). This indicated that the nitroso group was intact during the photoprocess as the cleavage of nitrosoaldehyde was not observed. On the other hand, exposure of nitrosoaldehyde 7 to UV light (scheme 4) under oxygen saturated conditions showed a decrease in absorptivity (FIG. 53b) indicating reaction progress leading to cleavage at the second ortho-position. No decomposition of 7 was observed in the absence of light under oxygen atmosphere (FIG. 53c). The above observations clearly indicate that both light and oxygen are necessary for the cleavage process.

Based on the above observations a mechanism is proposed herein in which the initial/first photocleavage of ortho-disubstituted nitrotriggers occurred via established mechanistic pathways. Based on the above mechanistic study, the second cleavage, upon excitation of nitroso aldehyde, likely occurs in the presence of oxygen via electron transfer as depicted in Scheme 4 leading to the monomer (acid).

Our efforts towards addressing degradability of oligomers/polymers derived from biomass-based monomers have the potential to foster development to address the need to utilize renewable resources to build materials that are environmentally benign. While our initial study detailed in this report is on model systems, the test of our hypothesis demonstrated that programmed degradation of oligomers/polymers derived from biomass is indeed feasible. In addition, our strategy allowed for recovery of the monomer that opens up avenues to reuse the monomer derived from biomass. Our strategy has the potential to build novel materials from biomass that are degradable with light after usage mitigating the stress of unwanted chemicals in our environment.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications including provisional patent applications, publications including patent publications and nonpatent publications, and electronically available material cited herein are incorporated by reference.

What is claimed is:

1. A photodegradable polymer derived from:
at least one bifunctional first monomeric unit, wherein the first monomeric unit is selected from monomers of formula III:

 (III), where J is

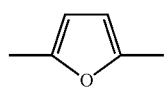

f is 0, 1 2, 3, 4 or 5; and
g is 0, 1, 2, 3, 4 or 5; and at least one second monomeric unit comprising a nitrobenzyl phototrigger.

2. The photodegradable polymer of claim 1, wherein f and g are independently 1, 2, 3, 4, or 5.

3. The photodegradable polymer of claim 1, wherein f and g are both 2.

4. The photodegradable polymer of claim 1, wherein the first monomeric unit is selected from:

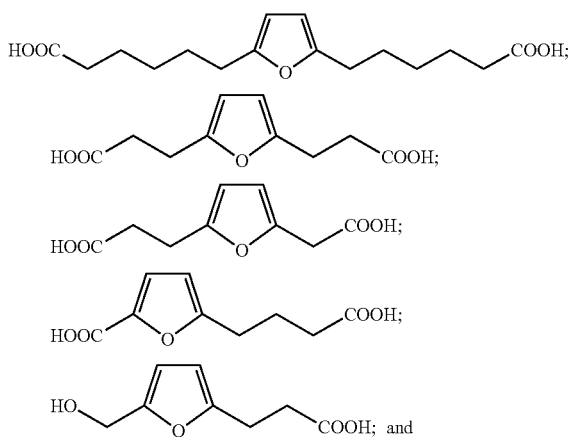

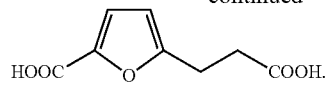

5. The photodegradable polymer of claim 1, wherein the second monomeric unit comprises a residue of 2-nitro-1,3-benzenedimethanol.

6. The photodegradable polymer of claim 1 further comprising at least one third monomeric unit, wherein the third monomeric unit is obtained from a petroleum product or is chemically or enzymatically synthesized.

7. The photodegradable polymer of claim 6, wherein the third monomeric unit comprises a hydrophilic monomer.

8. The photodegradable polymer of claim 7, wherein the hydrophilic monomer comprises an alkylene glycol.

9. The photodegradable polymer of claim 1, wherein the polymer contains excess molar equivalents of the first monomeric units with respect to the second monomeric units.

10. The photodegradable polymer of claim 6, wherein the polymer contains excess molar equivalents of the first monomeric units, the third monomeric units, or both with respect to the second monomeric units.

11. A method for recycling the polymer according to claim 1, the method comprising irradiating the polymer in order to yield recycled monomers or oligomers.

12. The method according to claim 11, wherein irradiation comprises UV radiation.

* * * * *